US011916180B2

(12) United States Patent
Lee et al.

(10) Patent No.: US 11,916,180 B2
(45) Date of Patent: Feb. 27, 2024

(54) ORGANIC SOLAR CELL AND PHOTODETECTOR MATERIALS AND DEVICES

(71) Applicant: The Regents of the University of California, Oakland, CA (US)

(72) Inventors: Jaewon Lee, Goleta, CA (US); Soe-Jin Ko, Goleta, CA (US); Jianfei Huang, Goleta, CA (US); Martin Seifrid, Goleta, CA (US); Hengbin Wang, Santa Barbara, CA (US); Thuc-Quyen Nguyen, Santa Barbara, CA (US); Guillermo C. Bazan, Santa Barbara, CA (US)

(73) Assignees: THE REGENTS OF THE UNIVERSITY OF CALIFORNIA, Oakland, CA (US); THE MITSUBISHI CHEMICAL CORPORATION, Tokyo (JP)

( * ) Notice: Subject to any disclaimer, the term of this patent is extended or adjusted under 35 U.S.C. 154(b) by 704 days.

(21) Appl. No.: 16/792,000

(22) Filed: Feb. 14, 2020

(65) Prior Publication Data
US 2020/0328357 A1    Oct. 15, 2020

Related U.S. Application Data

(60) Provisional application No. 62/866,797, filed on Jun. 26, 2019, provisional application No. 62/806,232, filed on Feb. 15, 2019.

(51) Int. Cl.
*H01L 31/00* (2006.01)
*C07D 495/04* (2006.01)
(Continued)

(52) U.S. Cl.
CPC ........ *H01L 51/0074* (2013.01); *C07D 495/04* (2013.01); *H01L 51/0053* (2013.01);
(Continued)

(58) Field of Classification Search
CPC ............. H01L 51/0074; H01L 51/0053; H01L 51/0058; H01L 51/0068; H01L 51/4273; C07D 495/04
See application file for complete search history.

(56) References Cited

PUBLICATIONS

Yao et al., ("Design, Synthesis, and Photovoltaic Characterization of a Small Molecular Acceptor with an Ultra-Narrow Band Gap"), Angew. Chem. Int. Ed. 2017, 56, 3045-3049. (Year: 2017).*
(Continued)

*Primary Examiner* — Thanh Truc Trinh
(74) *Attorney, Agent, or Firm* — GATES & COOPER LLP

(57) ABSTRACT

Narrow bandgap n-type small molecules are attracting attention in the near-infrared organic optoelectronics field, due to their easy tunable energy band with a molecular design flexibility. However, only a few reports demonstrate narrow bandgap non-fullerene acceptors (NFAs) that perform well in organic solar cells (OSCs), and the corresponding benefits of NFA photodiodes have not been well investigated in organic photodetectors (OPDs). Here, the ultra-narrow bandgap NFAs CO1-4F, CO1-4Cl and o-IO1 were designed and synthesized for the achieved efficient near-infrared organic photodiodes such as solar cells and photodetectors. Designing an asymmetrical CO1-4F by introducing two different π-bridges including alkylthienyl and alkoxythienyl units ultimately provides an asymmetric A-D'-D-D"-A molecular configuration. This enables a delicate modulation in energy band structure as well as maintains an intense intramolecular charge transfer characteristic of the excited state.

18 Claims, 35 Drawing Sheets

(51) Int. Cl.
 *H01L 51/00* (2006.01)
 *H01L 51/42* (2006.01)
(52) U.S. Cl.
 CPC ...... *H01L 51/0058* (2013.01); *H01L 51/0068* (2013.01); *H01L 51/4273* (2013.01)

(56) References Cited

PUBLICATIONS

Rasmussen et al., ("Dithieno [3,2-b:2',3'-d]pyrrole-based materials: Synthesis and application to organic electronics"), Progress in Polymer Science 38 (2013) 1773-1804. (Year: 2013).*

Zhang et al., "Small-Molecule Electron Acceptors for Efficient Non-fullerene Organic Solar Cells", Frontiers in Chemistry, Sep. 2018, vol. 6, Article 414. pp. 1-22. (Year: 2018).*

Huang, J., et al., "High-Performance Solution-Processed Organic Photodetector for Near-Infrared Sensing", Advanced Materials, Nov. 2019, pp. 1-43, vol. 32, No. 1, https://doi.org/10.1002/adma.201906027, including supporting information.

Lee, J., et al., "Side Chain Engineering of Non-Fullerene Acceptors for Near-Infrared Organic Photodetectors and Photovoltaics", ACS Energy Letters, May 2019, pp. 1401-1409, vol. 4, No. 6, https://doi.org/10.1021/acsenergylett.9b00721, including supporting information.

Lee, J., et al., "Bandgap Tailored Nonfullerene Acceptors for Low Energy Loss Near-Infrared Organic Photovoltaics", Unpublished.

* cited by examiner (g)

$X_1$, $X_2$ or $X_3$ = halogen, CN or alkoxy, alkylthio or N- or S- annulated
$Y_1$, $Y_2$, $Y_3$ or $Y_4$ = S or O
$R_1$ or $R_2$ = H or solubilizing chain Y or Z = CH, CF, N, C-CN or C-OR
X = O, S, Se or N-R where R is H or solubilizing chain $R_1$ or $R_2$ = H or any sort of solubilizing chain
Ar = any sort of aryl unit $X_1$ or $X_2$ = O, S, malonitrile
Y = Halogen, -CN or any solubilizing chain
(any number of substituents)
Ar = any sort of aryl unit $Y_1$, $Y_2$ or $Y_3$ = O, S or malonitrile
R, $R_1$ and $R_2$ = any solubilizing chain or H R = H or any solubilizing chain $X_1$ or $X_2$ = methyl or trifluoromethyl X = O, S, Se
R = H or any solubilizing chain R = H or any solubilizing chains
$Y_1$ or $Y_2$ = S, O or malonitrile
Ar = any aryl unit

BDT based polymers

CPDT (dithienocyclics) based polymers

PM2

PIPCP

X = C, Si, or Ge

DPP based polymers

DTP based polymer

ORGANIC SOLAR CELL AND PHOTODETECTOR MATERIALS AND DEVICES

CROSS REFERENCE TO RELATED APPLICATIONS

This application claims the benefit under 35 U.S.C. Section 119(e) of the following and commonly-assigned applications:

U.S. Provisional Patent Application No. 62/806,232, filed Feb. 15, 2019, by Jaewon Lee, Seo-Jin Ko, Jianfei Huang, Martin Seifrid, Hengbin Wang, Thuc-Quyen Nguyen, and Guillermo C. Bazan, entitled "ORGANIC SOLAR CELL AND PHOTODETECTOR MATERIALS AND DEVICES"; and U.S. Provisional Patent Application No. 62/866,797, filed Jun. 26, 2019, by Thuc-Quyen Nguyen, Jianfei Huang, Jaewon Lee, Guillermo C. Bazan, and Hengbin Wang, entitled "ORGANIC SOLAR CELL AND PHOTODETECTOR MATERIALS AND DEVICES";

all of which applications are incorporated by reference herein.

BACKGROUND OF THE INVENTION

1. Field of the Invention

The present invention relates to organic semiconducting molecules and devices including the same.

2. Description of the Related Art (Note: This application references a number of different publications as indicated throughout the specification by one or more reference numbers as superscripts, e.g., [x]. A list of these different publications ordered according to these reference numbers can be found below in the section entitled "References." Each of these publications is incorporated by reference herein.)

Organic optoelectronic devices have attracted attention for their inherent characteristics to be printed into ultra-thin, flexible, and conformal products through low-cost solution-processing techniques.[1,2] Organic semiconductors offer clear advantages related to their molecular diversities of organic chromophores which allow organic photodiodes to be explored for a wide range of optical applications by tailoring the absorption spectra.[3-7] Near-infrared (MR) responsive organic solar cells (OSCs) provide the potential in future applications such as semitransparent devices for building-integrated or green house system[8-10] With a similar working principle to OSCs, organic photodetectors (OPDs) with NIR responsivity have plenty of applications such as image sensing, night surveillance, optical communication, and health monitoring.[11-13] Considering that the spectral response window of organic semiconductors can be readily tuned by rational molecular design, MR OPDs have been emerged as a cost effective material choices; typically, epitaxial grown inorganic materials such as InGaAs or quantum dots are cost intensive. Due to the low dielectric constant of organic materials, however, the excitons are strongly bound by Coulombic attraction with energies of hundreds of millielectronvolts, much higher than the thermal energy at room temperature ($k_BT \approx 0.026$ eV), thereby limiting the charge generation.[3] This problem has been largely resolved by using bulk-heterojunction (BHJ) consisting of a donor and an acceptor components to promote the charge separation.[14-16]

Narrow bandgap (NBG) non-fullerene electron acceptors (NFA) are an emerging class of NIR organic absorbers that overcome the shortages of the BHJ photodiodes based on the fullerenes. Of note are the structural flexibility that provides an opportunity to promote an energy level variability as well as to tailor absorption characteristics toward NIR light with outstanding optoelectronic responses such as efficient charge generation with low photon energy losses.[17-19] In this context, the recent impressive improvement in device efficiency of OSC is expected to be of particular relevance with the advent of highly efficient MR NFA materials.[20-25] Conversely, the vast majority of state-of-the-art OPD systems comprise a narrow bandgap polymer governing the absorption range of the device, combined with a fullerene.[13] These OPDs are expected to exhibit disadvantages over commercially available inorganic devices (e.g. their relatively low photoresponsivities in the NIR region), which can be attributed to intrinsic properties of the fullerene acceptor.

What is needed then, is to transfer the benefits of non-fullerene solar cells, in terms of superior optoelectronic properties, over fullerene-based devices to realize efficient NIR organic photodetectors and solar cells. The present disclosure satisfies this need.

SUMMARY OF THE INVENTION

A series of novel asymmetric non-fullerene acceptor materials were developed. The acceptor materials adopted asymmetric A-D1-D2-D3-A (or A-D'-D-D"-A, or A'-D'-D-D"-A') structure with D1 (D'), D2 (D), D3 (D") as different donor units. In one or more examples, the materials exhibit narrow bandgap of less than 1.3 eV and strong optical absorption coefficient.

The composition of matter may be embodied in many way including, but not limited to, the following.

1. A composition of matter, comprising an organic semiconducting molecule having an A-D'-D-D"-A structure, wherein D' is a donor moiety comprising an alkoxythienyl, D is a donor moiety comprising a dithiophene, and D" is a donor moiety comprising an alkylthienyl, and A is an acceptor moiety comprising (3-oxo-2,3-dihydro-1H-inden-1-ylidene)malononitrile (IC).

2. A composition of matter, comprising one or more organic semiconducting molecules each having a structure (and isomers thereof):

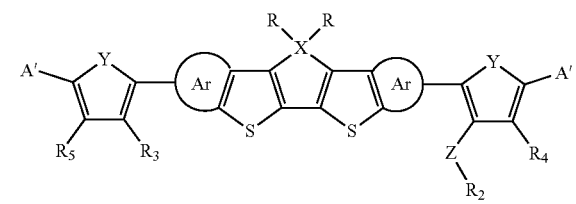

where in:
each Ar is independently a substituted or non-substituted aromatic functional group, or each Ar is independently nothing and the valence of its respective thiophene ring is completed with hydrogen;
X is C, Si, Ge, N or P; Y is O, S, Se or N—$R_6$;
Z is O, S, Se, or N—$R_6$;

each R, $R_1$, $R_2$, $R_3$, $R_4$, $R_5$ and $R_6$ is independently hydrogen or a substituted or non-substituted alkyl, aryl or alkoxy chain but $R_3$ is different from Z—$R_2$;

$R_4$ is either a hydrogen or the same as Z—$R_2$;

$R_5$ is either a hydrogen or the same as $R_3$; and

A' is an acceptor moiety.

2. The composition of matter of embodiment 2, wherein A' has the structure (and isomers thereof):

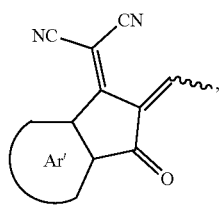

where

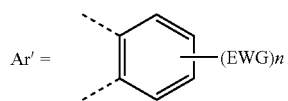

wherein EWG is any electron withdrawing group.

3. The composition of matter of embodiment 3, wherein Ar' is one of the following:

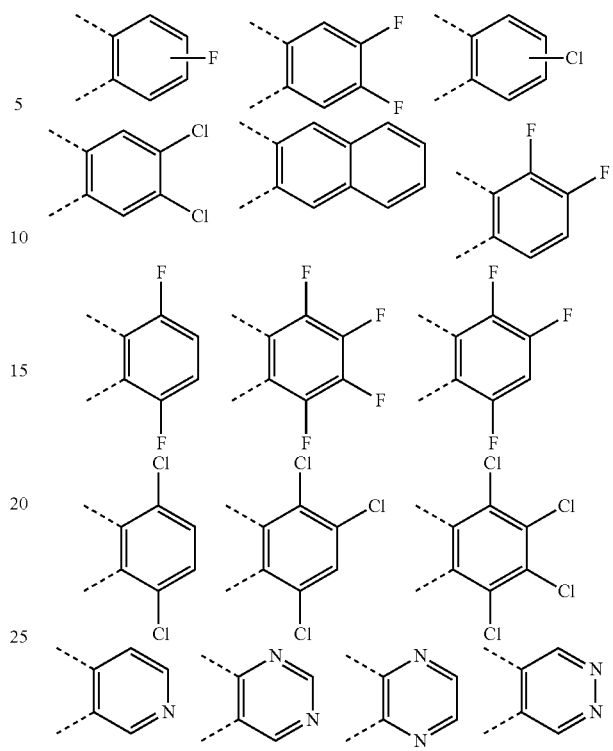

4. A composition of matter of the structure (and isomers thereof):

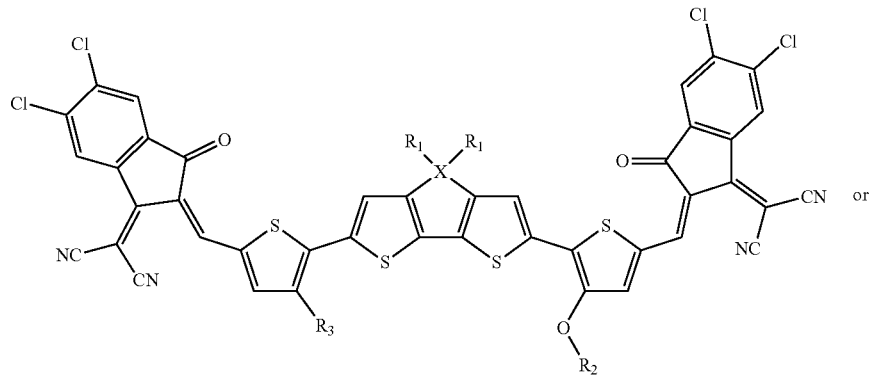

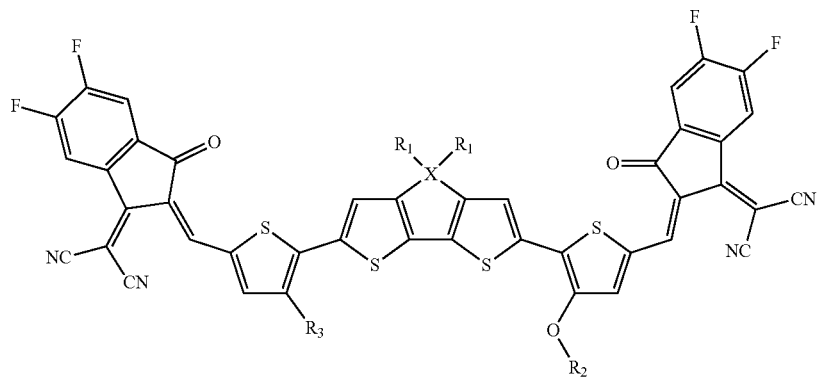

wherein X is C, Si, Ge, N or P; Each $R_1$, $R_2$ and $R_3$ is independently hydrogen or a substituted or non-substituted alkyl, aryl or alkoxy chain, and $R_3$ is different with $OR_2$.

5. The composition of matter of embodiment 4 having the structure of one of the following:

HOMO in a range of −5.0 eV to −5.5 eV, a LUMO in a range of −3.8 eV to −4.3 eV, and a bandgap in a range of 1.0 eV to 1.4 eV.

8. The composition of matter of any of the embodiments 1-6, wherein the organic semiconducting molecule has a bandgap narrower than 1.3 eV.

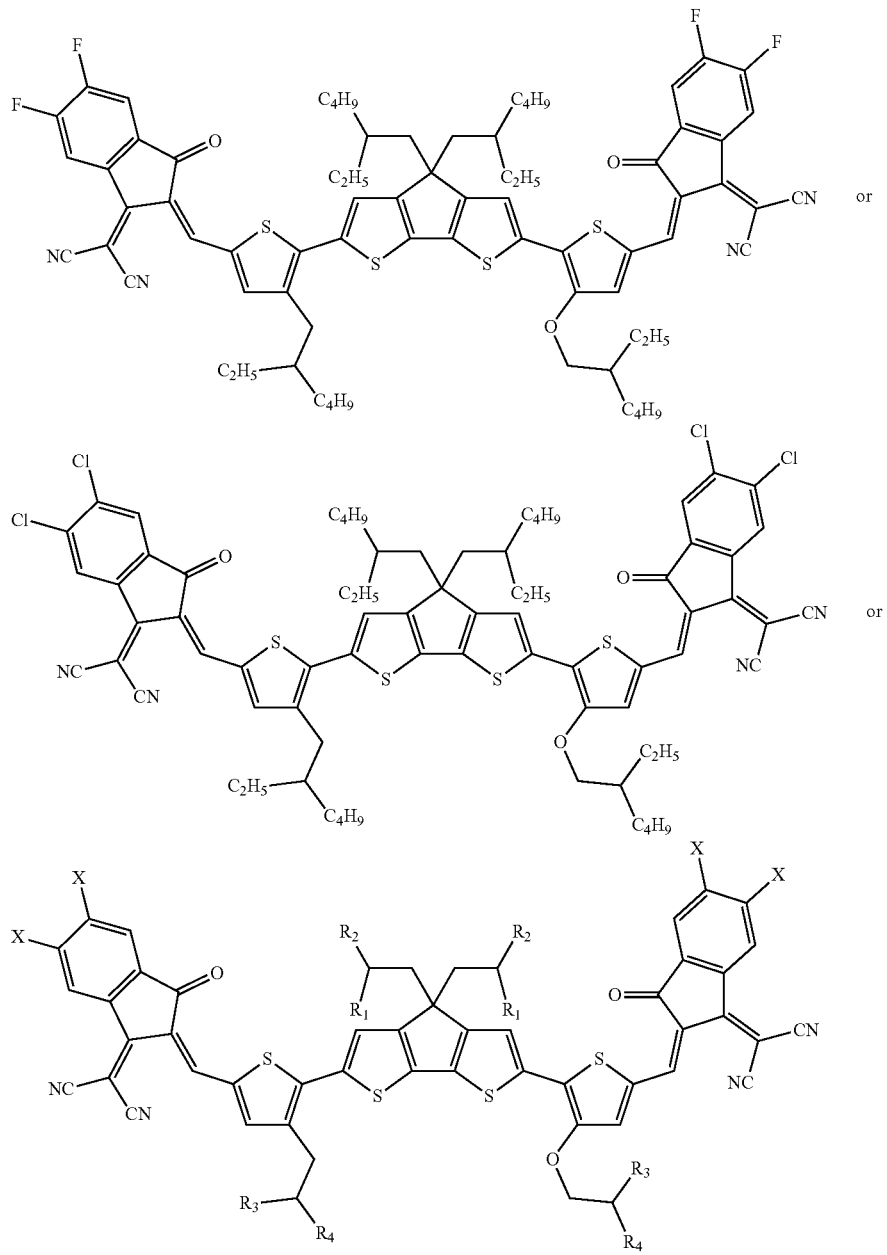

where:
X is F or Cl, and
$R_1$, $R_2$, $R_3$, $R_4$ are independently hydrogen or a substituted or non-substituted alkyl, aryl or alkoxy chain.

6. The composition of matter of any of the embodiments 1-5, wherein the dithiophene has side chains (e.g. $R_1$) soluble in a solvent used to solution process a device comprising the composition of matter.

7. The composition of matter of any of the embodiments 1-6, wherein the organic semiconducting molecule have a 9. A device comprising an active region including the composition of matter of any of the embodiments 1-8, wherein each of the organic semiconducting molecules is an electron acceptor.

10. The device of embodiment 9, comprising an active region comprising each of the electron acceptors forming a heterojunction with an electron donor comprising a second organic semiconducting molecule, and wherein the active region has a thickness of at least 300 nanometers or in a range of 200 nm to 1 micrometer.

11. The device of embodiment 9 or 10, further comprising:
    a cathode;
    an anode; and
    the active region between the cathode and the anode; and wherein:
    holes and electrons are generated in the active region in response to electromagnetic radiation incident on the active region,
    the electrons are collected in the electron acceptor and are transmitted through to the cathode, and
    the holes are collected in the electron donor and transmitted through to the anode.

12. The device of embodiment 11, further comprising:
    a hole blocking layer between the cathode and the active region, and
    an electron blocking layer between the anode and the active region.

13. The device of embodiment 9, 10, 11, or 12 wherein the device is an organic solar cell and the active region outputs current in response to sunlight absorbed in the composition of matter.

14. The device of any of the embodiments 9-12, wherein the active region is the sensing element in an infrared photodetector, or wherein the device is a photodetector outputting current in response to infrared electromagnetic radiation absorbed in the active region.

15. The device of any of embodiments 9-15, wherein the device has an external quantum efficiency (EQE) above 60% in the wavelength range of 600-950 nm.

16. The composition of matter or the device of any of the embodiments 1-16 further comprising an organic semiconducting donor molecule combined with one or more of the organic semiconducting molecule(s).

17. The composition of matter of embodiment 12, wherein the donor molecule is at least one compound selected from PTB7-Th, another BDT based polymer, a CPDT based polymer, a DPP based polymer, or a DTP based polymer or from the list of compounds illustrated in FIGS. 20A-20F.

18. The composition of matter of embodiments 16 or 17, comprising a plurality of the donor molecules and a plurality of the organic semiconducting molecule that are phase separated, wherein the organic semiconducting molecules are disposed in a hierarchical network and the donor molecules occupy spaces in the hierarchical network.

19. The composition of matter of embodiment 18, wherein the hierarchical network comprises larger mid rib shaped regions connected by smaller or thinner regions.

20. The composition of matter of any of the embodiments 18-19, wherein the composition of matter is solution processed with an additive that promotes formation of the hierarchical network.

21. A method of making a device, comprising solution processing the composition of matter of embodiments 18-20 in an active region of a solar cell, photodetector, or transistor; and combining the composition of matter with an additive so that (1) the plurality of the donor molecules and the plurality of the organic semiconducting molecule are phase separated, (2) the organic semiconducting molecules are disposed in a hierarchical network and (3) the donor molecules occupy spaces in the hierarchical network.

22. A composition of matter, comprising an organic semiconducting molecule having an A-D'-D-D"-A structure, wherein D' is a first donor moiety, D is a second donor moiety different from D', D" is a third donor moiety different from D and D', and A is an acceptor moiety. In one or more embodiments, the organic semiconducting molecule has a HOMO in a range of −5.0 eV to −5.5 eV, a LUMO in a range of −3.8 eV to −4.3 eV, and a bandgap in a range of 1.0 eV to 1.4 eV.

In one embodiment, a series of asymmetric A-D'-D-D"-A type nonfullerene acceptors (NFAs) were designed and synthesized with the goal of optimizing light absorption and energy losses in near-infrared (NIR) organic solar cells (OSCs) principally through the use of side chain engineering. Specific molecules include p-IO1, o-IO1, p-IO2, and o-IO2 with optical bandgaps of 1.34 eV, 1.28 eV, 1.24 eV, and 1.20 eV, respectively. Manipulating the optoelectronic properties and intermolecular organization by substituting bulky phenylhexyl (p-) for linear octyl chains (o-) and replacing bisalkoxy (—O2) with alkyl-alkoxy combination (—O1) allows one to target energy bandgaps and achieve a favorable bulk heterojunction morphology when in the presence of the donor polymer PTB7-Th. Solar cells based on o-IO1 and PTB7-Th exhibit an optimal power conversion efficiency of 13.1%. The excellent photovoltaic performance obtained with the o-IO1 acceptor can be attributed to a short-circuit current of 26.3 mA cm$^{-2}$ and energy losses on the order of 0.54 eV. These results further highlight how side chain engineering is a straightforward strategy to tune the molecular design of n-type molecular semiconductors, particularly in the context of near-infrared high efficiency organic photovoltaics.

When incorporated into bulk-heterojunction photodiodes with polymer donor PTB7-Th, asymmetric NFA CO1-4F delivers a power conversion efficiency of 10.24% with a high short-circuit current density as high as ~25 mA/cm$^2$ for OSCs and a record responsivity of 0.52 A W$^{-1}$ in the NIR (920 nm) for OPDs, respectively. Analysis of film morphology reveals that processing with CN additive provides a hierarchical network of CO1-4F rich phases for efficient charge separation and transport pathways, enabling a large photocurrent generation in the devices. This work provides a simple, but effective strategy to design the molecular structure of n-type small molecule and to improve the efficiencies of NIR organic photodiodes.

Embodiments of the compositions are suitable for the fabrication of near infrared (NIR) photodetectors. When blended with a donor polymer such as PTB7-Th in a solar cell or photodetector device, high external quantum efficiency over 60% in the NIR region (600 nm to 950 nm) and solar cell power conversion efficiency over 10% were achieved. Device responsivity, detectivity, dark current, and response time were also evaluated. In one or more examples, the device includes a substrate; a transparent cathode on the substrate; one or more cathode interface layers (or electron transport layer); the active region (comprising electron donor and electron acceptor) on the cathode interface layer; one or more anode interface layers (or hole transport layer) on the absorbing region; and an anode on the anode interface layer.

BRIEF DESCRIPTION OF THE DRAWINGS

Referring now to the drawings in which like reference numbers represent corresponding parts throughout.

Figure 3:
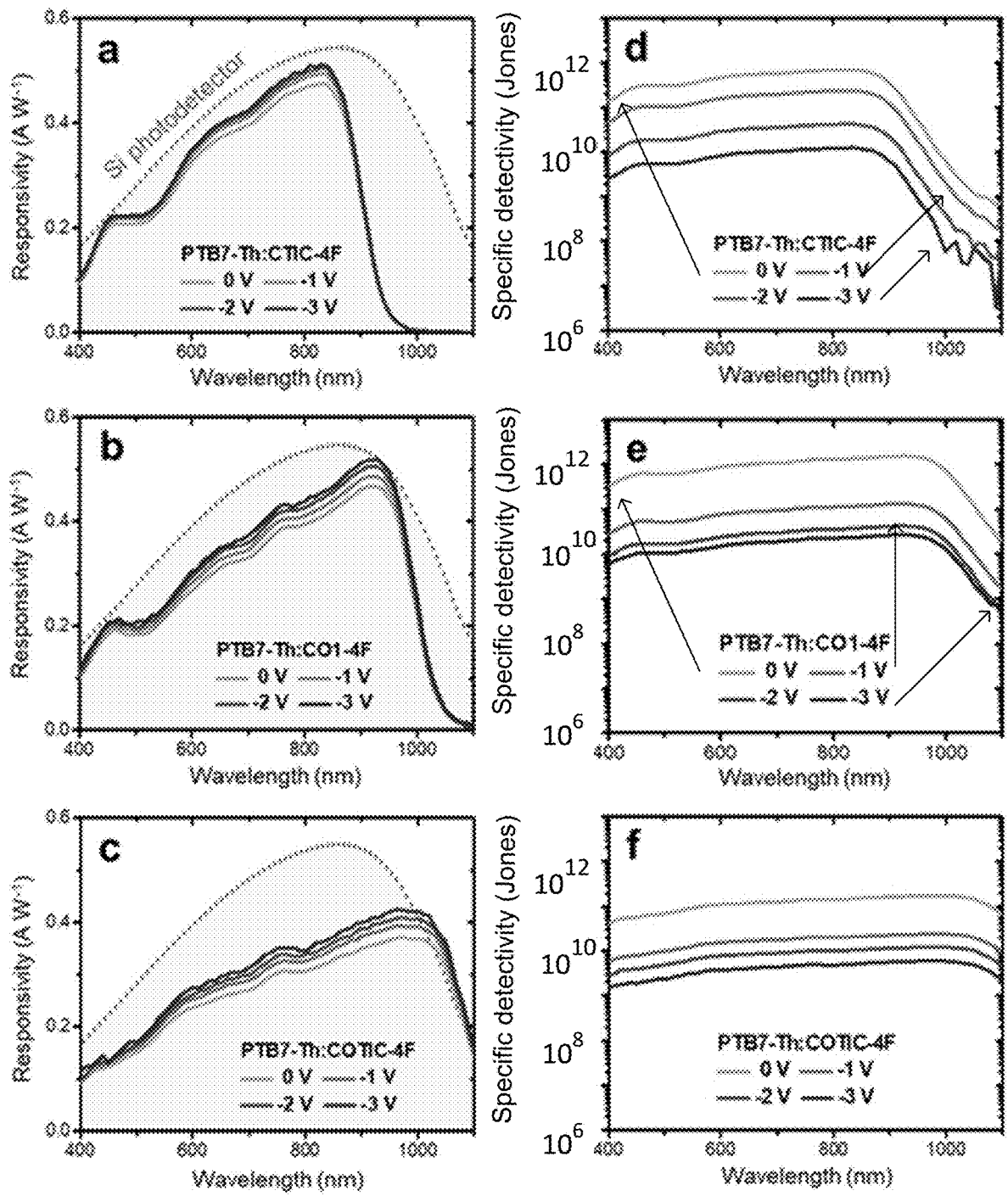
Figure 3:
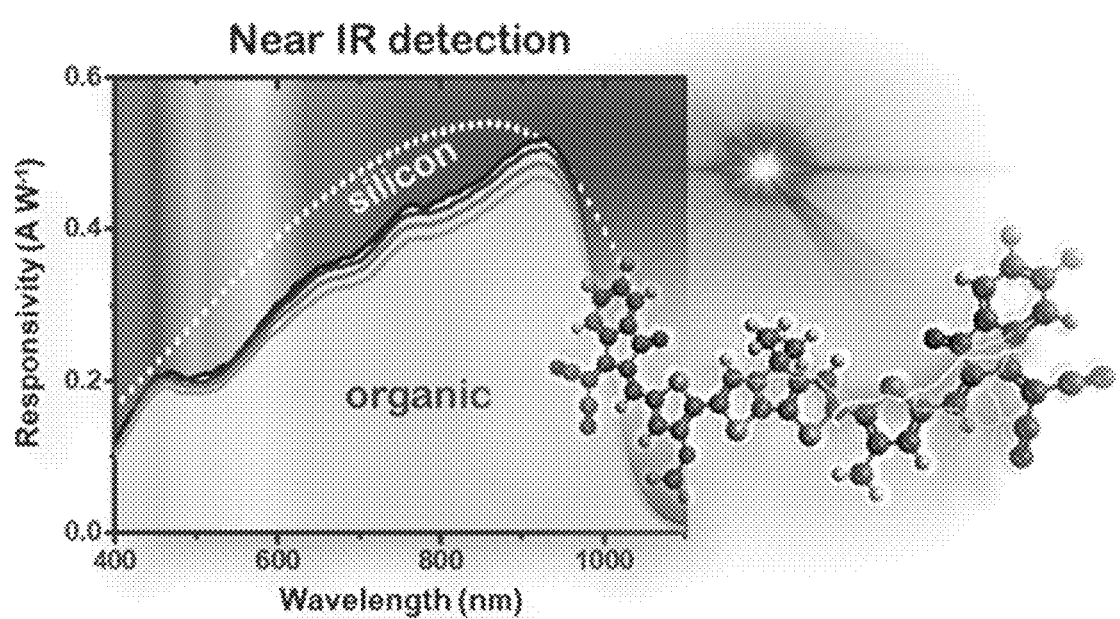

FIG. 3. (a-c) Responsivity and (d-f) specific detectivity of photodetector devices using PTB7-Th:NFA blends. (g) Comparison with silicon.

Figure 4:
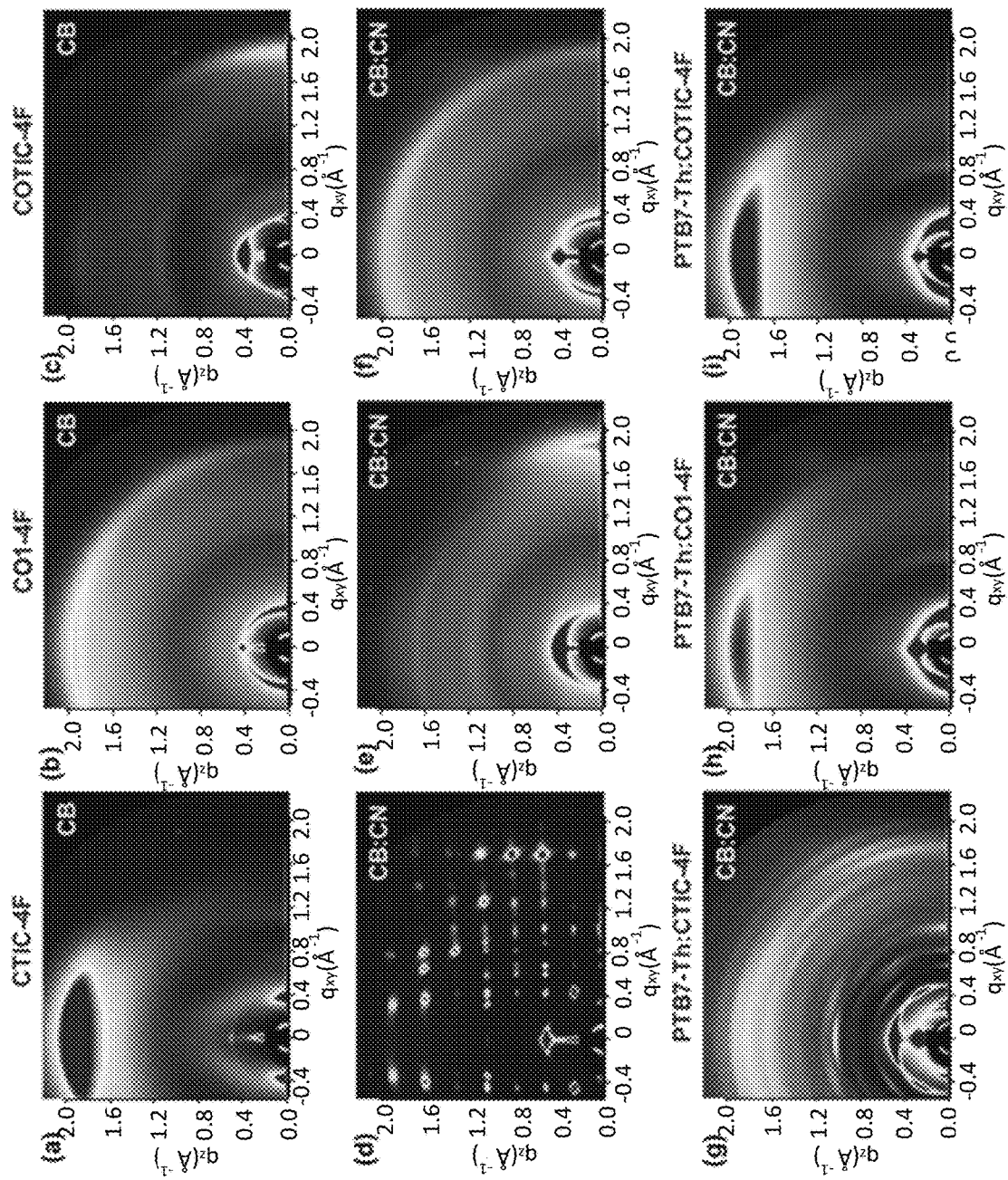

FIG. 4. 2D GIWAXS images of (a) CTIC-4F, (b) CO1-4F, and (c) COTIC-4F neat films processed with CB. 2D GIWAXS images of (d) CTIC-4F, (e) CO1-4F, and (f) COTIC-4F neat films, and (g) PTB7-Th:CTIC-4F, (h) PTB7-Th:CO1-4F, and (i) PTB7-Th:COTIC-4F blend films processed with CB:CN (98:2 vol %).

Figure 5:
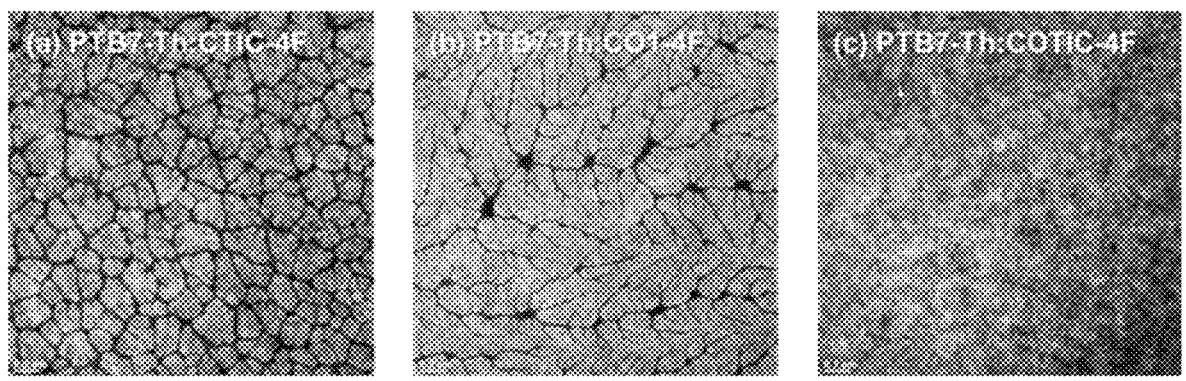

FIG. 5. TEM images of (a) PTB7-Th:CTIC-4F, (b) PTB7-Th:CO1-4F, and (c) PTB7-Th:COTIC-4F blend films processed with CB:CN (98:2 vol %).

Figure 6:
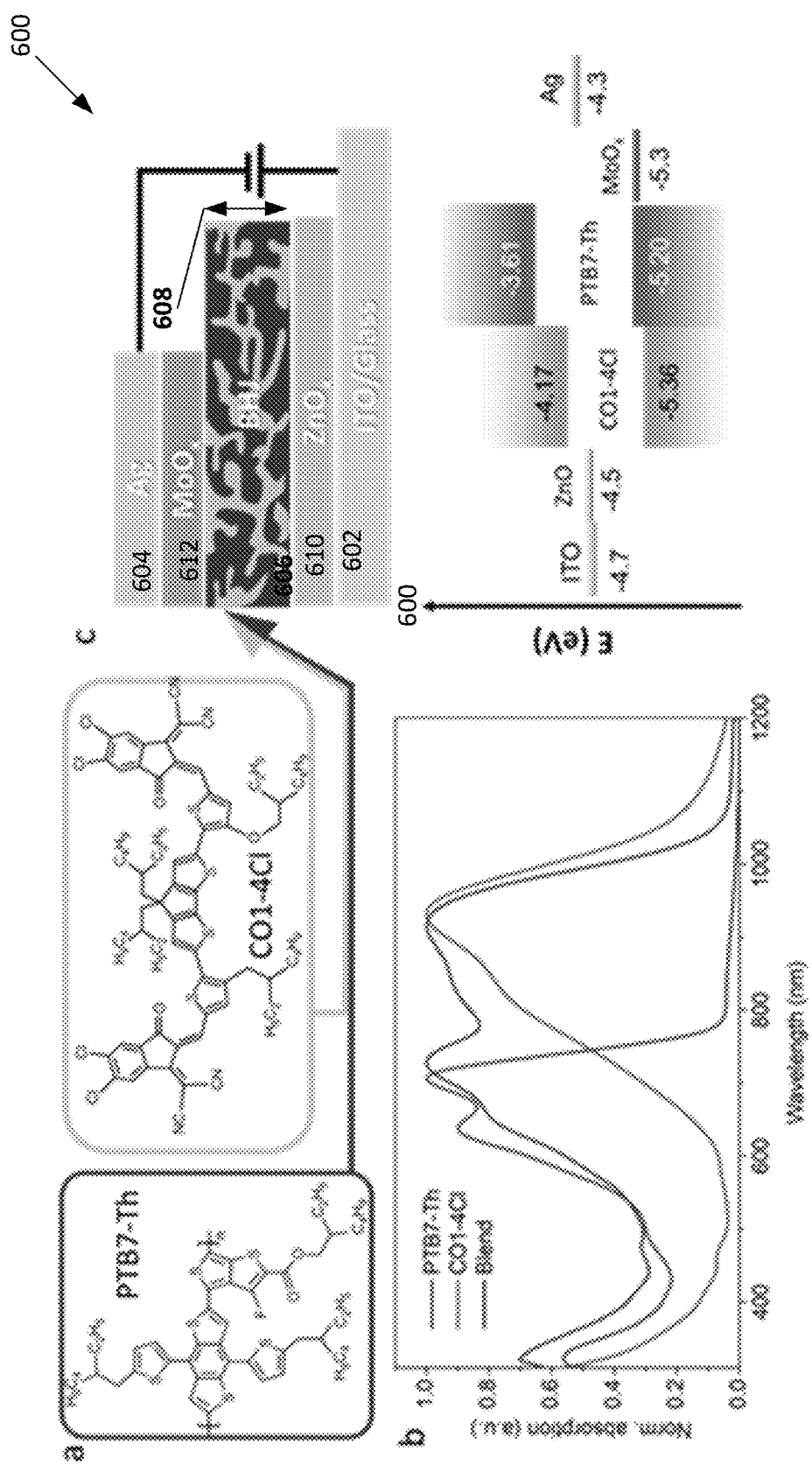

FIG. 6. (a) Chemical structures of the donor PTB7-Th and the acceptor CO1-4Cl; (b) Normalized thin film absorption of the PTB7-Th (red), CO1-4Cl (blue) and their BHJ blend (purple); (c) Device structure and energy diagram of the MR OPD. The HOMO level is derived from the thin-film cyclic voltammogram. The LUMO is calculated by the following equation: $E_{(LUMO)} = E_g^{opt} + E_{(HOMO)}$.

Figure 7:
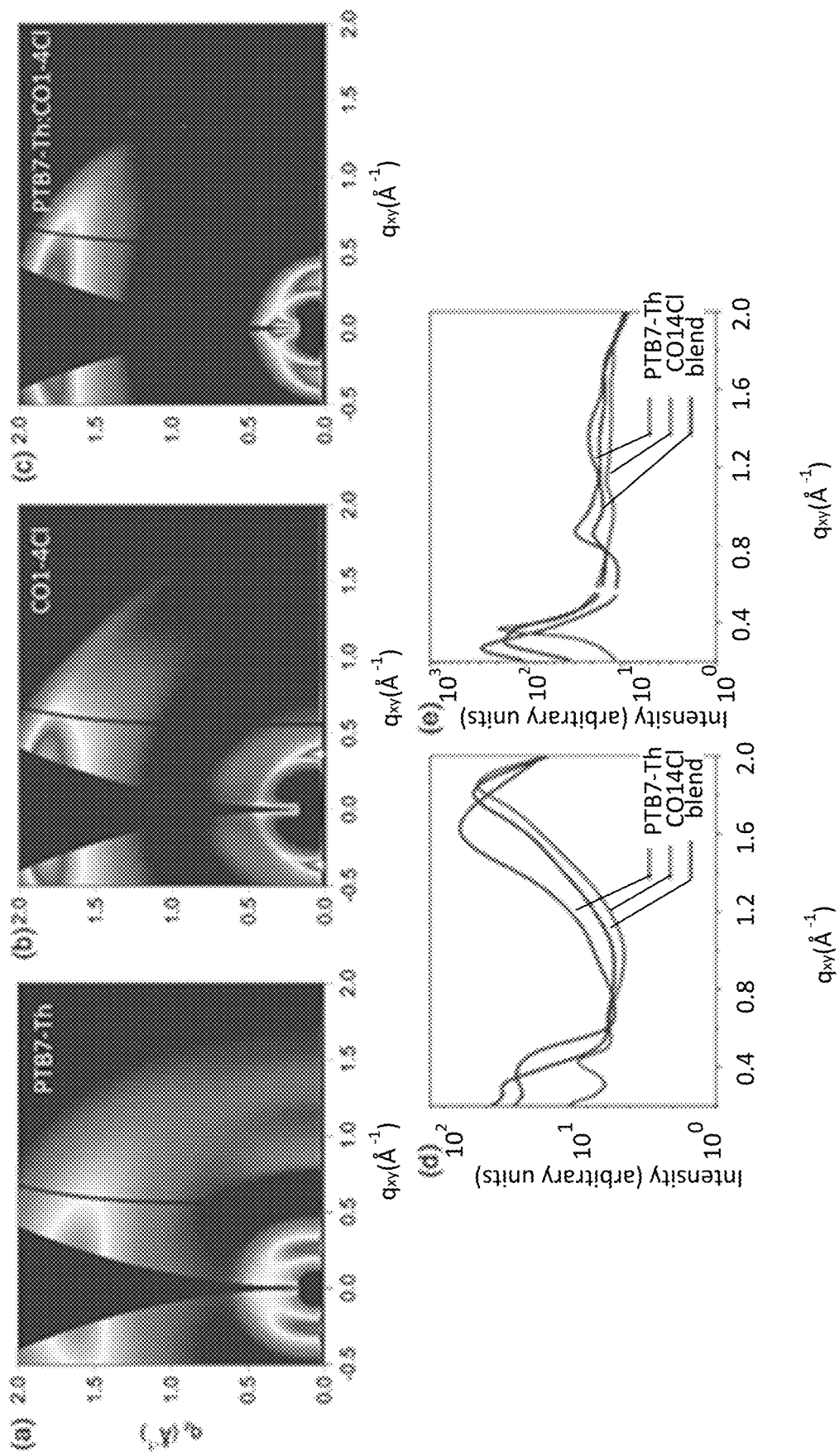

FIG. 7. 2D GIWAXS images of the films of (a) PTB7-Th, (b) CO1-4Cl and (c) the blend. (d) Out-of-plane and (e) in-plane line-cut profiles for the neat and blend films.

Figure 8:
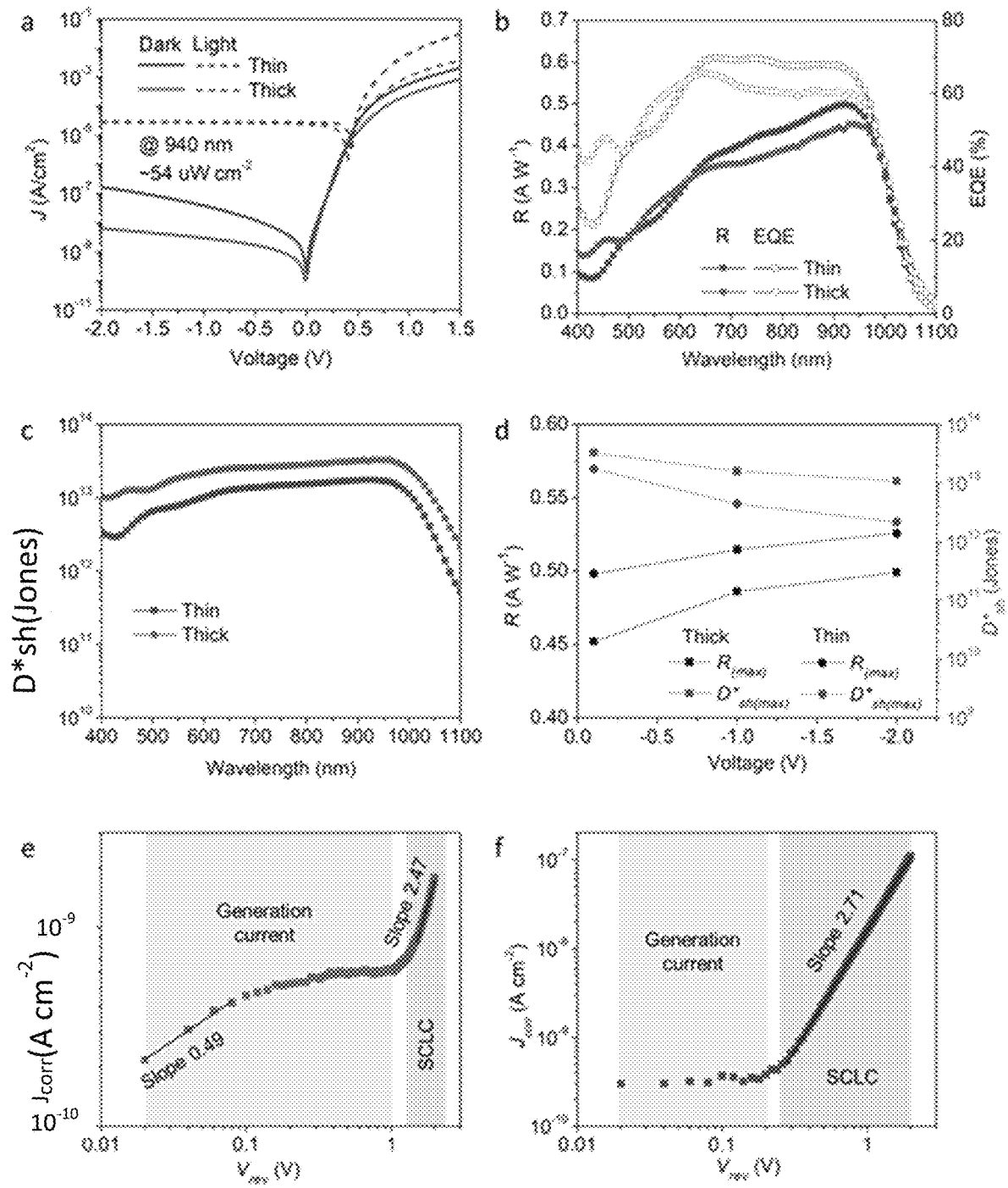

FIG. 8. (a) J-V curves of the OPDs with thin or thick active layer in the dark and under illumination of NIR. (b) Responsivity and EQE, (c) shot noise-limited specific detectivity of the OPDs at −0.1 V. (d) Bias-dependent responsivity and shot noise-limited specific detectivity of the OPDs. Corrected current density-voltage characteristics of the (e) thick device and (f) thin device under reverse bias.

Figure 9:
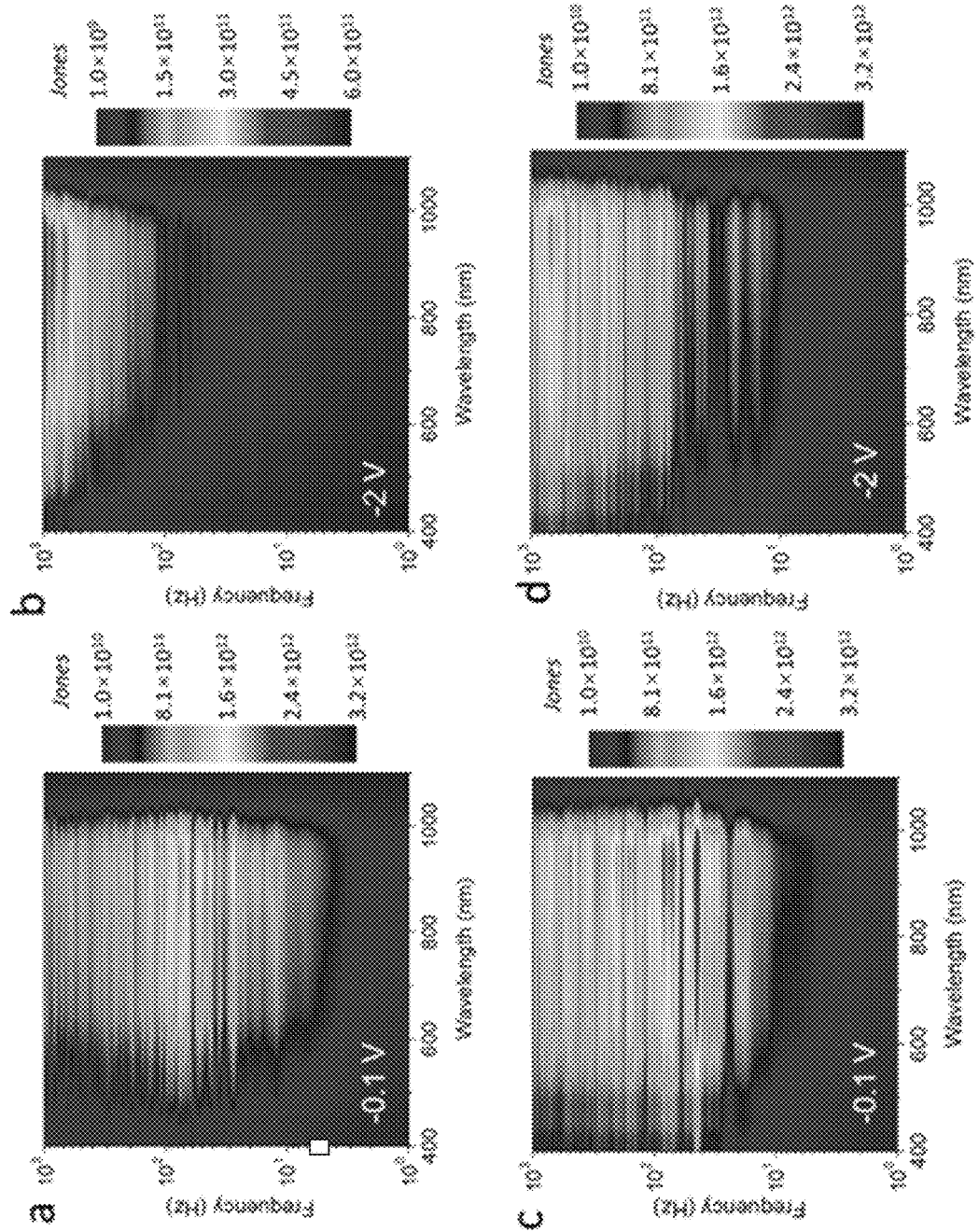

FIG. 9. Specific detectivity (D*) as a function of frequency and incident light wavelength for the thin device at (a) −0.1 V and (b) −2 V, and for the thick device at (c) −0.1 V and (d) −2 V.

Figure 10:
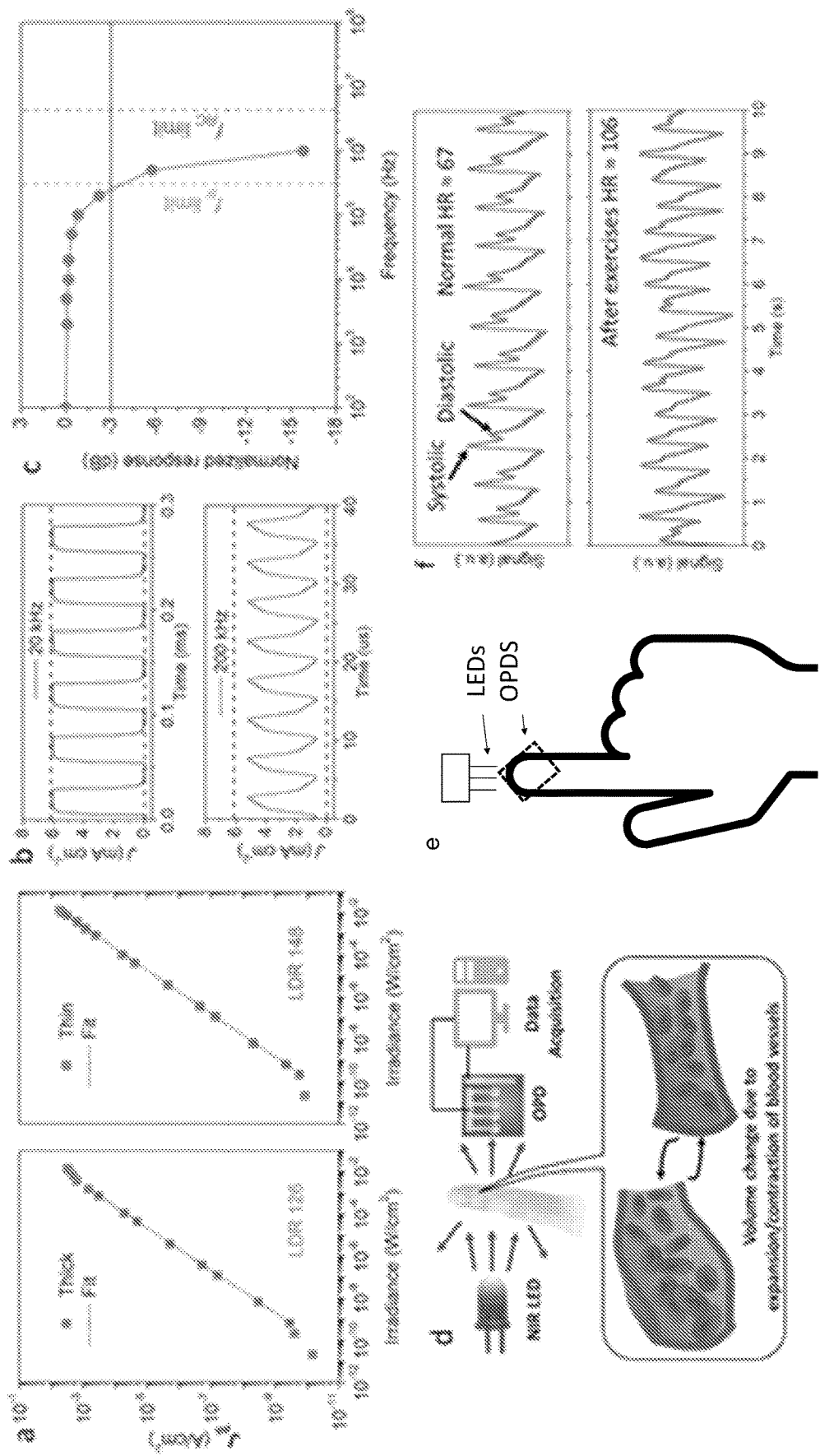
Figure 10:
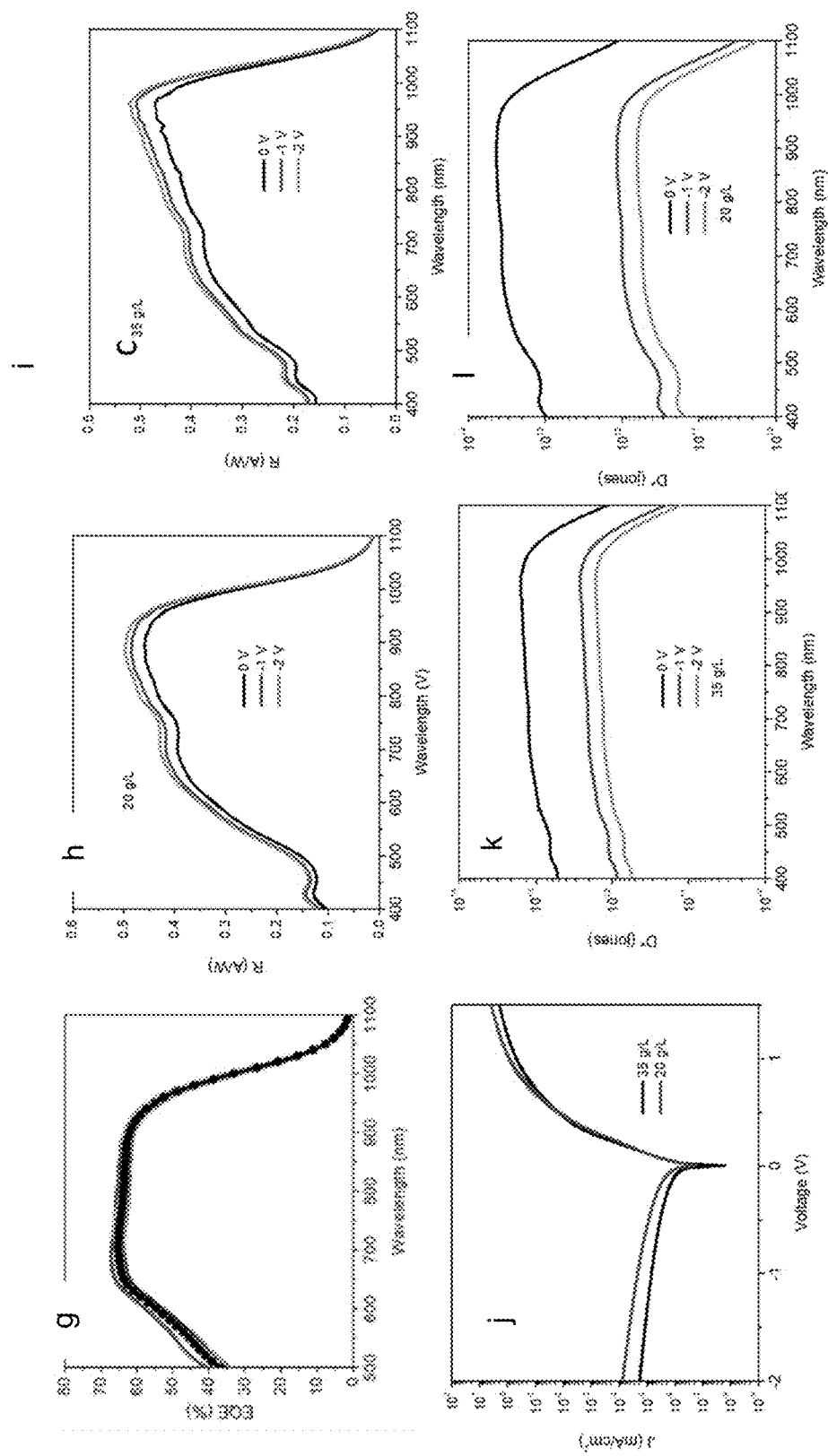

FIG. 10. (a) Linear dynamic range of the OPDs under illumination of 940 nm LEDs at −0.1 V. (b) Phototransient response of the thick device under light modulation frequency of 20 kHz (red) and 200 kHz (blue) at −2 V. (c) Normalized response as a function of frequency. The dashed lines indicate the theoretical cutoff frequency limited by transit time (green) and RC time constant (red). (d) Working principle of NIR photoplethysmography. (e) Set-ups of HR measurement using the OPD. (f) Pulse signal measured from the OPD at normal (upper) and after-exercise (lower) conditions; further data shown in (g) EQE, (h-i) Responsivity, (j) dark current, and (k-l) specific detectivity of photodetector devices using PTB7-Th:CO1-4Cl blends. Device processing condition for g-l is 1000 rpm for 20 g/L and 35 g/L solution in CB with 2 v % CN. The D-A ratio is 1:1.5. The calculated D* is the shot noise-limited specific detectivity.

Figure 11:
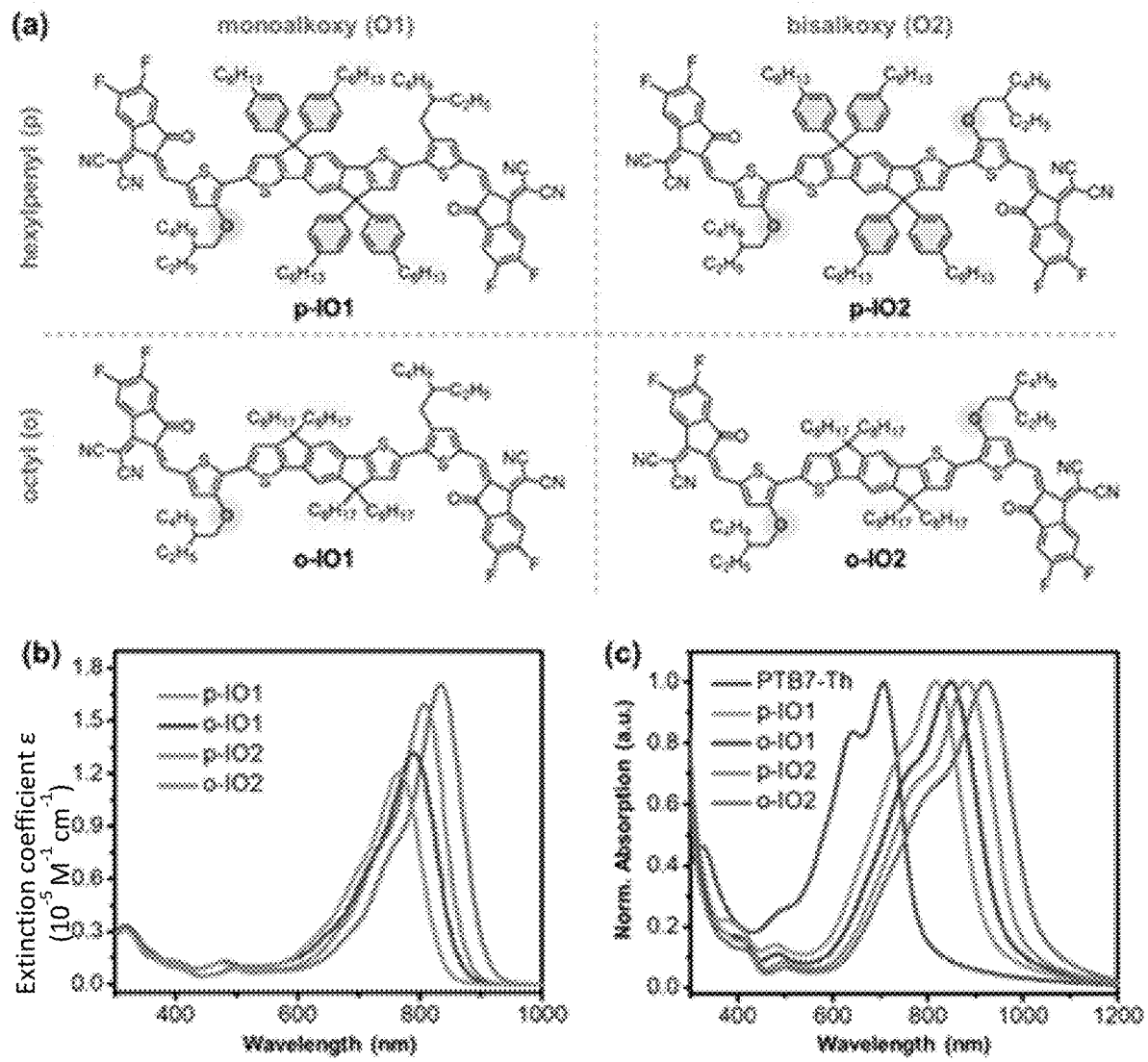

FIG. 11. (a) Molecular structures of p-IO1, o-IO1, p-IO2, and o-IO2. Absorption spectra of (b) solution in chloroform and (c) thin films.

Figure 12:
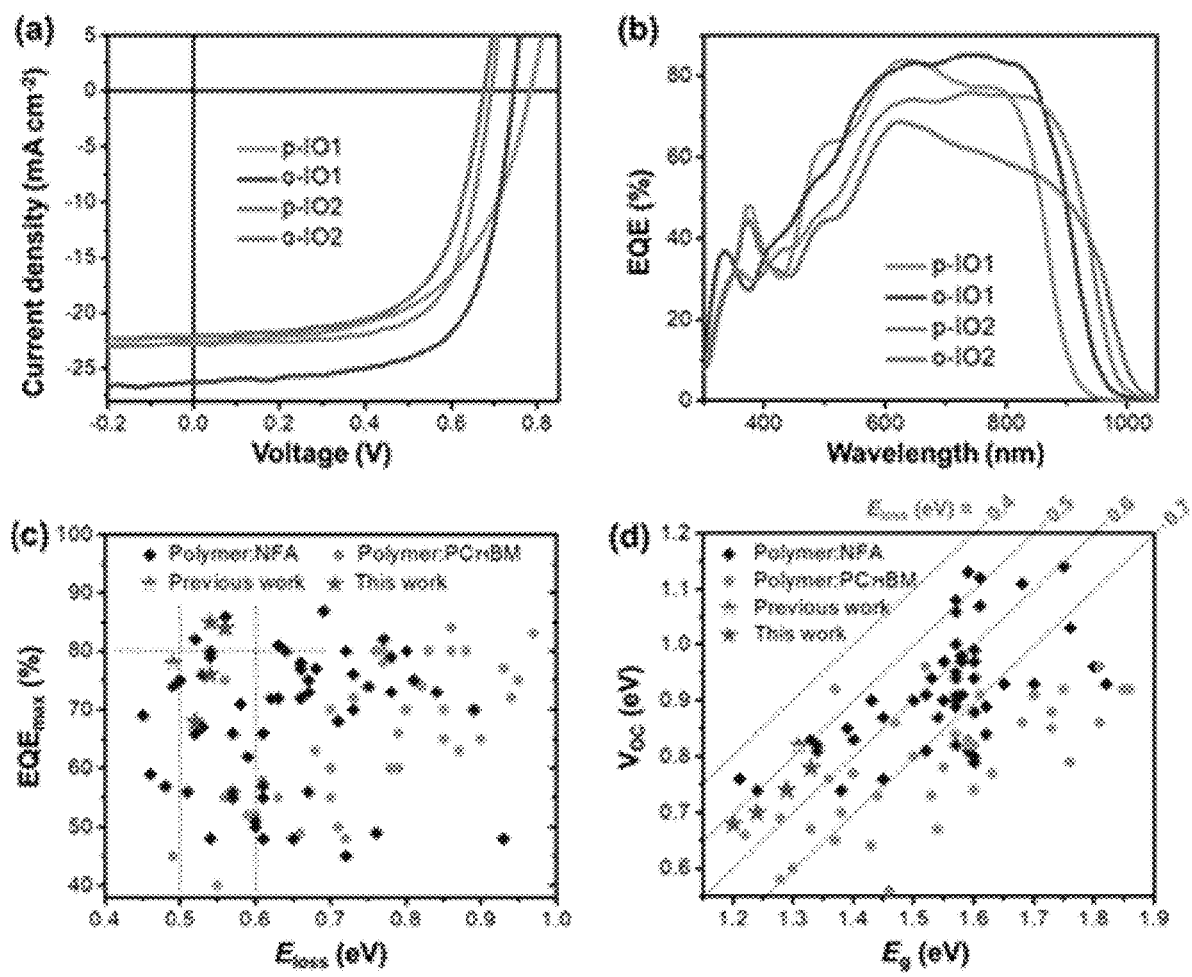
Figure 12:
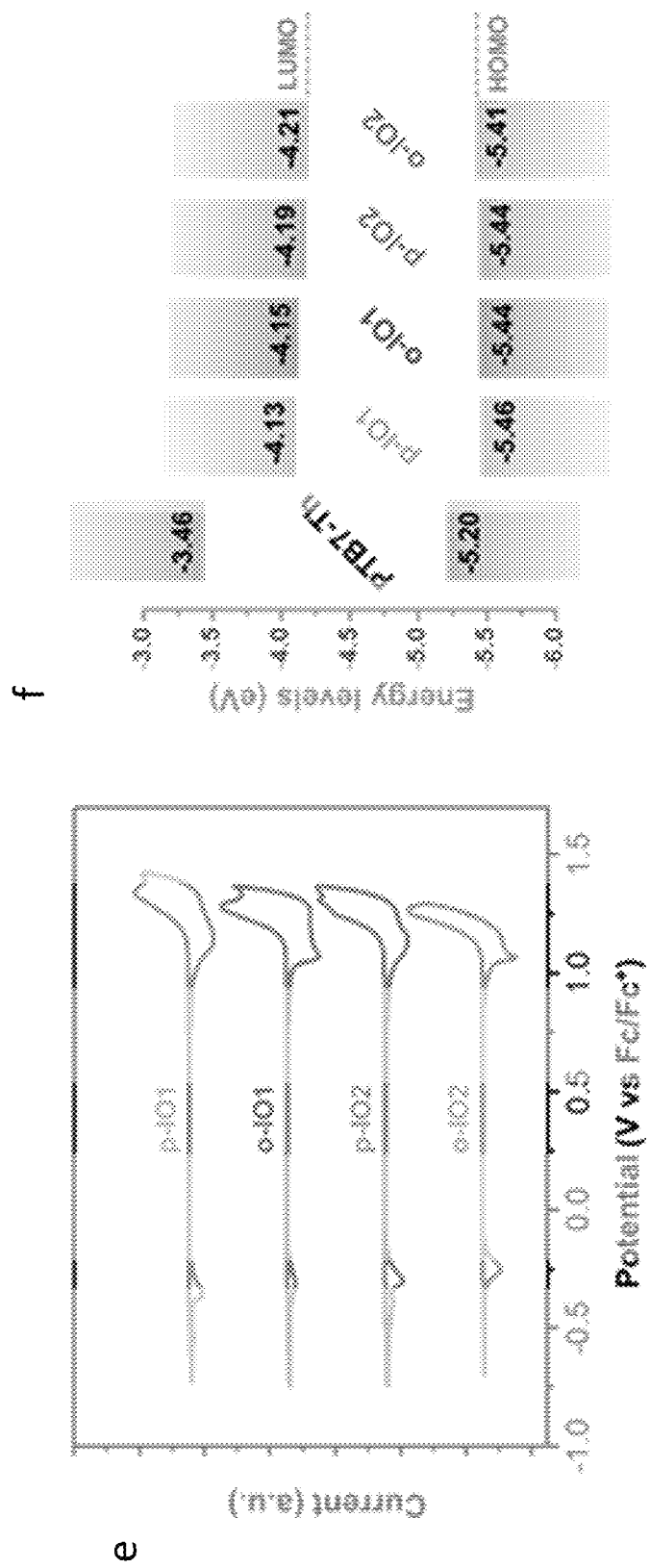
Figure 12:
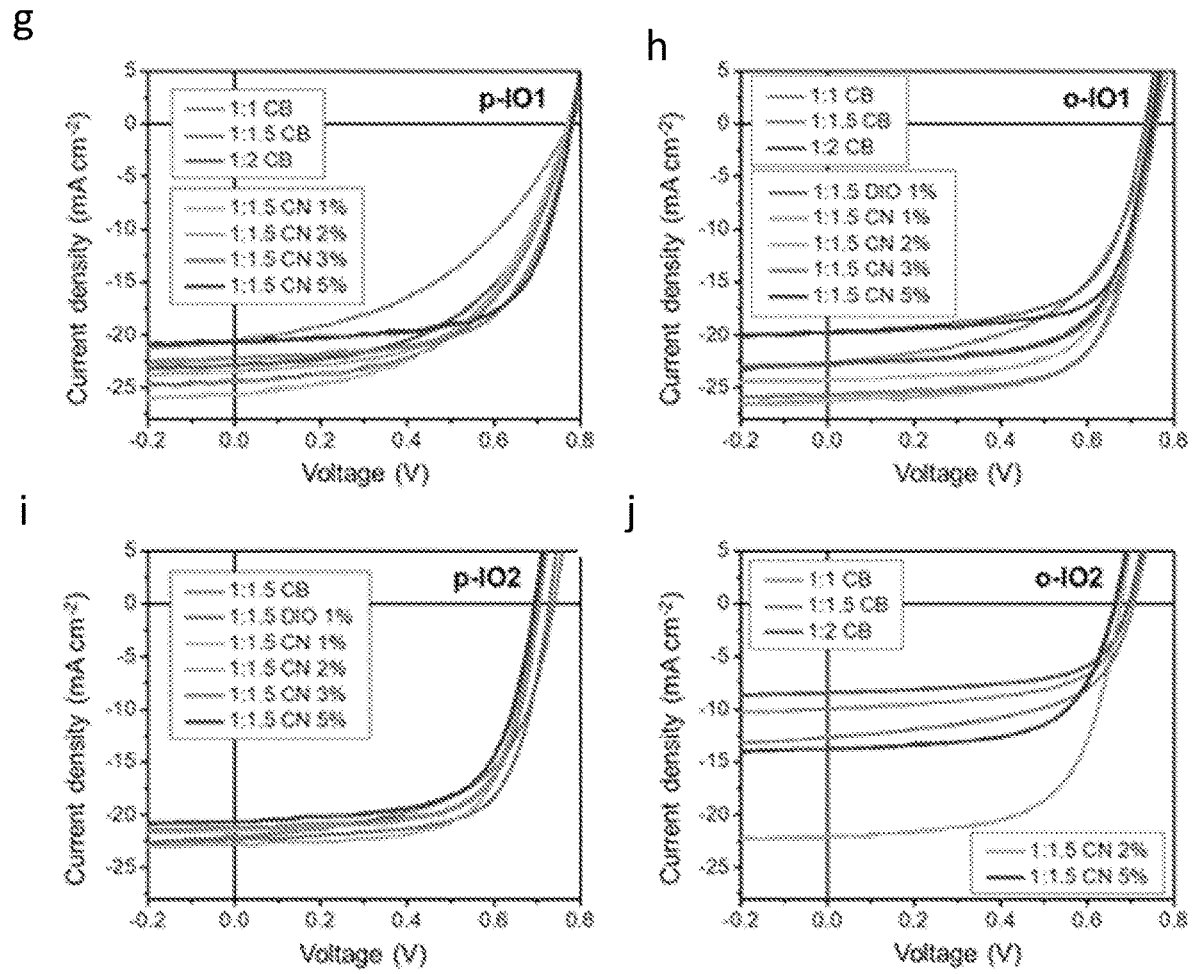

FIG. 12. (a) J-V characteristics and (b) EQE spectra of the optimized solar cell devices under AM 1.5 G illumination at 100 mW cm$^{-2}$. Plots of (c) $E_{loss}$ against $EQE_{max}$ and (d) $E_g$ against $V_{OC}$ in various OSCs with fullerene or nonfullerene acceptors; (e) Cyclic voltammograms; (f) energy diagram of photoactive materials and detailed J-V characteristics curves of (g) p-IO1, (h) o-IO1, (i) p-IO2, and (j) o-IO2-based devices.

Figure 13:
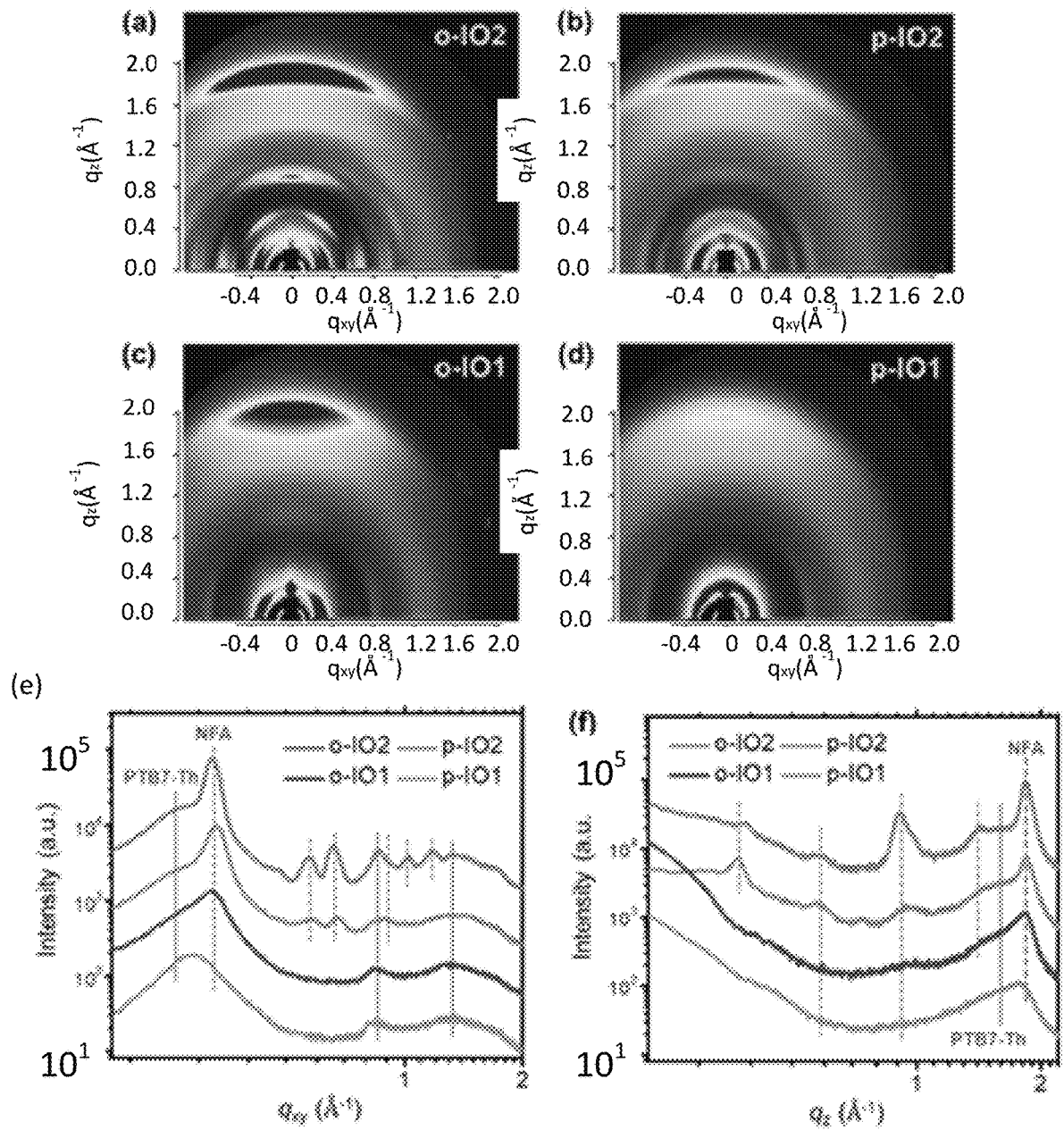
Figure 13:
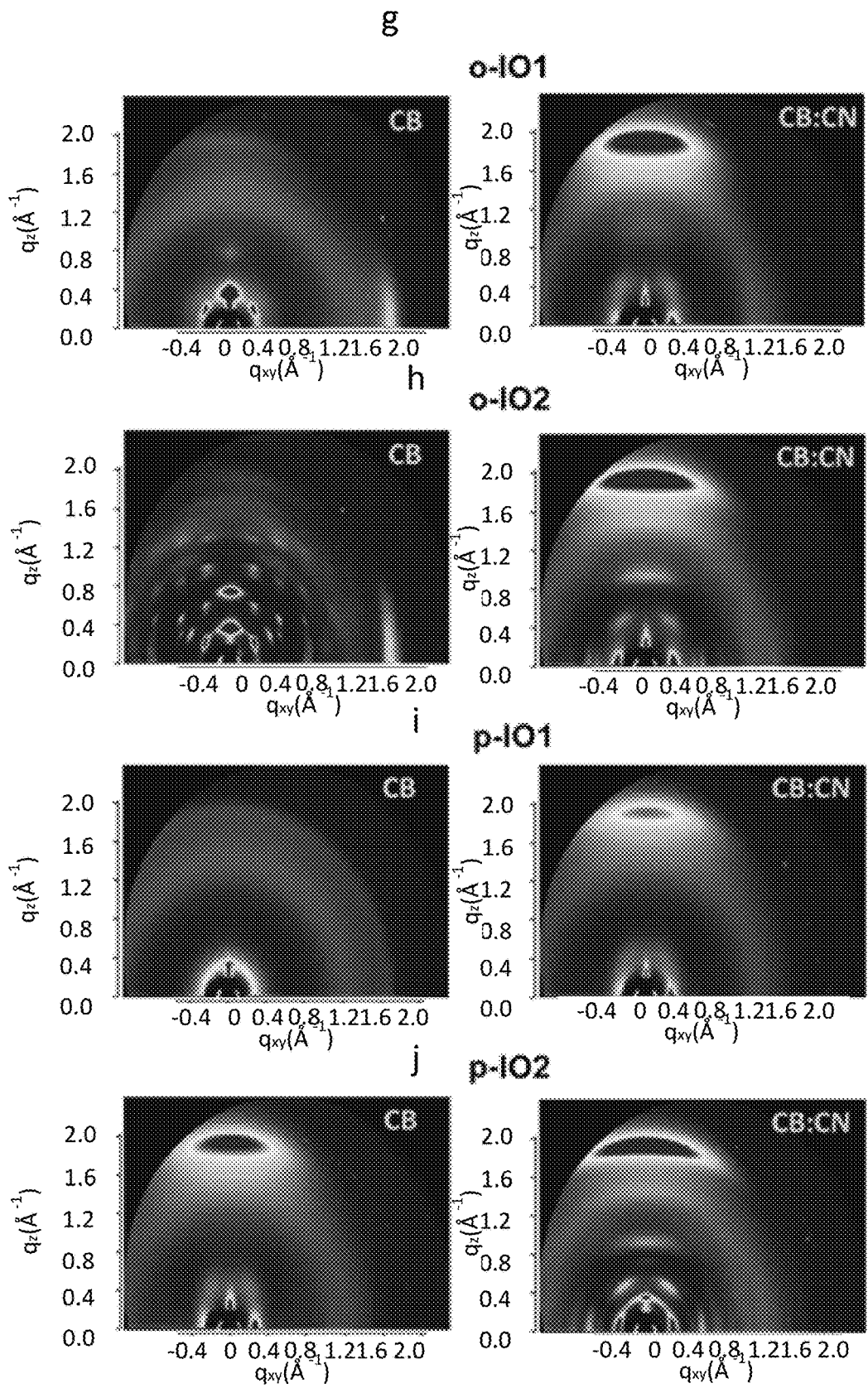

FIG. 13. 2D GIWAXS images of (a) PTB7-Thio-IO2, (b) PTB7-Th:p-IO2, (c) PTB7-Th:o-IO1, and (d) PTB7-Th:p-IO1 blend films. (e) In-plane and (f) out-of-plane line-cut profiles; solid lines and dotted lines indicate PTB7-Th and NFAs, respectively; (g)-(j) 2D GIWAXS images of p-IO1, o-IO1, p-IO2, and o-IO2 neat films processed by CB (left) and CB:CN (right), respectively.

Figure 14:
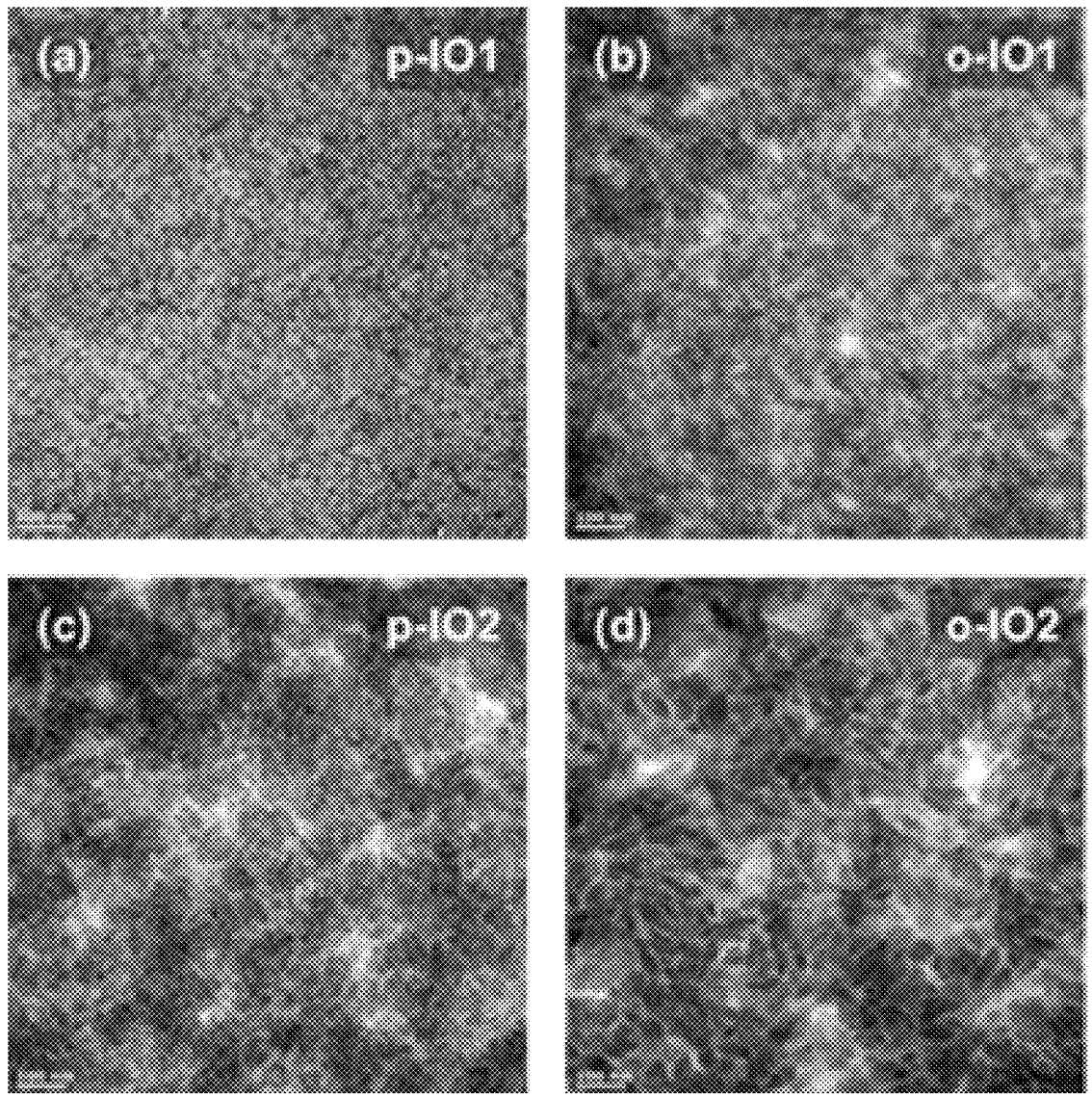
Figure 14:
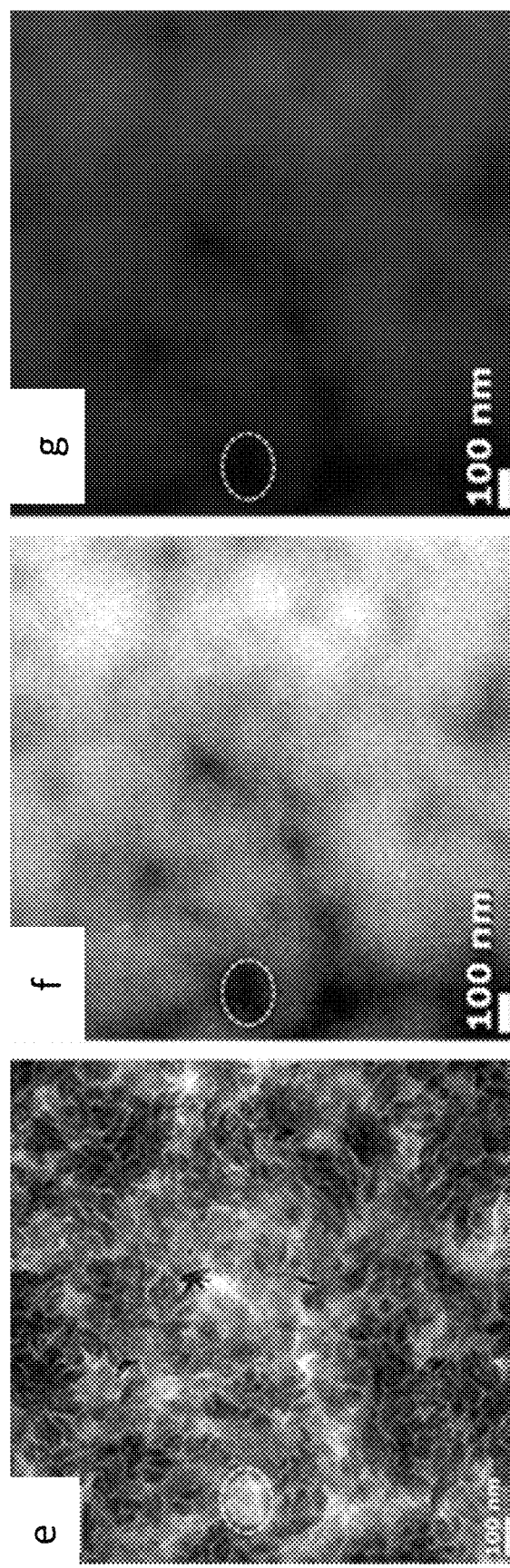

FIG. 14. TEM images of (a) PTB7-Th:p-IO1, (b) PTB7-Th:o-IO1, (c) PTB7-Th:p-IO2, and (d) PTB7-Th:o-IO2 blend films processed with CB:CN. (e) TEM images and (f, g) electron energy loss spectroscopy of the PTB7-Th:o-IO2 blend film. In the EELS, nitrogen atomic mapped regions (red color) indicate the acceptor-dominant aggregates in the film. Yellow dotted circles mark the same position.

Figure 15:
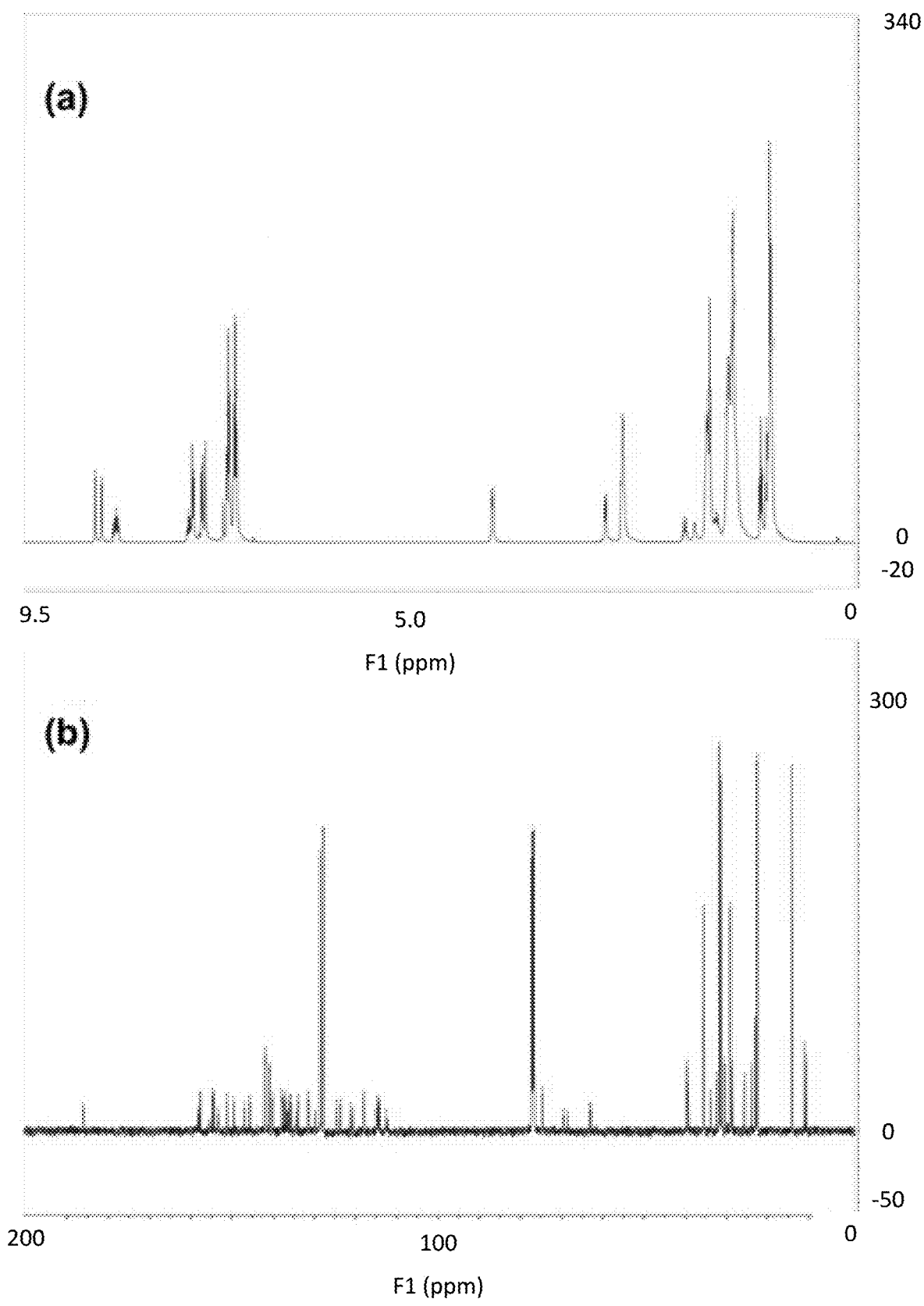

FIG. 15. (a) $^1$H NMR and (b) $^{13}$C NMR spectra of compound p-IO1.

Figure 16:
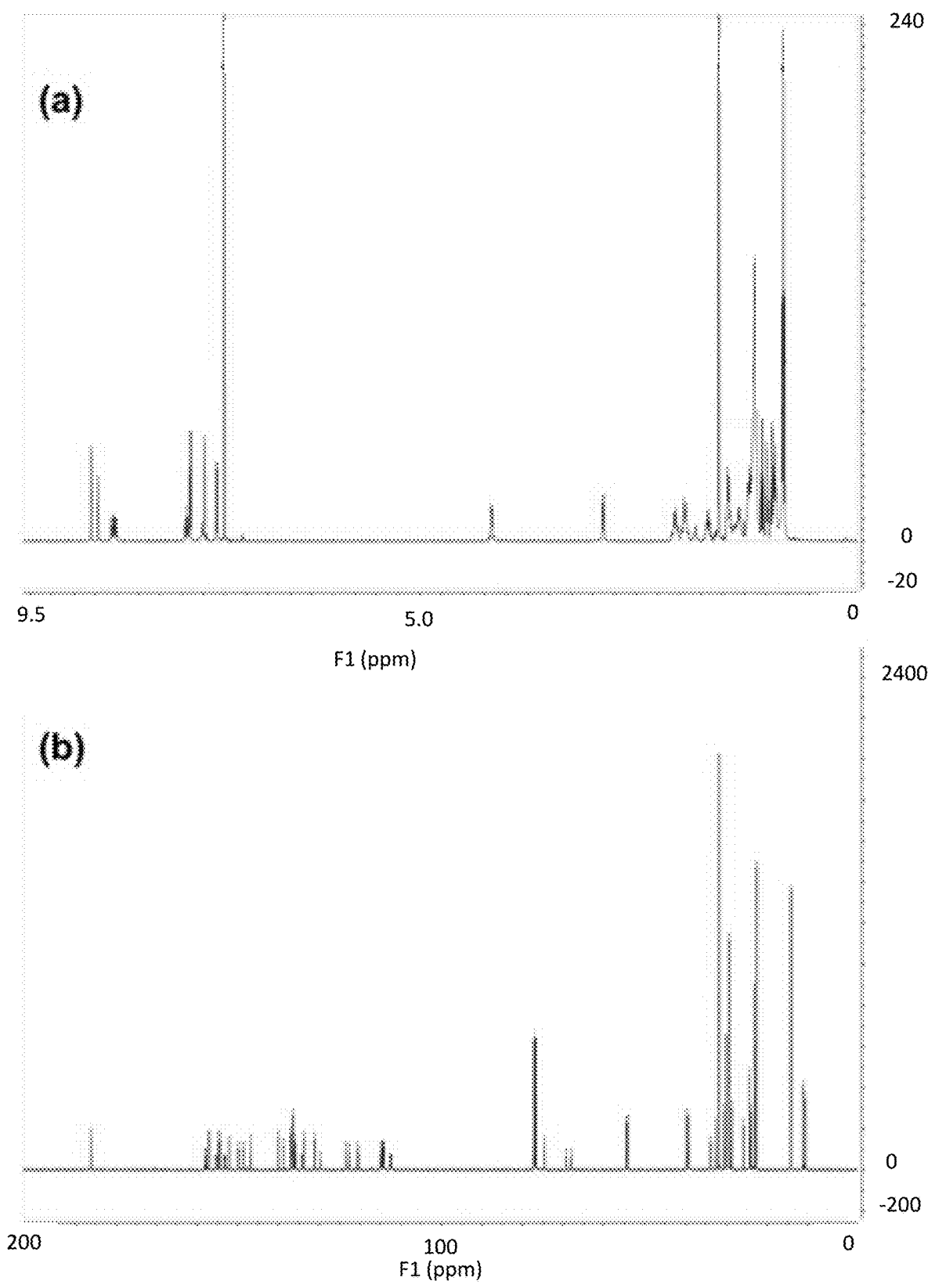

FIG. 16. (a) $^1$H NMR and (b) $^{13}$C NMR spectra of o-IO1.

Figure 17:
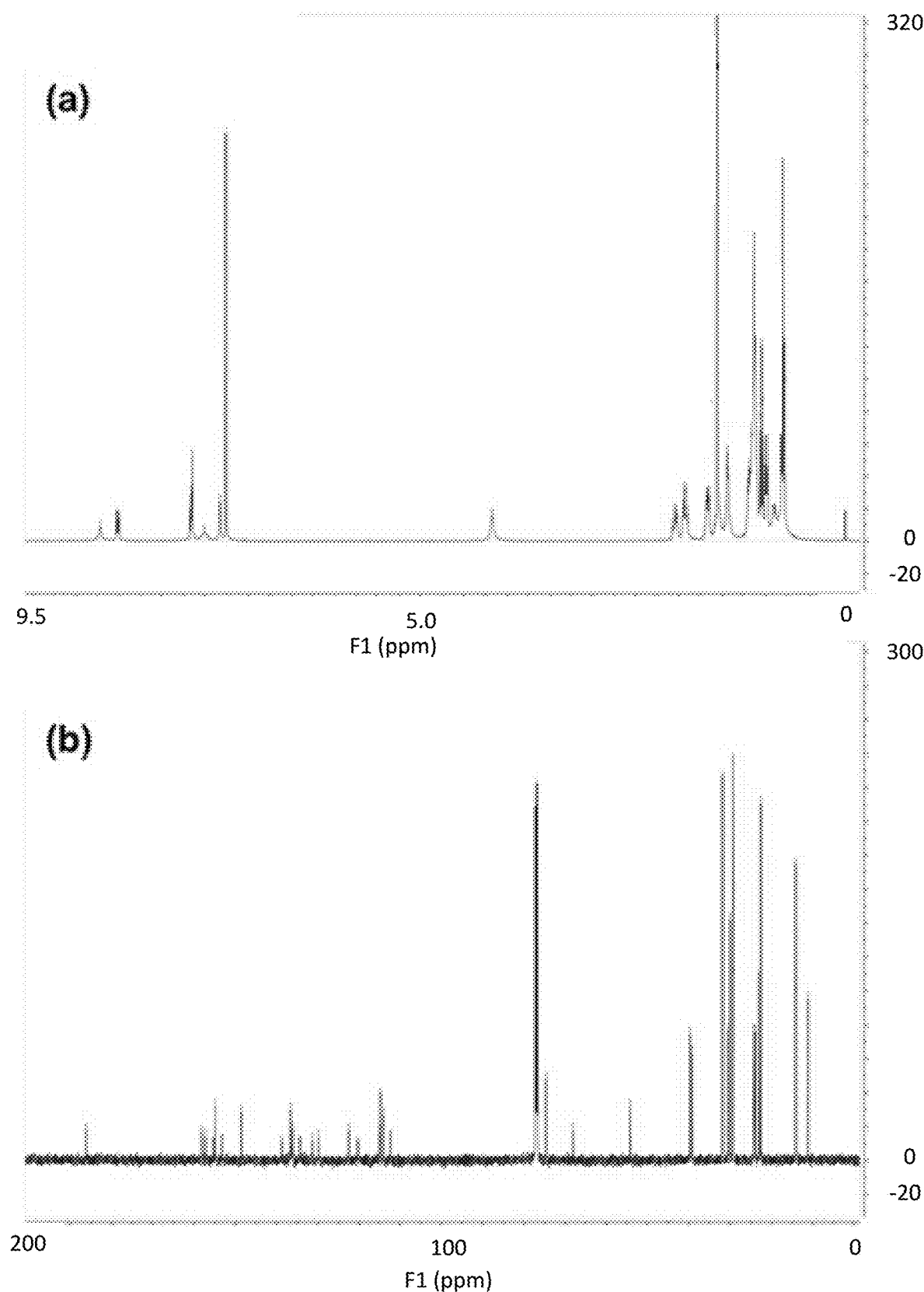

FIG. 17. (a) $^1$H NMR and (b) $^{13}$C NMR spectra of o-IO2.

Figure 18:
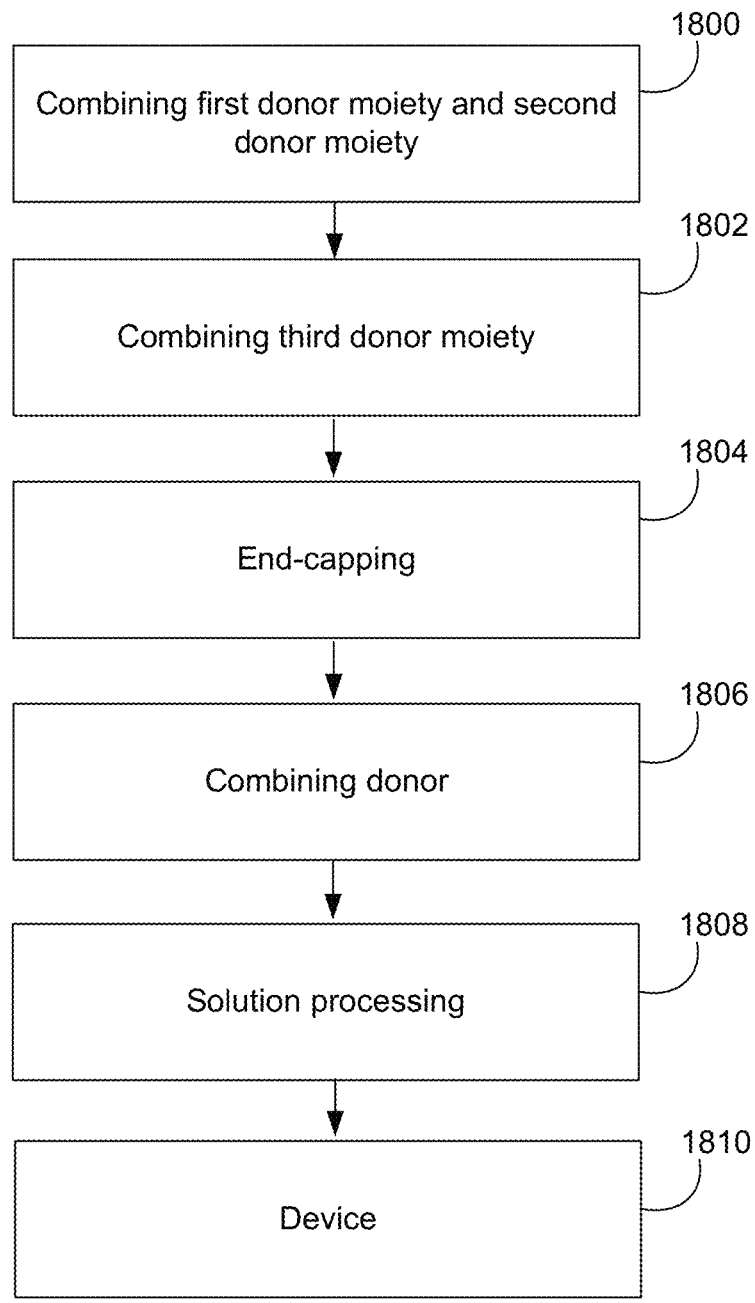
Figure 19B:
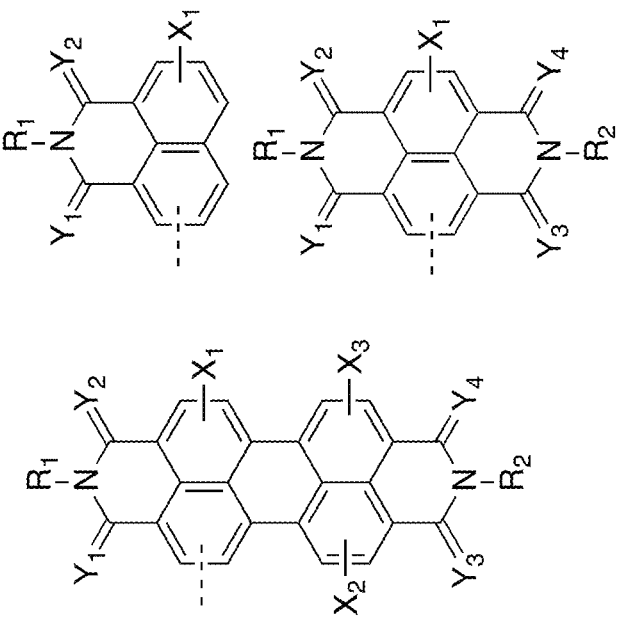
Figure 19A:
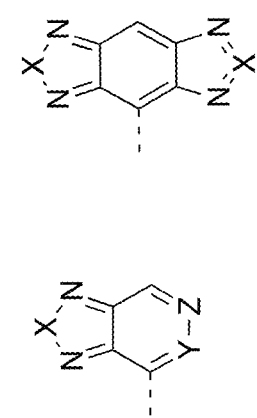
Figure 19C:
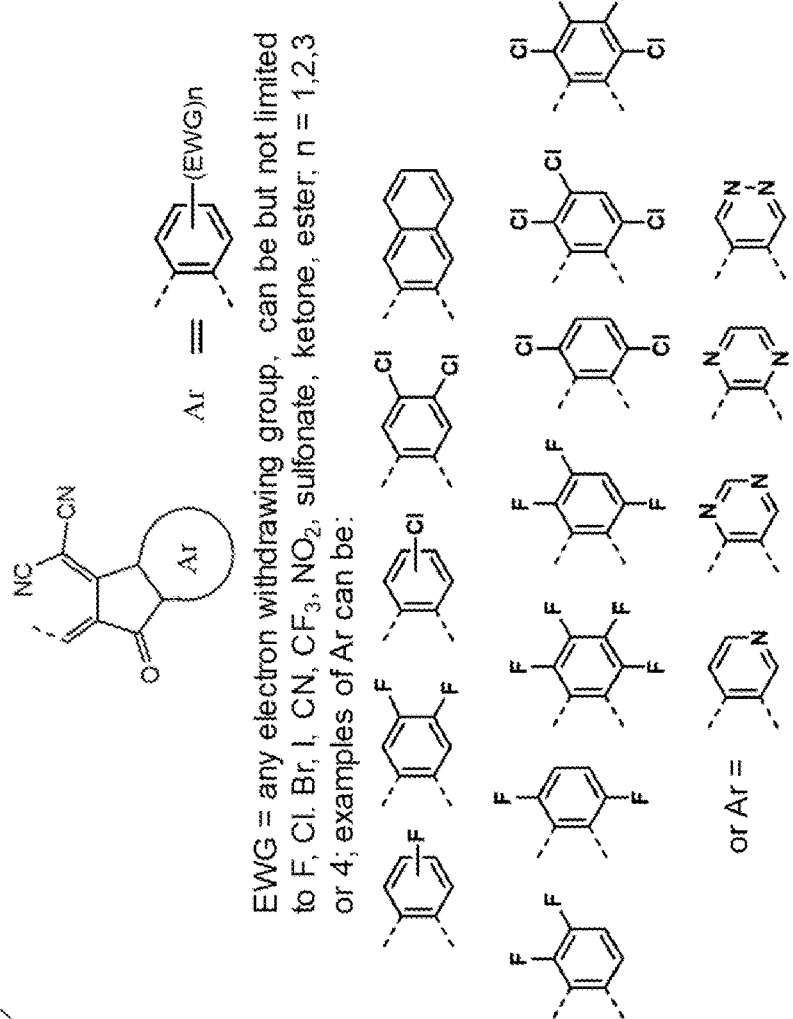
Figure 19C:
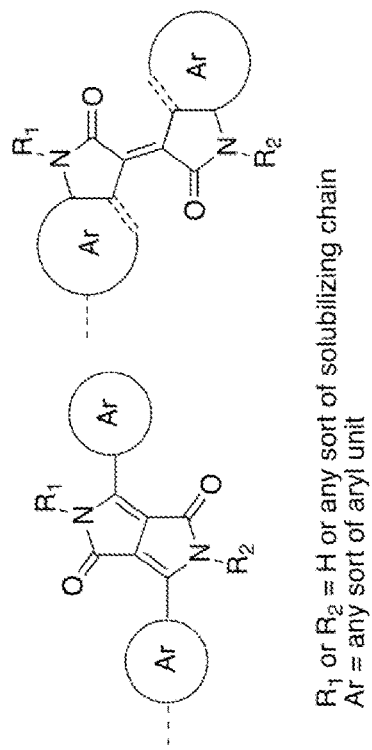
Figure 19D:
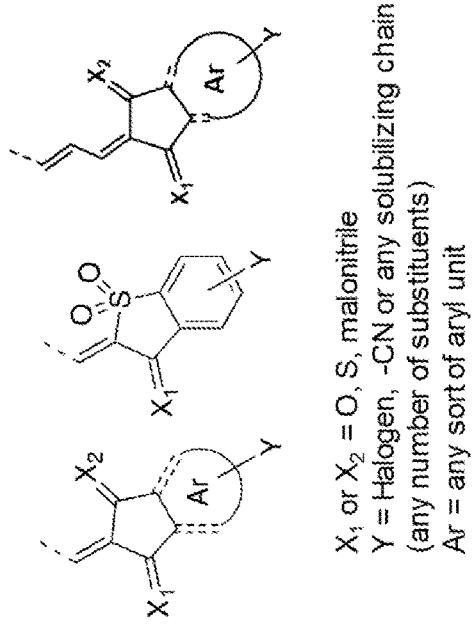
Figure 19F:
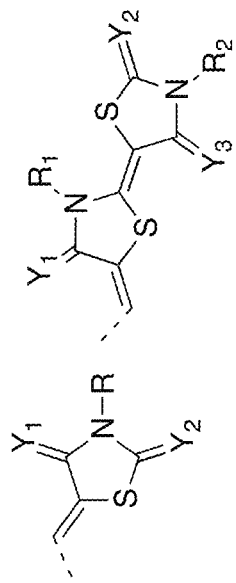
Figure 19F:
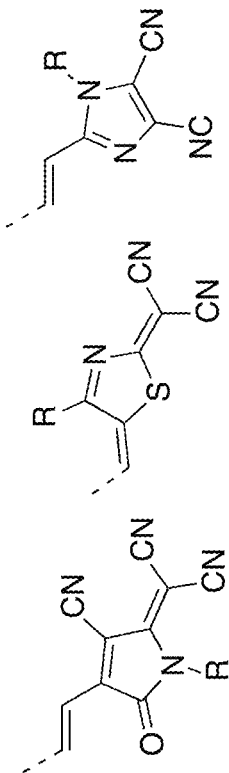
Figure 19F:
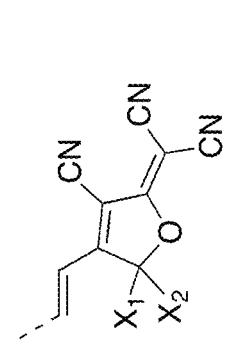
Figure 19F:
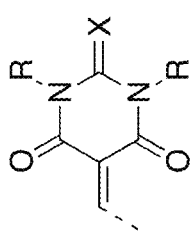
Figure 19G:
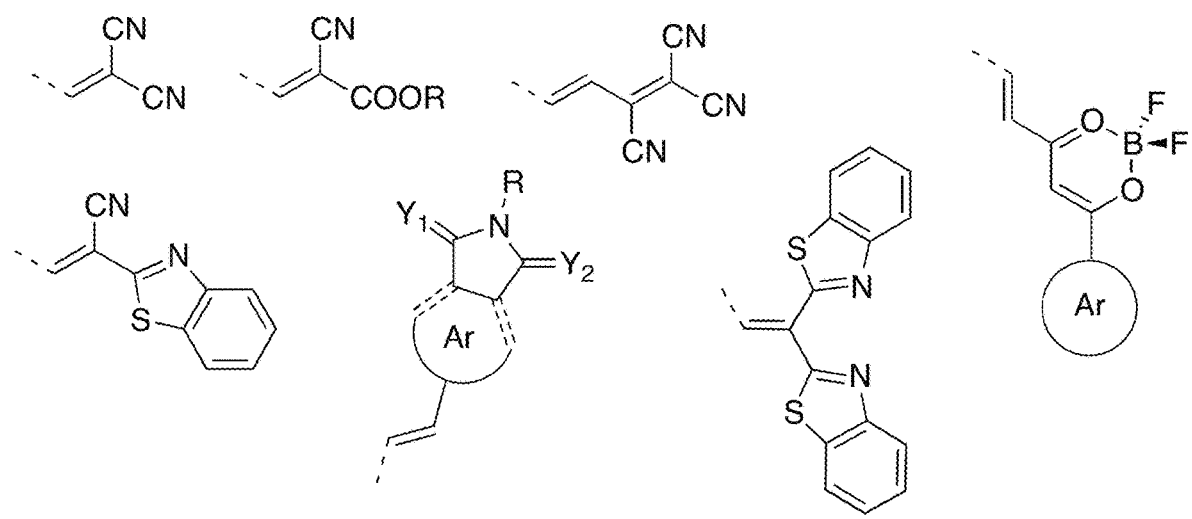
Figure 19G:
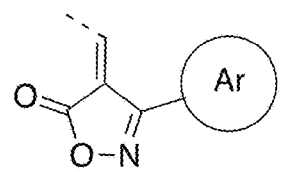
Figure 19H:
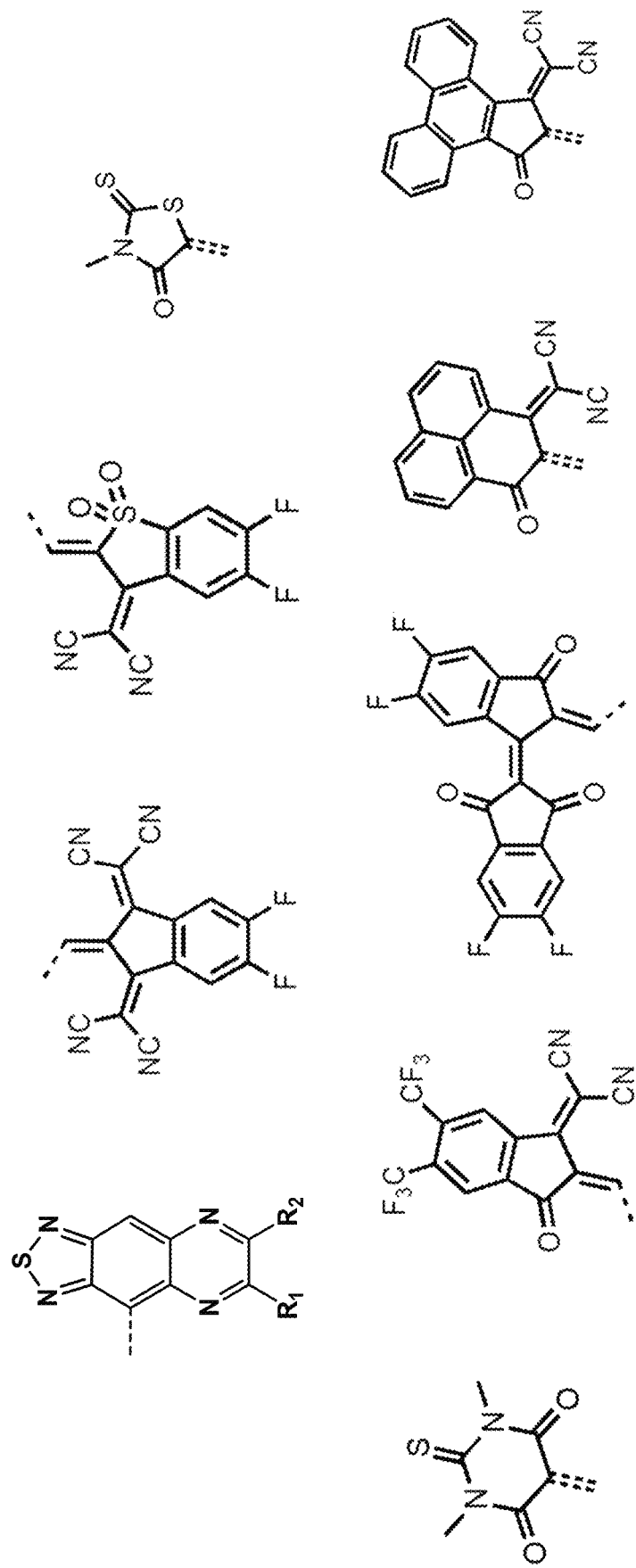
Figure 20A:
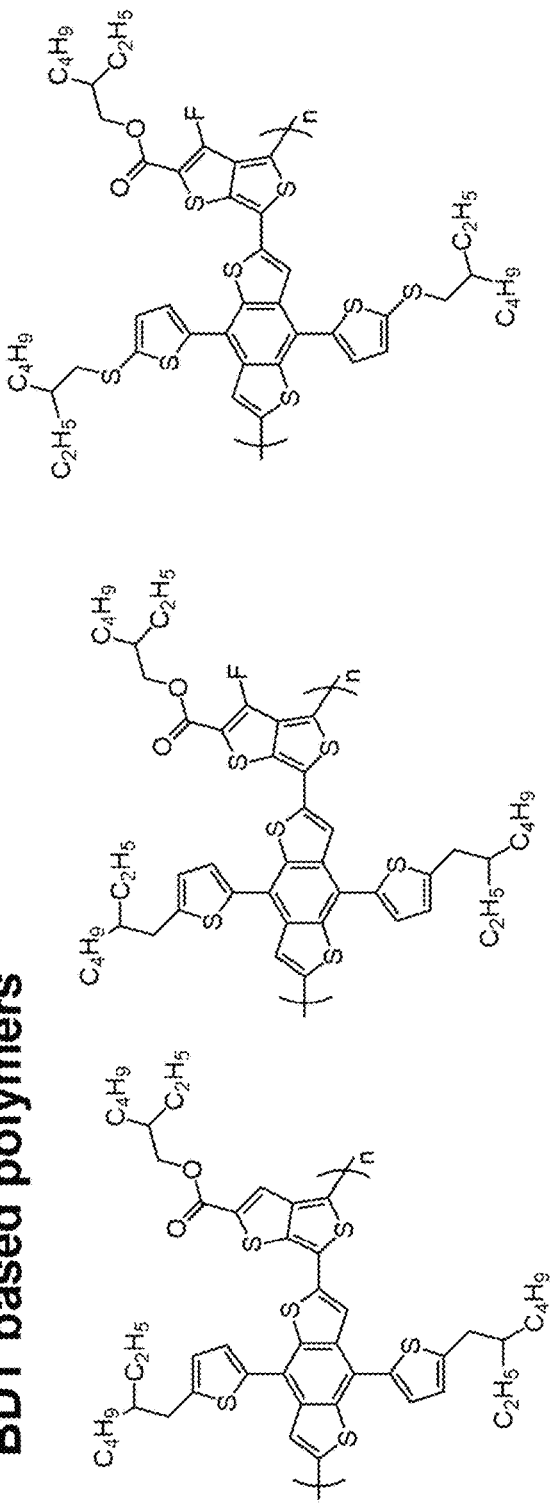
Figure 20A:
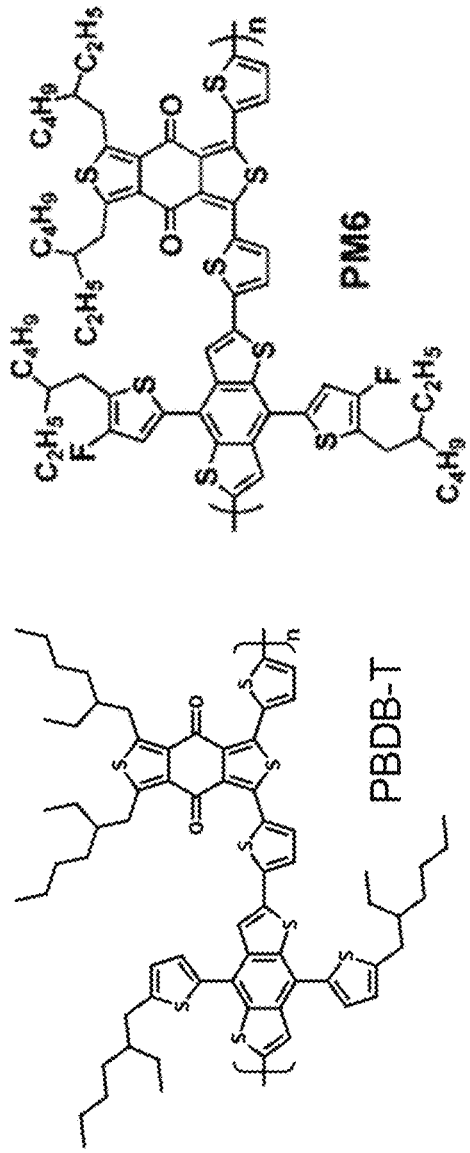
Figure 20B:
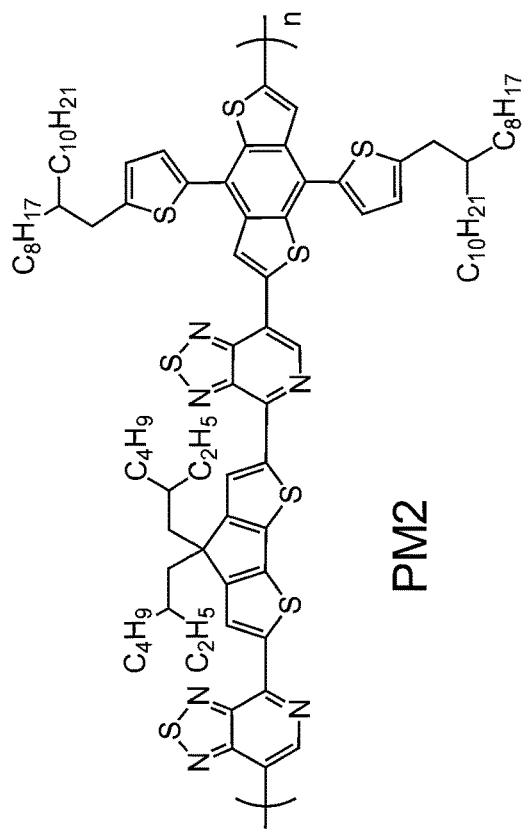
Figure 20B:
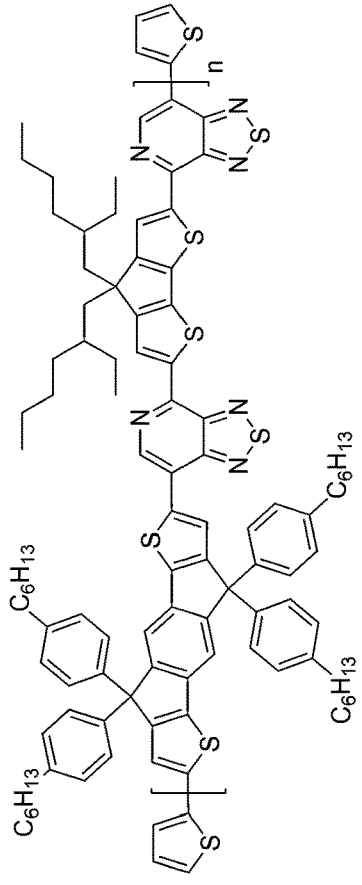
Figure 20B:
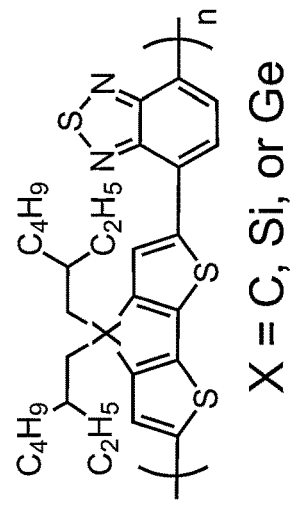
Figure 20C:
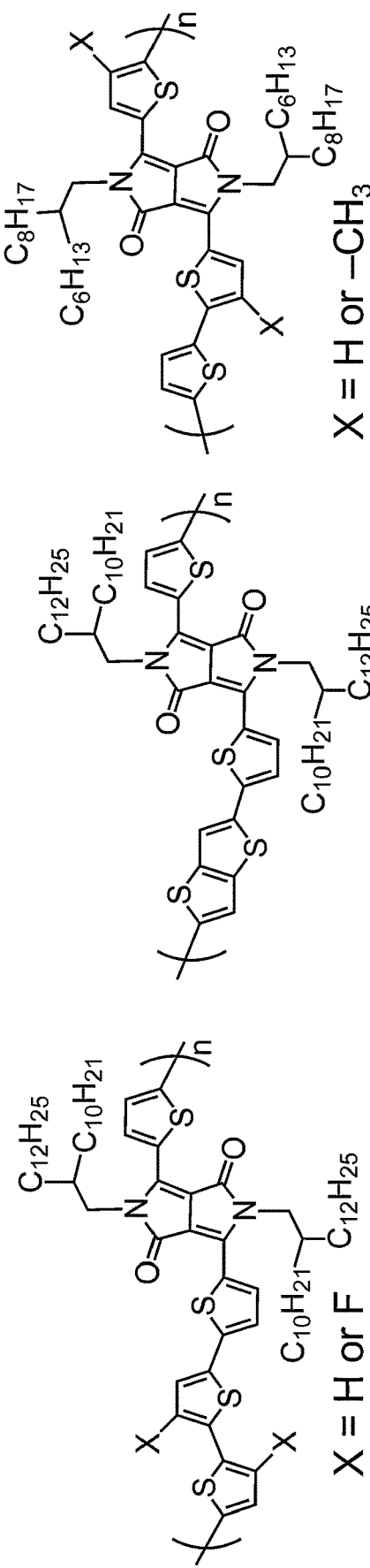
Figure 20D:
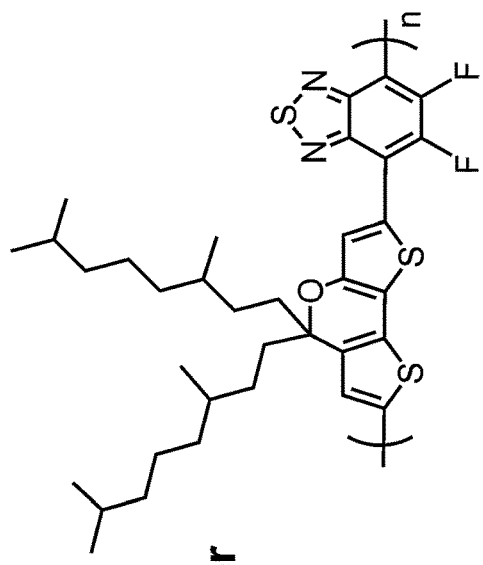
Figure 20E:
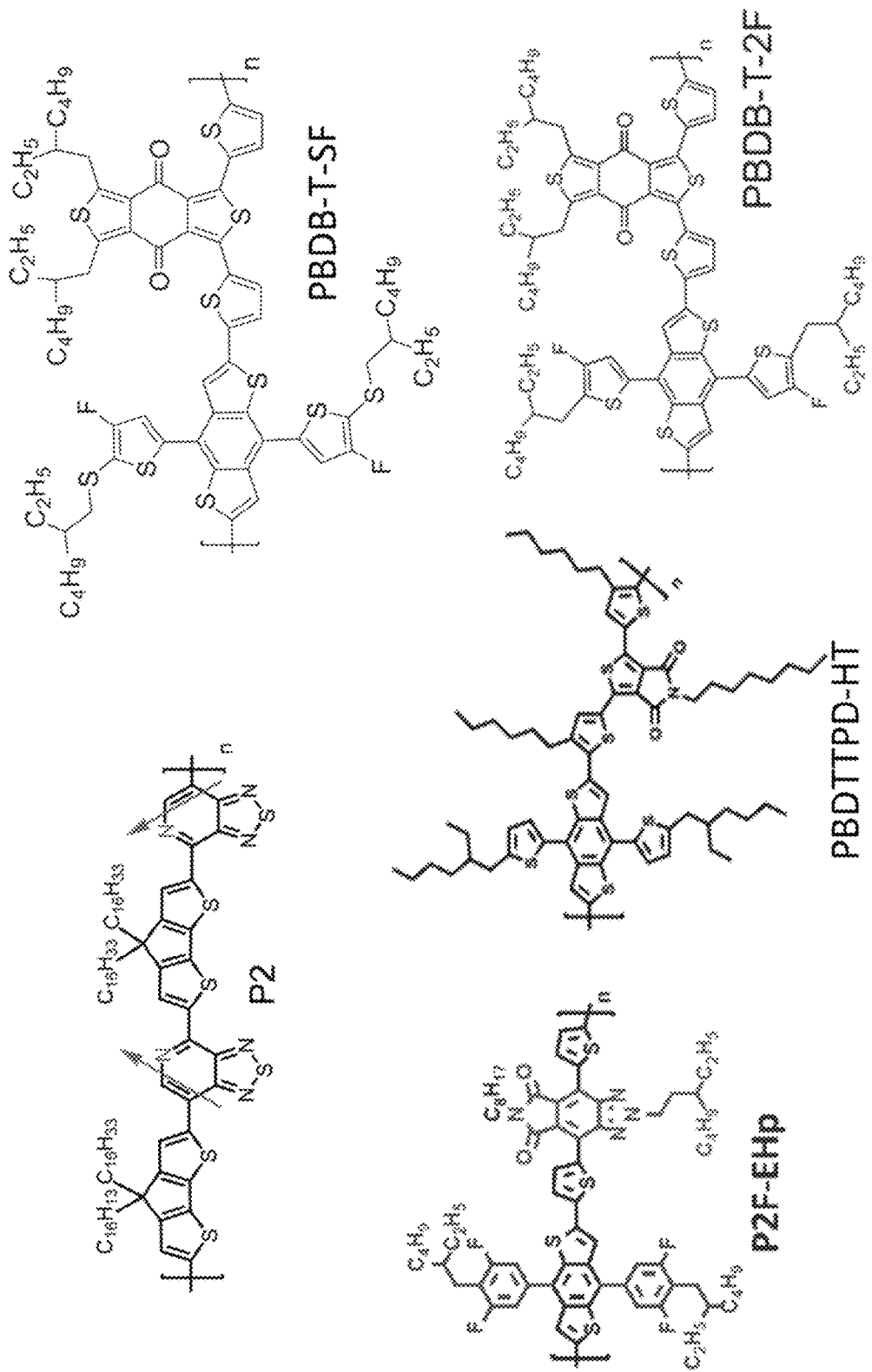
Figure 20F:
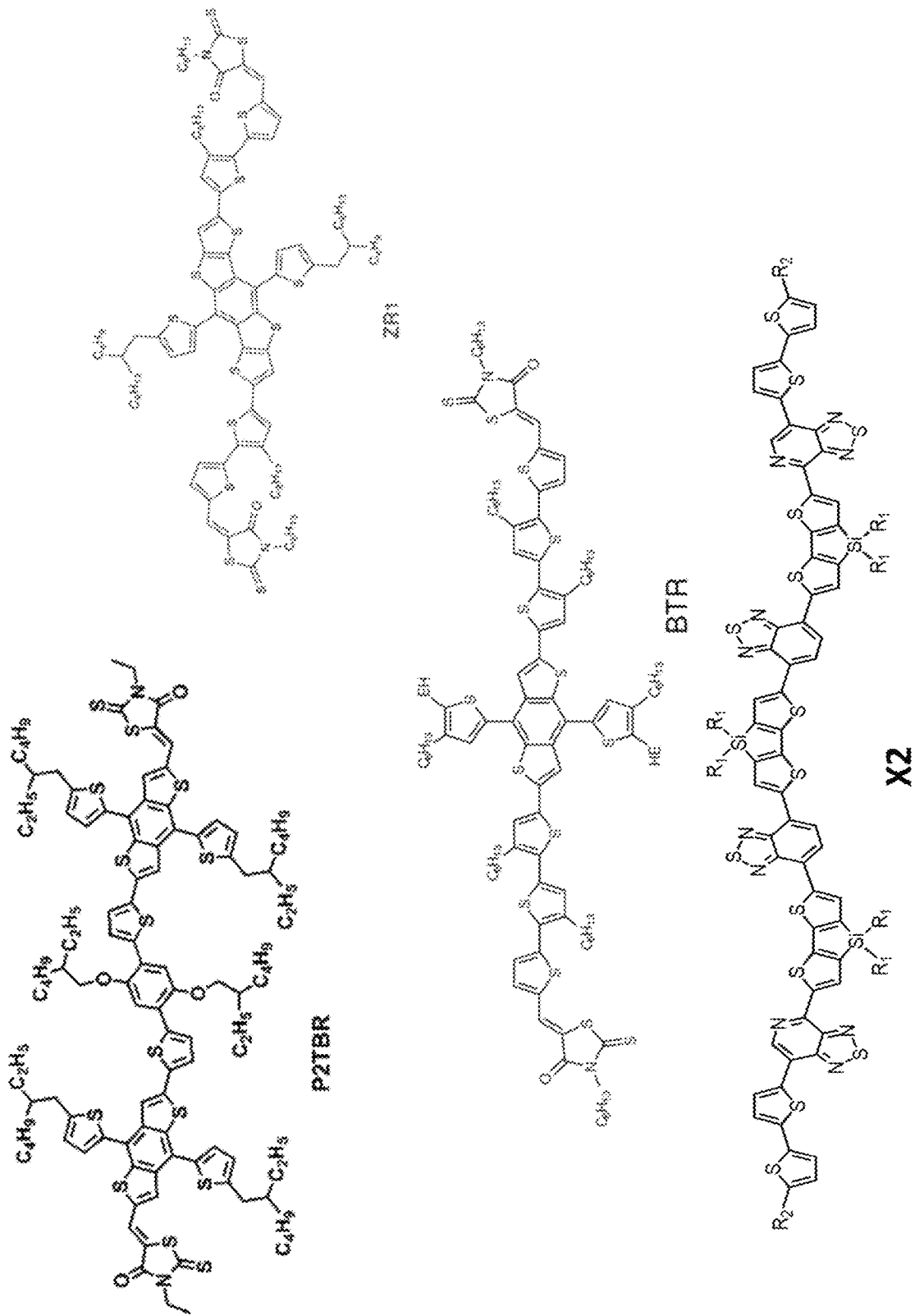

FIG. 18. Flowchart illustrating a method of making a composition of matter and a device.

FIGS. 19A-19H illustrate electron-accepting units that can be used in embodiments of the present invention.

FIGS. 20A-20F illustrate polymer and small molecule donor examples which have similar or narrower optical bandgap, have shown promising OPV performance, and which can be used in one or more embodiments of the present invention.

Figure 21:
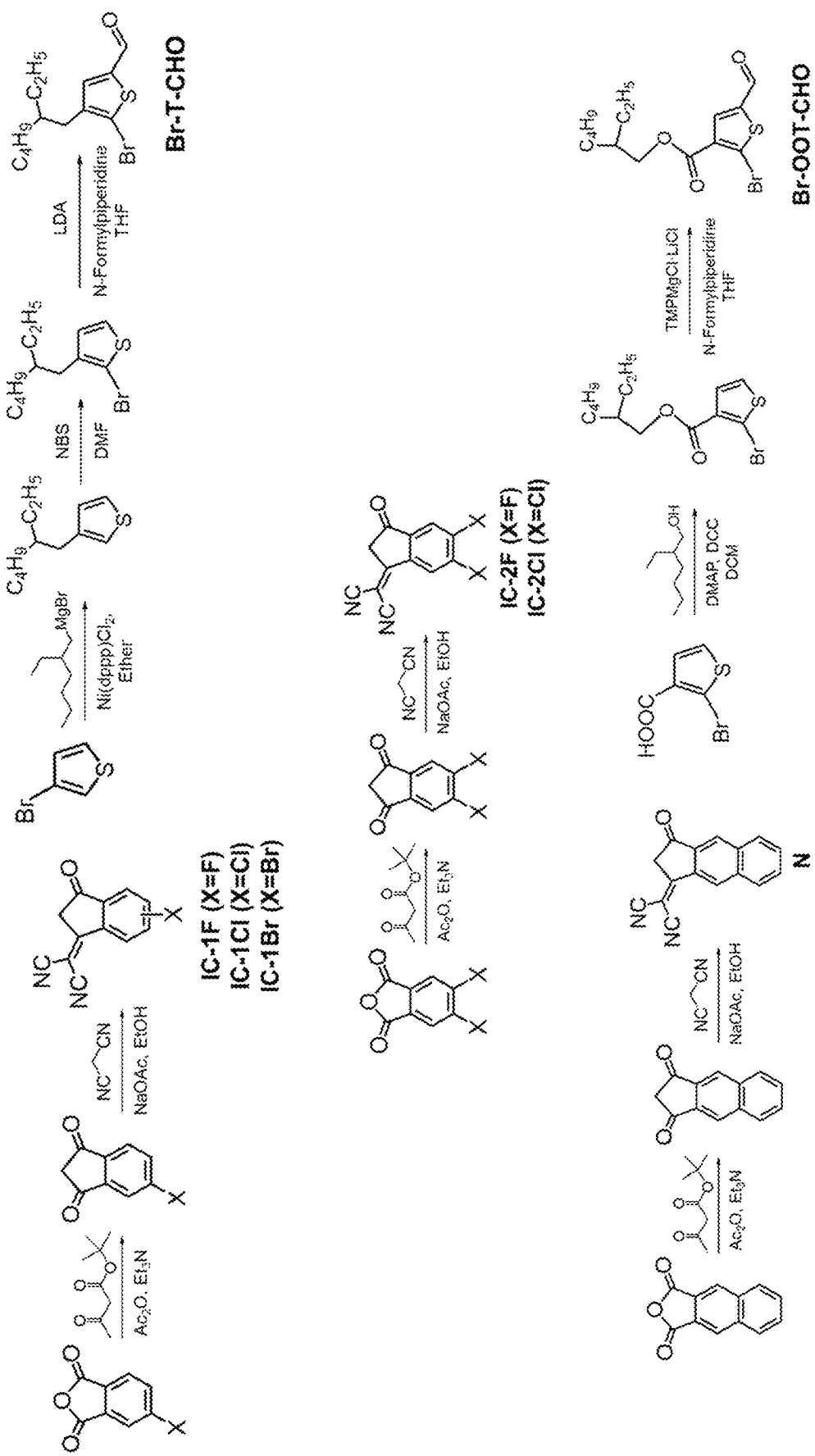

FIG. 21. Structures of intermediates used in exemplary synthesis procedures described herein.

DETAILED DESCRIPTION OF THE INVENTION

In the following description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

Technical Description

An ultra-NBG NFA, namely COTIC-4F exhibits great potential for NIR photodiodes with $E_g$ as low as ~1.10 eV.[25] As shown in FIG. 1a, the general structural design can be described as a A-D'-D-D'-A molecular configuration based on a key donor complex (electron rich core) comprising of cyclopentadithiophene (CPDT) as the central donor (D) and alkoxythienyl units as the flanking donor (D') fragment. Of note are the optoelectronic responses to NIR light of the BHJ photovoltaic devices based on COTIC-4F and PTB7-Th, such as a high short-circuit current density ($J_{SC}$) over 20 mA/cm$^2$ and low photon energy loss of ~0.52 eV. This encourages us to further control the device efficiencies of photodiodes by molecular engineering that fine-tunes the energy band structure.

The present disclosure describes the design of a new ultra-NBG NFA with a goal of achieving higher optoelectronic responses of both NIR solar cells and photodetectors. Our design strategy includes an incorporation of an asymmetrical D'-D-D" donor complex which comprises a CPDT unit (D) flanked by two different donor units, alkoxythienyl unit (D') and alkylthienyl unit (D"). The structure is completed with molecular termini containing 2-(5,6-difluoro-3-oxo-2,3-dihydro-1H-inden-1-ylidene)malononitrile (IC-2F) acceptor (A) units.

Without being bound by a particular scientific theory, embodiments of the present disclosure improve the efficiency of exciton splitting without sacrificing the open-circuit voltage ($V_{OC}$) in the devices by expanding the $\Delta E_{HOMO}$ without significantly modifying their LUMO energies, e.g., by partially replacing the alkoxythienyl units which have intrinsically a greater electron donating strength with the alkylthienyl unit. This design approach dilutes the electron density of the molecule and thus downshifts mainly the HOMO energy level. Then, an asymmetrical small molecule CO1-4F can be achieved by end-capping with the electron accepting unit (A) 2-(5,6-difluoro-3-oxo-2,3-dihydro-1H-inden-1-ylidene)malononitrile (IC-2F), ultimately providing a A-D'-D-D"-A molecular configuration. Molecular design strategies to form the asymmetrical structure can produce a large natural dipole moment and thus the reinforce intermolecular forces over the symmetrical analogue,[26-28] also improve solubility in solution and miscibility with donor molecules, while maintain its narrow bandgap and broad light absorption property, resulting in higher device efficiencies of non-fullerene solar cells. As described herein, blends of the polymer donor PTB7-Th and CO1-4F in photodiodes yielded a power conversion efficiency (PCE) of ~10.24% with a very high short-circuit current density of ~25 mA/cm² and a record responsivity of 0.52 A W⁻¹ at 920 nm.

1. First Examples: COTIC-4F, CTIC-4F and CO1-4F

We examined the impact of side chain modifications on the optoelectronic properties of NFAs built on the COTIC-4F conjugated framework (FIG. 1a). Starting with COTIC-4F (A-D'-D-D'-A), we designed and prepared CTIC-4F (A-D"-D-D"-A, D"=alkylthienyl) and CO1-4F (A-D'-D-D"-A). Our molecular design rationale is as follows. First, the different side chains, specifically alkyl vs. alkoxy groups, would modify the intramolecular charge transfer (ICT) characteristics of the excited states due to their differences in electron-donating strengths.[33,34] By changing the number of alkoxy groups on the thiophene units adjacent to D, we find that one can achieve a smooth progression of the optical gap ($E_g$) and molecular orbital energy levels. These features ultimately translate into OPDs tailored to match specific spectral responses. Second, and more broadly, CPDT and IC-2F have strong electron-donating and electron-withdrawing properties, respectively, resulting absorption profiles in the 700 nm to 1100 nm range. Characterization of OSC devices show that CTIC-4F and CO1-4F blended with the donor conjugated polymer PTB7-Th are able to display power conversion efficiency (PCEs) of over 10%, with $J_{SC}$ values as high as ~25 mA·cm⁻². More importantly from a practical perspective, we leveraged the optoelectronic properties of the blends to realize efficient OPDs with responsivities of 0.51 A W⁻¹ at 830 nm, 0.52 A W⁻¹ at 920 nm, and 0.42 A W⁻¹ at 995 nm for CTIC-4F, CO1-4F, and COTIC-4F, respectively.

a. Structures and Synthesis Method

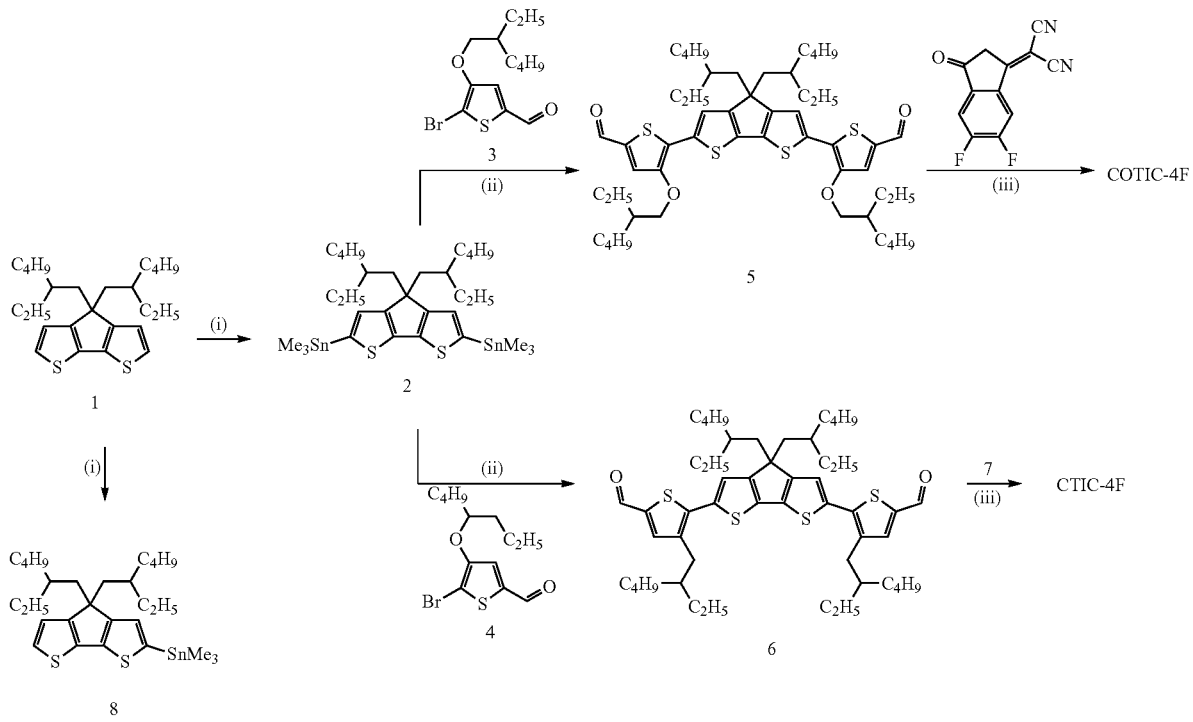

Scheme 1. Synthetic procedures for CTIC-4F, CO1-4F, and COTIC-4F.

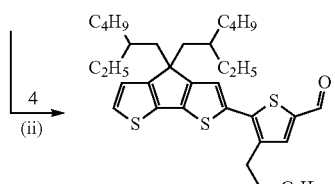
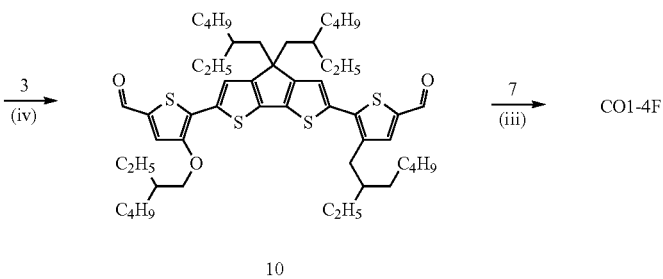

(i) n-BuLi, THF, Me₃SnCl, -78° C.;
(ii) Pd(PPh₃)₄, Toluene, 110° C.;
(iii) Chloroform, pyridine, 60° C.;
(iv) Pd(OAc)₂, P$^t$Bu₂Me•HBF4, DMF, K₂CO₃, PivOH.

TABLE 1

Optical and electrochemical properties of CTIC-4F, CO1-4F, and COTIC-4F.

| compound | $\lambda_{s, max}$ (nm)[a] | $\lambda_{f, max}$ (nm)[b] | $E_g^{opt}$ (eV)[c] | HOMO (eV)[d] | LUMO (eV)[e] | $E_g^{CV}$ (eV)[f] |
|---|---|---|---|---|---|---|
| CTIC-4F | 744 | 830 | 1.3 | −5.4 | −4.0 | 1.4 |
| CO1-4F | 814 | 920 | 1.2 | −5.3 | −4.1 | 1.2 |
| COTIC-4F | 875 | 995 | 1.1 | −5.2 | −4.1 | 1.1 |

[a]Absorption maximum in solution.
[b]Absorption maximum in thin film.
[c]Optical bandgap calculated from the absorption edge of the thin film.
[d]HOMO energy level estimated from the oxidation onset potential.
[e]LUMO energy level estimated from the potential of the reduction onset.
[f]HOMO-LUMO gap estimated from cyclic voltammetry.

The new asymmetric molecule CO1-4F was rationally designed and calculated by employing quantum chemistry calculations using density functional (DFT) with the semi-empirically tuned ωB97XD/6-31G (d,p) functional and basis set where the bulky side chains were simplified to ethyl. Calculations indicate CO1-4F has a relatively larger dipole moment of 1.68 D, while the dipole moments of symmetric COTIC-4F and CTIC-4F are 1.05 and 0.06 D, respectively.

The synthetic routes of NFAs are depicted in Scheme 1. COTIC-4F was reported through two facile reactions including Stille coupling and Knoevenagel condensation. A similar synthetic pathway was employed to produce a symmetric molecule CTIC-4F by replacing π-bridging unit ((2-ethylhexyl)oxy)thiophene with (2-ethylhexyl)thiophene. Stille coupling reaction between (4,4-bis(2-ethylhexyl)-4H-cyclopenta[1,2-b:5,4-U]dithiophen-2-yl)trimethylstannane (8) and 5-bromo-4-(2-ethylhexyl)thiophene-2-carbaldehyde (4) in the presence of catalytic Pd(PPh₃)₄ in anhydrous toluene produced monoaldehyde 9. C—H activated direct arylation between compound 9 and compound 3 was employed to produce key asymmetric intermediate 10, followed by end-capping with 2-(5,6-difluoro-3-oxo-2,3-dihydro-1H-inden-1-ylidene)malononitrile (7) to obtain the target NFA CO1-4F. The new compounds were characterized by spectroscopic methods (see Supporting Information in [49] or the U.S. Provisional Patent Application No. 62/806,232) and exhibit good solubility in common organic solvents such as dichloromethane, chloroform (CF), and chlorobenzene (CB) at room temperature.

b. Absorption Measurements

Absorption spectra of solutions of NFAs are shown in FIG. 1b. In CF solution, an absorption maximum ($\lambda_{max}$) redshifts gradually from 744 to 814 to 875 nm, accompanied by increasing maximum molar extinction coefficients, as the number of oxygen atom increases (i.e. as the D″ alkyl side group is replaced by D′, alkoxy side group, i.e. CTIC-4F→CO1-4F→COTIC-4F). From the solution to the film state (FIG. 1c), remarkable redshifts (~100 nm) for three NFAs can be observed. Optical transitions of NFAs are located in the NIR region with $E_g^{opt}$ values of 1.3±0.02 eV, 1.2±0.02 eV, and 1.1±0.02 eV for CTIC-4F, CO1-4F, and COTIC-4F, respectively. The absorption edge of the asymmetrical CO1-4F occurs between those of the two symmetrical CTIC-4F and COTIC-4F. Cyclic voltammetry (CV) measurements were carried out to estimate orbital energy levels. The HOMO and LUMO levels were deduced from the onsets of the oxidation and reduction peaks, respectively (Figure S6in Supporting information of [49] or the U.S. Provisional Patent Application No. 62/806,232).

The resulting HOMO/LUMO energy level estimates of CTIC-4F, CO1-4F, and COTIC-4F are therefore −5.4±0.04/−4.0±0.04 eV, −5.3±0.04/−4.1±0.04 eV, and −5.2±0.04/−4.1±0.04 eV, respectively (FIG. 1d). Altogether, these data confirm that incorporation of alkoxy side chains into the π-bridging thienyl unit increases the electron density within the conjugated backbone core (D′-D-D′>D′-D-D″>D″-D-D″) and thus gradually upshifts the HOMO energy levels.[20,29] Our study[25] has revealed that PTB7-Th:COTIC-4F-based solar cells generate large photocurrents in the NIR region despite the HOMO-HOMO energetic offset between PTB7-Th and COTIC-4F being very small or negligible as evaluated by CV. Despite the intrinsic uncertainty associated with electrochemically derived energy levels, these observations imply that efficient hole transfer occurs from COTIC-4F to PTB7-Th despite a relatively small driving force. Since CTIC-4F and CO1-4F possess lower HOMO energy levels relative to that of COTIC-4F, it is hypothesized that efficient charge generations can occur from both NIR-absorbing NFAs when blending with PTB7-Th.

c. Differential Scanning Calorimetry

The modification of side chains on the π-bridging thienyl unit has a strong impact on the thermal properties. Differential scanning calorimetry (DSC) scans were performed and show that at a rate of 2° C. min$^{-1}$, distinct melting transitions are observed at 238° C. for CTIC-4F; and an exothermic crystallization occurs at 191° C. during the cooling process. A smaller melting transition at a similar temperature (237° C.) is observed for CO1-4F whereas COTIC-4F does not show an obvious melting endotherm. These data indicate that the ethylhexyl side chains tend to induce the crystallization of molecules, probably because the backbone rigidity of molecules decreases gradually as the effect of the intramolecular locking induced by ethylhexyloxy side chains is declining from COTIC-4F to CO1-4F to CTIC-4F (whereas a cold crystallization of amorphous molecules at 148° C. and a smaller exothermic crystallization at 162° C. are observed).

d. Solar Cell Devices Comprising the Compositions of Matter

TABLE 2

Photovoltaic performances of OSCs based on PTB7-Th and the three new NFAs measured under simulated 100 mW $cm^{-2}$ AM 1.5 G illumination.

| Acceptor[a] | $V_{OC}$ (V) | $J_{SC}$ (mA cm$^{-2}$) | FF | PCE$_{max}$ (%)[b] | Cal. $J_{SC}$ (mA cm$^{-2}$) |
|---|---|---|---|---|---|
| CTIC-4F | 0.70 | 23.4 | 0.64 | 10.5 (10.0 ± 0.4) | 22.6 |
| CO1-4F | 0.64 | 24.8 | 0.64 | 10.2 (10.0 ± 0.3) | 24.0 |
| COTIC-4F | 0.57 | 20.7 | 0.61 | 7.3 (6.9 ± 0.3) | 20.4 |

[a]PTB7-Th:acceptor blend ratios are 1:1.5 (w/w). 2 vol % CN was used as a processing solvent additive.
[b]Average values from 18 devices.

Figure 1:
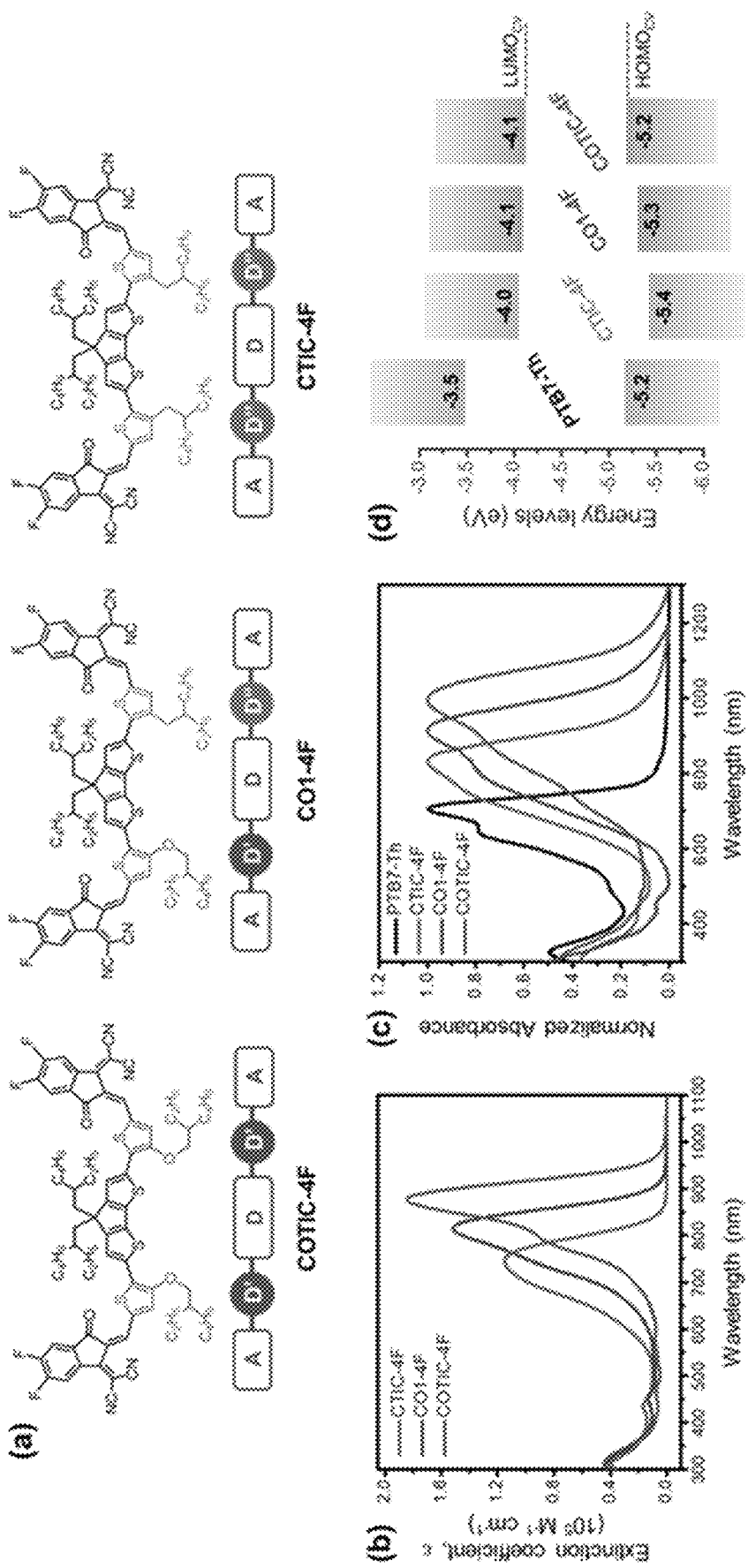
FIG. 1(a) Chemical structures of CTIC-4F, CO1-4F, and COTIC-4F. Absorption spectra of (b) solution and (c) film. (d) Energy level diagram of active layer components estimated from film CV measurements.
Figure 2:
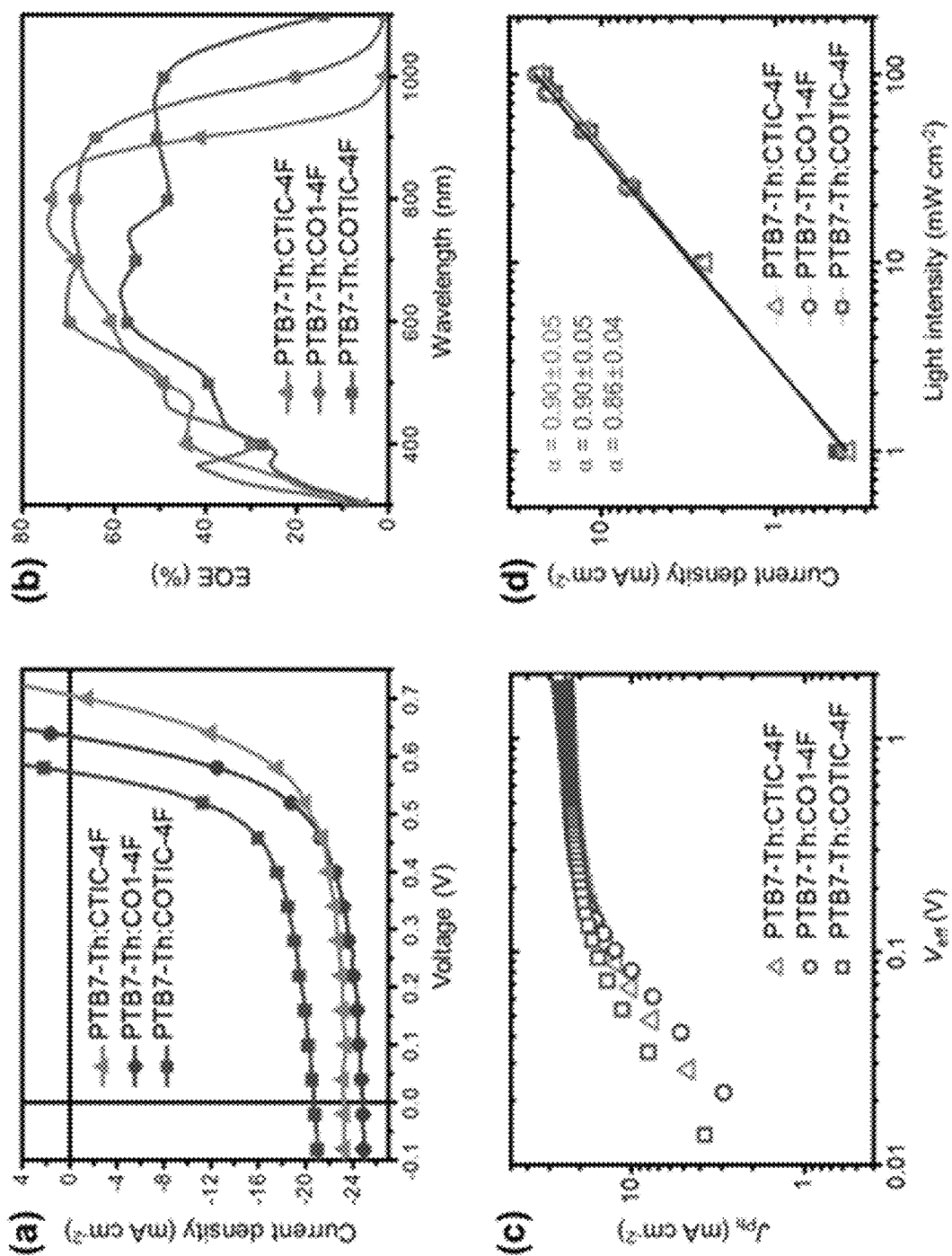
FIG. 2. (a) J-V characteristics and (b) EQE spectra of the optimized OSC devices under AM 1.5 G illumination at 100 mW cm$^{-2}$. (c) $J_{ph}$ versus $V_{eff}$ characteristics, and (d) $J_{sc}$ versus light intensity of the optimized devices.

Solar cells with the architecture ITO/ZnO/PTB7-Th:NFA/MoO$_3$/Ag were fabricated in order to compare the performance of COTIC-4F, CTIC-4F and CO1-4F. Semiconductor active layers were optimized using different blend weight ratios and solvent mixtures, as demonstrated in Figure S8 and Table S1 in the Supporting Information of [49] or the U.S. Provisional Patent Application No. 62/806,232. Optimal photovoltaic performances were achieved with a blend ratio of PTB7-Th:NFA of 1:1.5 (wt %) using CB as the solvent and 2 vol % 1-chloronaphthalene (CN) as the processing additive. FIG. 2a and Table 2 show the J-V characteristics of the optimized cells and a summary of device parameters, respectively. Devices with CTIC-4F, CO1-4F, and COTIC-4F show average PCEs of 10.0±0.4%, 10.0±0.3% and 6.9±0.3% with open-circuit ($V_{OC}$) values of 0.70 V, 0.64 V, and 0.57 V, respectively. Trends in $V_{OC}$ values follow expectations anticipated by examination of the LUMO energy differences between the specific NFA and PTB7-Th. Exact correlations are hampered by the standard experimental errors associated with the CV-determined LUMO levels provided in FIG. 1d. Average $J_{SC}$ values of 22.9±0.6 mA·cm$^{-2}$, 25.0±0.4 mA·cm$^{-2}$, and 20.9±0.5 mA·cm$^{-2}$ were obtained for devices with CTIC-4F, CO1-4F, and COTIC-4F, respectively. These $J_{SC}$ values trace their origin to high external quantum efficiency (EQE) responses in the NIR region (FIG. 2b) and are well matched to estimates calculated from EQE measurements, as shown in Table 2.

Charge collection probabilities were calculated from the photocurrent density ($J_{ph}$) dependence of the effective voltage ($V_{eff}$) in order to gain insight into the differences in device performance, see FIG. 2c. Here, $J_{ph}$ is defined as $J_{ph}=J_L-J_D$, where $J_L$ and $J_D$ are the current densities under illumination and in the dark, respectively. The effective voltage $V_{eff}$ is defined as $V_{eff}=V_0-V_a$, where $V_a$ is the applied bias and $V_0$ is the voltage at the point where $J_{ph}=0$. The photocurrent densities $J_{ph}$ of all NFA-based devices saturate ($J_{sat}$) at $V_{eff}$ of 1~2 V. The values for $J_{sat}$ are similar for all devices (COTIC-4F, CO1-4F, and CTIC-4F are 24.3, 25.3, and 24.5 mA cm$^{-2}$, respectively), implying similar rates of free charge carrier generation. The exciton dissociation and charge collection probability in the devices could be estimated by calculating $J_{ph}/J_{sat}$. Under short-circuit and maximal power output conditions, the values of $J_{ph}/J_{sat}$ for the optimized devices with CTIC-4F, CO1-4F and COTIC-4F are 94, 95 and 88%, respectively. Thus, PTB7-Th:CTIC-4F and PTB7-Th:CO1-4F blend systems are more efficient for exciton dissociation and/or charge collection than PTB7-Th:COTIC-4F. This result is a good agreement with the lower EQE value obtained for the device with PTB7-Th:COTIC-4F blend (FIG. 2b). In addition, fill factor (FF) provides indirect evidence of bimolecular recombination scales. The similar FFs for the devices including CTIC-4F (0.64) and CO1-4F (0.64) are also well matched with their similar charge collection efficiency.

The light-intensity (P) dependence of $J_{SC}$ were also measured to understand non-geminate recombination behaviour for three NFAs-based devices. FIG. 2d shows dependence of $J_{SC}$ on light intensity, which followed a power law relationship ($J_{SC}$~$P^\alpha$, where P is the light intensity).[30,31] Deviations from α=1 are attributed to non-geminate (bimolecular/trap-assisted) recombinations, which may limit the $J_{SC}$.[32-34] The α values of optimized devices with CTIC-4F, CO1-4F, and COTIC-4F were 0.90, 0.90, and 0.86, respectively. The α values for the devices with both CTIC-4F and CO1-4F are similar and higher than the α value for the device with COTIC-4F, which indicates that the use of CTIC-4F and CO1-4F molecules provides a beneficial way to decrease bimolecular recombination. The higher $J_{SC}$ of 23.36 mA/cm$^2$ and 24.80 mA/cm$^2$ values obtained from the device with CTIC-4F and CO1-4F, respectively, are consistent with the higher value of a (0.90) compared to the device with COTIC-4F (the lower value for a observed for COTIC-4F may in part cause the comparatively lower charge collection probability).

e. Photodetectors Including the Compositions of Matter

Taking advantage of the optoelectronic properties of PTB7-Th:NFA, we also fabricated efficient NIR organic photodetectors. The responsivity (R), which is an important parameter for evaluating the light-responding performance of a photodetector, is defined as the ratio of photocurrent to the incident light intensity, and can be calculated from the EQE according to the following equation:[35]

$$R = \frac{J_{ph}}{I_{light}} = \frac{EQE \, \lambda}{1240}$$

where $J_{ph}$ is the photocurrent density in A/cm$^2$, $I_{light}$ is the incident light intensity in W/cm$^2$, λ is the wavelength. FIGS. 3a to 3c shows the spectral responsivity of the BM photodiodes based on CTIC-4F, CO1-4F and COTIC-4F, respectively. In accordance with the LUMO-HOMO differences for the three NFAs, the maximum responsivity of 0.49, 0.46 and 0.37 A/W was found at 830, 920 and 970 nm for CTIC-4F, CO1-4F and COTIC-4F under short-circuit condition, respectively. When the photodetectors are operated under reverse bias, responsivity is increased as a result of more efficient charge collection under external electric field. Under −3 V, CO1-4F based devices have shown responsivity of 0.52 A/W. To the best of our knowledge, this is the highest responsivity at around 900 nm achieved with organic photodetector without introducing gain mechanism. In addition to responsivity, another critical figure of merit for the photodetector is specific detectivity (D*), which evaluates the sensitivity of a photodetector to weak optical signals. The shot noise-limited specific detectivity can be calculated from the responsivity and dark J-V characteristics.[36] The D* of the three types of photodetectors is shown in FIGS. 3d to 3f. At 0 V, specific detectivity of $7.0 \times 10^{11}$, $1.5 \times 10^{12}$ and $1.7 \times 10^{11}$ jones, are obtained for CTIC-4F, CO1-4F and COTIC-4F based devices. As the reverse bias increases, the D* decreases for all three NFAs based photodetectors. At −3 V, the corresponding values are $1.2 \times 10^{10}$, $2.6 \times 10^{10}$ and $5.9 \times 10^{9}$ jones, respectively. This is due to positive effect of increasing R is outweighed by the negative effect of increasing the $J_d$, and thus the noise, under larger reverse bias. For example, as summarized in Table S2 in the Supporting Information of [49] or the U.S. Provisional Patent Application No. 62/806,232. the R has slight increase at −3 V for all photodetectors by less than 15% at their respective wavelength of $R_{max}$ with respect to at 0V, while the $J_d$ increases by 2-5 orders of magnitude, netting the decrease of D*. This suggests the limiting factor of detectivity performance is mainly associated with dark current and interface engineering are being carried out to minimize the dark current under reverse bias.

f. Grazing Incidence Wide-Angle X-Ray Scattering (GIWAXS) Measurements

Effect of the π-bridge alternation (e.g., permutation of D' and D" structural modules) and side chain modification on the molecular order and crystalline content of neat NFAs and blend films was investigated by Grazing incidence wide-angle X-ray scattering (GIWAXS). Two-dimensional (2D) GIWAXS patterns of neat and blend films processed with the same solvents as the optimized OSC devices are shown in FIG. 4. Corresponding line-cut profiles in the in-plane and out-of-plane are presented in Figure S10 and S11 in Supporting Information of [49] or the U.S. Provisional Patent Application No. 62/806,232. To investigate how processing additives affect the NFA and PTB7-Th components, we compared neat films prepared with and without CN additive, specifically films prepared with neat CB and with a CB: (2%)CN mixture similar to that used in the fabrication of optimal devices. It can be clearly seen that processing with CN dramatically changes the manner of molecular packing of CTIC-4F in a neat film (Figure S10). When processed with only CB, one observes that CTIC-4F and CO1-4F crystallites orient face-on relative to the substrate (FIGS. 4a and 4b), while crystallites of COTIC-4F adopt an edge-on orientation (FIG. 4c). In contrast to the CTIC-4F film processed with only CB, processing with CN (FIG. 4d) leads to a film with a sharp and intense (100) diffraction peak at $q_z=0.50$ Å$^{-1}$ (d-spacing: 12.5 Å), as well as an abundance of diffraction spots that cannot yet be attributed to specific structural features. These features imply that the use of CN promotes CTIC-4F molecules to organize in highly ordered domains, with the complex diffraction pattern suggesting the presence of multiple polymorphs.[37,38]
In the case of CO1-4F films treated with CN (FIG. 4e), one finds an edge-on orientation with a strong (100) diffraction peak at $q_z=0.41$ Å$^{-1}$ (d-spacing: 15.3 Å) and a π-π stacking peak at $q_{xy}=1.79$ Å$^{-1}$ (d-spacing: 3.51 Å). Comparison of FIGS. 4b and 4e highlights the remarkable impact of 2% processing additive to reverse the average orientation, relative to using pure CB. In the case of COTIC-4F (FIG. 4c vs. FIG. 4f), one observes the reverse: CN changes the average predominant orientation from edge-on to face-on. Thus, how and why the additive coordinates the differences in self-assembly is poorly understood.

The 2D GIWAXS image of the PTB7-Th:CTIC-4F blend processed with 2% CN (FIG. 4g) features an abundance of diffraction peaks that can also be observed in the neat CTIC-4F film processed with 2% CN. Although well-defined diffraction spots from CTIC-4F crystallites are lost in the blend with PTB7-Th, many remain, albeit with increased orientational disorder. Diffraction patterns of blends of PTB7-Th:CO1-4F (FIG. 4h) and PTB7-Th:COTIC-4F (FIG. 4i) display broad lamellar (100) packing in the in-plane direction and broad π-π (010) packing in the out-of-plane direction. It is worth pointing out that PTB7-Th is relatively insensitive to the blending with NFA component and orients face-on relative to the substrate (Figure S11). However, the organization of NFA crystallites in the blend is perturbed by the presence of PTB7-Th, when compared to the observations for the neat films. As mentioned above, the high degree of crystalline and orientational order observed for the CN-treated CTIC-4F film (FIG. 4d) is disturbed upon blending with PTB7-Th, while crystallites of CO1-4F in the PTB7-Th:CO1-4F blend adopt a face-on orientation, in contrast to the edge-on orientation in CN-treated CO1-4F films. During spin-coating with PTB7-Th, CO1-4F crystallites may be kinetically trapped in a metastable face-on state, favorable to out-of-plane charge transport necessary in diodes. COTIC-4F is face-on in the neat film processed by CB:CN, and appears to be face-on in the blend, although it is difficult to determine if the observed reflections are due to the PTB7-Th or the acceptor.

Replacing D" with the D' π-bridge exhibits discernible diffraction features along the horizontal and vertical directions similar to conjugated polymers. CO1-4F shows a typical edge-on orientation with a strong (100) diffraction peak at $q_z=0.41$ Å$^{-1}$ (d-spacing: 15.3 Å), noticeably larger than CTIC-4F, and a π-π stacking peak at $q_z=1.79$ Å$^{-1}$ (d-spacing: 3.51 Å) whereas COTIC-4F tends to adopt a bimodal texture with a coexistence of face-on and edge-on orientations. The molecular ordering of PTB7-Th within a neat film show a preferential face-on orientation (Figure S11 in Supporting Information of [49] or the U.S. Provisional Patent Application No. 62/806,232).

In the blend, although the highly ordered CTIC-4F crystallites were suppressed when blended with PTB7-Th, the blend shows sufficient scattering profiles. It is clearly seen that the PTB7-Th and CTIC-4F components maintain their crystalline features (Figure S11 in Supporting Information of [49] or the U.S. Provisional Patent Application No. 62/806,232), and therefore the information of the BHJ films is a summation of the packing features from both components.[20,39] In both blends based on PTB7-Th:COTIC-4F and PTB7-Th:CO1-4F, a quite broad spreading for both inter-lamellae (100) packing in the in-plane direction and π-π (010) stacking in the out-of-plane direction. We suspect that the diffraction features originate from the PTB7-Th and NFA crystals, as well as part of the components being reorganized into intermixed phases. One observes PTB7-Th is relatively insensitive to the blending with NFA component and orients face-on relative to the substrate as seen in the neat film.

We examined the morphological features of the blend films by using transmission electron microscopy (TEM). For films processed without CN, blends with three different NFAs (CTIC-4F, CO1-4F, or COTIC-4F) show a feature of intimately mixed morphology of donor:acceptor components (Figure S12 in Supporting Information of [49] or the U.S. Provisional Patent Application No. 62/806,232). Such an intimate mixing can be highly efficient in exciton splitting, but favors recombination, which reduces the photocurrent.[40] However, a much coarser phase separation at multi-length scale with a continuous pattern is observed in the optimized PTB7-Th:CTIC-4F or PTB7-Th:CO1-4F blends processed with CN (FIG. 5). The morphological feature in the PTB7-Th:CTIC-4F blend is similar to a metropolitan road network, where reticular roads are interconnected to each other. The PTB7-Th:CO1-4F blend shows a hierarchical or neuronal network, where main midribs are interconnected by multiple small veins[41-44] or multiple large masses (on the order of ~200 nm) are connected by fine networks.

A technique using electron energy loss spectroscopy (EELS) allows us to distinguish between PTB7-Th- and NFA-rich phases because only NFAs contain nitrogen atoms. As shown in Figure S13 in in Supporting Information of [49] or the U.S. Provisional Patent Application No. 62/806,232, the dark regions observed in the TEM images of FIG. 5 indicate NFA-rich phases through the EELS results. Therefore, the processing of CN additive leads to self-organized NFA phases in the blends, especially for CTIC-4F or CO1-4F. In spite of structural similarity, the reason why such a phase separation occurs for CTIC-4F or CO1-4F and not for COTIC-4F is not yet fully understood. However, it may provide more insight into the inferior device performance of COTIC-4F. The interconnected network morphology observed in the blends containing CTIC-4F or CO1-4F can be beneficial for continuous channels of charge transport in devices, which could contribute to the efficient photocurrent generation in the NIR region. This is supported by the differences in charge extraction probability that were determined for COTIC-4F in comparison to the other two NFAs (88% vs. 94% and 95%; FIG. 2c). The is further supported by transient $V_{OC}$-decay measurements employed to analyze non-geminate recombination losses in the studied solar cells.[45] These measurements yield recombination rates ($U(n) \propto n^\beta$, [$cm^{-3} s^{-1}$]) and effective recombination orders fin optimized solar cells (see Supporting Information). One finds that COTIC-4F solar cells exhibit the highest recombination rate ($U=1.03 \cdot 10^{21}$ $cm^{-3} s^{-1}$), and therefore highest recombination losses, when compared to CTIC-4F and CO1-4F solar cells ($U=2.47 \cdot 10^{20}$ $cm^{-3} s^{-1}$; $U=8.06.1020$ $cm^{-1} s^{-1}$) at the same charge carrier density (Figure S14). Moreover, the effective recombination order of COTIC-4F devices ($\beta=1.64\pm0.05$) is the highest, when compared to CTIC-4F ($\beta=1.49\pm0.03$) and CO1-4F ($\beta=1.49\pm0.06$) devices. This implies a higher relative contribution of bimolecular recombination to the overall losses.

g. Further Information on the Materials and Methods Used for the First Examples Materials All reagents and chemicals were purchased from commercial sources and used without further purification. All anhydrous organic solvents for the synthesis, characterization, and device fabrication steps were purchased from Sigma-Aldrich and TCI. Compound 1, 2, 3, 4, 5, 7, and 8 were prepared via a modified synthetic condition from literature.[1-4]

Characterizations of compounds $^1H$ and $^{13}C$ NMR spectra of intermediate monomers were recorded on a Varian Unity Inova 500 MHz spectrometer in deuterated chloroform solution ($CDCl_3$) with 0.003% TMS as internal reference. Mass spectra were obtained from Bruker Microflex Matrix-Assisted LASER Desorption Ionization-Time of Flight Mass Spectrometer (MALDI-TOF) using 1,8-Dihydroxy-9(10H)-anthracenone (Dithranol) as a matrix recorded in a (+)-reflector mode. Elementary analysis was carried out using a CE440 elemental analyzer. Ultraviolet-Visible-Near-infrared (UV-Vis-NIR) absorption spectra were recorded on a Perkin Elmer Lambda 750 spectrophotometer. For the measurements of thin films, materials were spun coated onto precleaned glass substrates from chloroform solutions (10 mg $mL^{-1}$). Optical band gap ($Eg^{opt}$) was determined from the absorption onset of thin film sample.

Film microstructure characterization Transmission electron microscopy (TEM) images were obtained using JEOL JEM-2200FS (with Image Cs-corrector).

Electrochemical characterization The electrochemical cyclic voltammetry (CV) was conducted on a CHI-730B electrochemistry workstation with glassy carbon disk, Pt wire, and Ag/Ag+ electrode as the working electrode, counter electrode, and reference electrode, respectively in a 0.1 M tetrabutyl ammonium hexafluorophosphate (n-$Bu_4NPF_6$)-anhydrous acetonitrile solution at a potential scan rate of 50 mV $s^{-1}$. Thin films of samples were deposited onto the glassy carbon working electrode from a 1.5 mg chloroform solution. The electrochemical onsets were determined at the position where the current starts to differ from the baseline. The potential of Ag/AgCl reference electrode was internally calibrated by using the ferrocene/ferrocenium redox couple (Fc/$Fc^+$).

Computational studies The optimized structures, energy levels, and HOMO and LUMO orbital distributions were calculated by density functional (DFT) theory, using the semi-empirically tuned ωB97XD/6-31G(d,p) functional and basis set. To simplify calculations, the alkyl chains were replaced with methyl or ethyl chains. The HOMO and LUMO levels were calculated by determining the difference in energy from the optimized ground state geometry of the cation and anion, respectively.

Grazing incidence wide angle X-ray scattering (GI-WAXS) analysis 2D GIWAXS measurements were performed using Beamline 9A at the Pohang Accelerator Laboratory (PAL). The photon energy is 11.055 keV ($\lambda=1.1214$ Å). The angle between the film surface and the incident beam was fixed at 0.12° for all of the samples. The measurements were obtained at scanning intervals of 2θ between 3° and 25°. The 2D GIWAXS images from the films were analyzed according to the relationship between the scattering vector q and the d spacing, $q=2\pi/d$. The GIWAXS images shown are normalized with respect to exposure time.

Fabrication and characterization of organic solar cell (OSC) devices The devices were fabricated by the following procedure. First, the ITO-coated glass substrates were cleaned with detergents, then sonicated in acetone and isopropyl alcohol and dried in an oven at 130° C. The zinc oxide (ZnO) solution was prepared using mixture of diethyl zinc and tetrahydrofuran (THF) (1:2, v/v %) and the ZnO film (35 nm) was prepared from spin-casting at 4000 rpm for 15 s and annealing at 110° C. for 15 min.[4,5] For deposition of the active layer, blend solutions of PTB7-Th (1 wt %):NFAs (1.5 wt %) dissolved in CB (with 2 vol % 1-chloronaphthalene) were spin-coated on top of the ZnO layer in a nitrogen-filled glove box. The device was pumped down in vacuum (<torr; 1 torr~133 Pa), and a 7 nm thick MoO$_3$/100 nm thick Ag electrode for our device architecture were deposited on top of the active layer by thermal evaporation. The deposited MoO$_3$/Ag electrode defined the active area as 20 mm$^2$. Photovoltaic characteristics measurements were carried out inside the glove box using a high quality optical fiber to guide the light from the solar simulator equipped with a Keithley 2635A source measurement unit. J-V curves were measured under AM 1.5G illumination at 100 mW cm' using an aperture (9.4 mm$^2$) to define the illuminated area. EQE measurements were conducted in nitrogen-filled glove box using an EQE system. The monochromatic light intensity was calibrated using a Si photodiode and chopped at 100 Hz.

Analysis of Non-geminate Recombination The V$_{OC}$-decay measurements were performed with devices encapsulated with two-component epoxy outside of the N$_2$-filled glove box. It was necessary to use a white light emitting LED as fast switching light source with an intensity of 100 mW/cm$^2$. The measurement setup was inside of a faraday cage to ensure proper grounding. These measurements yielded the transient V$_{OC}$-plots shown in Fig. S14(a). In general, the recombination rate U(n) can be described by the following equation:

$$U(n) = -\frac{dn}{dt} = -\frac{n}{\tau} = \gamma n^\beta \quad (1)$$

where n is the charge carrier density, t is the time, τ is the recombination lifetime, γ is the recombination coefficient, and β is the recombination order.[6] In order to determine U(n) it is necessary to obtain values for the charge carrier density n and the recombination lifetime τ. The charge carrier density can be calculated by the following equation:

$$n = n_i \exp\left\{\frac{qV_{OC}}{2kT}\right\} \quad (2)$$

where n$_i$ is the intrinsic charge carrier density, q the elementary charge, k the Boltzmann constant, and T the absolute temperature (T=300 K). The intrinsic charge carrier density can be described by:

$$n_i = \sqrt{N_C N_V} \exp\left\{-\frac{E_g}{2kT}\right\} \quad (3)$$

where N$_{C,V}$ is the effective density of states in the conduction and valence band, respectively, and E$_g$ is the effective band gap of the blends (PTB7-Th:CTIC-4F→E$_g$=1.16 eV; PTB7-Th:CO1→E$_g$=1.13 eV; PTB7-Th:COTIC-4F→E$_g$=1.08 eV). As an approximation, it can be assumed that N$_C$=N$_V$≈2.5·10$^{19}$ cm$^{-3}$ for blends of organic semiconductors.[7] It is therefore possible to calculate n$_i$ and correlate the transient V$_{OC}$ values obtained via V$_{OC}$-decay to the charge carrier density 11 (Fig. S14(b)). Through an analysis explained by Brus et. al.,[8] the lifetime τ can be calculated (Fig. S14(c)). Having determined the carrier density n and recombination lifetime τ, it is now possible to calculate the recombination rate U(n) as described in equation (1). The direct comparison of the absolute recombination rates U(n) at the same charge carrier density (n=10$^{15}$ cm$^{-3}$, dashed line in Fig. S14(d)) of the three systems shows that the PTB7-Th:COTIC-4F device exhibits the highest recombination rate (U=1.03·10$^{21}$ cm$^{-3}$ s$^{-1}$). For the PTB7-Th:CO1-4F- and the PTB7-Th:CTIC-4F-solar cells this analysis yields recombination rates of U=8.06·10$^{20}$ cm$^{-3}$ s$^{-1}$ and U=2.47.10$^{20}$ cm$^{-3}$ s$^{-1}$, respectively. These recombination rates correlate with the observed different morphologies, where the well mixed blend of PTB7-Th:COTIC-4F results in more recombination events happening, compared to the other two studied systems.

2. Material Synthesis 5,5'-(4,4-bis(2-ethylhexyl)-4H-cyclopenta[1,2-b:5,4-b'] dithiophene-2,6-diyl)bis(4-(2-ethylhexyl)thiophene-2-carbaldehyde) (compound 6): A mixture of 4,4-bis(2-ethylhexyl)-4H-cyclopenta[1,2-b:5,4-b']dithiophene-2,6-diyl)bis (trimethylstannane), compound 2, (900 mg, 1.24 mmol), 5-bromo-4-(2-ethylhexyl)thiophene-2-carbaldehyde, compound 4, (937 mg, 3.09 mmol), (Pd(PPh$_3$)$_4$) (71 mg), and dry toluene (20 mL) was added into a flame-dried and nitrogen-filled one-neck round-bottom flask (50 mL). The flask was purged with N$_2$ for 10 min and the reactant was heated to 120° C. for 36 h. After the mixture cooled to room temperature, DI water was added, and the mixture was extracted with dichloromethane three times (50 ml×3). The organic layer was dried over MgSO$_4$ and concentrated in vacuum. The residue was purified by silica gel column chromatography (n-hexane/ethyl acetate, 1/9) to afford the product as a sticky red solid (754 mg, 72%).

$^1$H NMR (500 MHz, CDCl$_3$, ppm): δ 9.83 (s, 2H), 7.56 (s, 2H), 7.16 (t, 2H), 2.77 (d, 4H), 1.89-1.98 (m, 4H), 1.71 (br, 2H), 1.25-1.30 (m, 16H), 0.84-1.05 (m, 28H), 0.60-0.74 (m, 12H).

2,24(2Z,2'Z)-((5,5'-(4,4-bis(2-ethylhexyl)-4H-cyclopenta [1,2-b:5,4-b']dithiophene-2,6-diyl)bis(4-(2-ethylhexyl)thiophene-5,2-diyl))bis(methanylylidene))bis(5,6-difluoro-3-oxo-2,3-dihydro-1H-indene-2,1-diylidene))dimalononitrile (CTIC-4F): A mixture of compound 6 (384 mg, 0.45 mmol) and 2-(5,6-difluoro-3-oxo-2,3-dihydro-1H-inden-1-ylidene) malononitrile, compound 7, (334 mg, 1.45 mmol), dry chloroform (20 mL), and pyridine (0.5 mL) was added into to a flame-dried and nitrogen-filled one-neck round-bottom flask (50 mL). The flask was purged with N$_2$ for 20 min and the reactant was heated to 60° C. for 16 h. After the mixture cooled to room temperature, the reaction mixture was concentrated in vacuum. The residue was purified by silica gel column chromatography (n-hexane/dichloromethane, 2/8) to afford the product as a dark green solid (443 mg, 76%).

$^1$H NMR (500 MHz, CDCl$_3$, ppm): δ 8.77 (s, 2H), 8.53 (q, 2H), 7.69 (t, 2H), 7.64 (s, 2H), 7.48 (t, 2H), 2.84 (d, 4H), 1.94-2.05 (m, 4H), 1.78 (br, 2H), 1.23-1.46 (m, 16H), 0.85-1.15 (m, 28H), 0.63-0.70 (m, 12H).

$^{13}$C NMR (125 MHz, CDCl$_3$): 186.01, 160.48, 160.46, 160.44, 158.21, 155.55, 155.44, 153.46, 153.35, 151.07, 151.05, 149.65, 149.60, 149.55, 140.95, 140.91, 140.87, 140.20, 140.11, 140.02, 137.25, 136.95, 136.93, 136.91, 136.68, 136.65, 136.61, 134.49, 134.45, 134.08, 134.04, 134.00, 123.74, 123.67, 123.61, 121.27, 115.04, 114.87, 114.27, 114.19, 112.65, 112.50, 69.68, 54.47, 43.33, 39.53, 39.51, 39.48, 38.15, 35.45, 34.18, 34.17, 33.93, 33.90, 33.88, 33.86, 32.60, 32.58, 31.24, 29.69, 28.69, 28.67, 28.59, 28.58, 27.38, 27.36, 25.75, 23.06, 23.05, 23.03, 22.83, 14.12, 14.11, 14.10, 14.04, 10.71, 10.70, 10.68, 10.66, 10.66, 10.65, 10.63.

5-(4,4-bis(2-ethylhexyl)-4H-cyclopenta[1,2-b:5,4-b']dithiophen-2-yl)-4-(2-ethylhexyl)thiophene-2-carbaldehyde (compound 9): A mixture of compound 8 (565.5 mg, 1 mmol), compound 4 (394 mg, 1.3 mmol), (Pd(PPh$_3$)$_4$) (58 mg), and dry toluene (20 mL) was added into to a flame-dried and nitrogen-filled one-neck round-bottom flask (50 mL). The flask was purged with $N_2$ for 20 min and the reactant was heated to 120° C. for 36 h. After the mixture cooled to room temperature, DI water was added, and the mixture was extracted with dichloromethane for three times (50 ml×3). The organic layer was dried over $MgSO_4$ and concentrated in vacuum. The residue was purified by silica gel column chromatography (n-hexane/ethyl acetate, 1/9) to afford the product as a sticky orange solid (525 mg, 84%).

$^1$H NMR (500 MHz, $CDCl_3$, ppm): δ 9.82 (s, 1H), 7.55 (s, 1H), 7.21 (d, 1H), 7.14 (t, 1H), 6.95 (m, 1H), 2.77 (d, 2H), 1.84-1.96 (m, 4H), 1.71 (br, 2H), 1.21-1.40 (m, 10H), 0.83-1.05 (m, 22H), 0.57-0.78 (m, 12H).

$^{13}$C NMR (125 MHz, $CDCl_3$): 182.45, 182.44, 158.44, 157.94, 157.90, 157.86, 143.23, 143.21, 139.78, 139.73, 139.55, 139.43, 138.77, 138.70, 138.58, 136.29, 136.26, 133.81, 133.72, 128.84, 126.35, 125.78, 122.98, 122.43, 122.38, 122.33, 53.82, 53.81, 53.79, 43.25, 43.19, 39.98, 39.94, 35.16, 34.27, 34.22, 34.20, 34.18, 33.78, 33.74, 33.70, 32.60, 32.56, 29.98, 29.72, 28.78, 28.74, 28.65, 28.62, 28.60, 27.38, 27.28, 27.25, 25.71, 25.68, 25.65, 23.06, 23.05, 23.04, 22.81, 22.79, 22.75, 22.74, 14.12, 14.11, 14.07, 10.74, 10.72, 10.70, 10.68, 10.66, 10.64.

5-(4,4-bis(2-ethylhexyl)-6-(34(2-ethylhexyl)oxy)-5-formylthiophen-2-yl)-4H-cyclopenta[1,2-b:5,4-b']dithiophen-2-yl)-4-(2-ethylhexyl)thiophene-2-carbaldehyde (compound 10): A mixture of compound 9 (250 mg, 0.4 mmol), compound 3 (147 mg, 0.46 mmol), $Pd(OAc)_2$ (10.8 mg, 0.05 mmol), $P^tBu_2Me·HBF_4$ (19.8 mg, 0.08 mmol), pivalic acid (40.8 mg, 0.4 mmol), potassium carbonate (165.8 mg, 1.2 mmol), and dry toluene (4 mL) was added into to a flame-dried and nitrogen-filled one-neck round-bottom flask (25 mL). The resulting mixture was purged with $N_2$ for 20 min and was heated to 120° C. for 16 h. After TLC analysis showed completion of the reaction, the resulting mixture was cooled to room temperature. DI water was added and the mixture was extracted with dichloromethane for three times (50 ml×3). The organic layer was dried over $MgSO_4$ and concentrated in vacuum. The residue was purified by silica gel column chromatography (n-hexane/ethyl acetate, 1/9) to afford the product as a sticky orange solid (210 mg, 72%).

$^1$H NMR (500 MHz, $CDCl_3$, ppm): δ 9.82 (s, 1H), 9.75 (s, 1H), 7.56 (s, 1H), 7.47 (s, 1H), 7.32 (s, 1H), 7.15 (t, 1H), 4.10 (d, 2H), 2.77 (d, 2H), 1.81-1.97 (m, 5H), 1.72 (br, 1H), 1.18-1.66 (m, 18H), 0.80-1.10 (m, 28H), 0.59-0.75 (m, 12H).

$^{13}$C NMR (125 MHz, $CDCl_3$): 182.42, 181.53, 158.69, 158.65, 158.53, 158.47, 152.94, 152.92, 142.83, 142.82, 139.75, 139.70, 139.64, 139.18, 139.16, 138.95, 138.94, 138.84, 138.53, 138.48, 135.45, 135.15, 135.06, 134.98, 134.95, 127.57, 123.48, 122.84, 120.19, 120.11, 74.39, 54.05, 54.04, 54.03, 43.22, 43.18, 39.98, 39.94, 39.73, 35.26, 34.27, 34.25, 34.22, 33.83, 33.78, 32.63, 32.58, 30.52, 30.51, 29.11, 29.10, 29.05, 28.80, 28.76, 28.64, 28.62, 28.56, 27.47, 27.31, 27.29, 25.72, 25.69, 25.66, 23.93, 23.89, 23.05, 23.04, 23.03, 23.00, 22.81, 22.77, 14.13, 14.11, 14.08, 14.07, 14.05, 14.02, 14.00, 11.18, 10.78, 10.77, 10.75, 10.70, 10.68, 10.67, 10.65, 10.61, 10.59, 10.58.

2-((Z)-2-((5-(6-(5-((Z)-(1-(dicyanomethylene)-5,6-difluoro-3-oxo-1H-inden-2(3H)-ylidene)methyl)-34(2-ethylhexyl)oxy)thiophen-2-yl)-4,4-bis(2-ethylhexyl)-4H-cyclopenta[1,2-b:5,4-b']dithiophen-2-yl)-4-(2-ethylhexyl) thiophen-2-yl)methylene)-5,6-difluoro-3-oxo-2,3-dihydro-1H-inden-1-ylidene)malononitrile (CO1-4F): A mixture of compound 10 (384 mg, 0.45 mmol) and 2-(5,6-difluoro-3-oxo-2,3-dihydro-1H-inden-1-ylidene)malononitrile, compound 7, (334 mg, 1.45 mmol), dry chloroform (20 mL), and pyridine (0.5 mL) was added into to a flame-dried and nitrogen-filled one-neck round-bottom flask (50 mL). The flask was purged with $N_2$ for 20 min and the reactant was heated to 60° C. for 16 h. After the mixture cooled to room temperature, the reaction mixture was concentrated in vacuum. The residue was purified by silica gel column chromatography (n-hexane/dichloromethane, 2/8) to afford the product as a dark green solid (443 mg, 76%).

$^1$H NMR (500 MHz, $CDCl_3$, ppm): δ 8.77 (s, 1H), 8.70 (s, 1H), 8.49-8.56 (m, 2H), 7.61-7.72 (m, 4H), 7.44-7.53 (m, 2H), 4.17 (d, 2H), 2.85 (d, 2H), 1.94-2.05 (m, 4H), 1.87-1.94 (m, 1H), 1.79 (br, 1H), 1.50-1.70 (m, 4H), 1.23-1.46 (m, 14H), 0.85-1.15 (m, 28H), 0.63-0.70 (m, 12H).

$^{13}$C NMR (125 MHz, $CDCl_3$): 186.18, 186.05, 161.11, 161.04, 160.98, 160.71, 160.69, 160.68, 158.25, 158.08, 155.55, 155.44, 154.81, 153.48, 153.35, 153.30, 153.24, 151.11, 149.65, 142.61, 141.44, 141.42, 140.22, 140.14, 140.05, 137.72, 137.70, 137.32, 137.27, 137.22, 137.19, 136.68, 136.68, 136.21, 136.19, 136.13, 134.48, 134.39, 134.11, 134.08, 134.04, 131.69, 129.77, 123.73, 123.67, 123.60, 122.56, 122.45, 122.34, 121.26, 120.73, 115.05, 114.99, 114.88, 114.81, 114.63, 114.56, 114.32, 114.24, 112.66, 112.51, 112.45, 112.30. 74.79, 69.59, 68.49, 54.22, 54.21, 43.43, 39.73, 39.48, 35.42, 34.17, 34.07, 34.04, 33.94, 32.64, 30.56, 30.53, 30.34, 29.71, 29.11, 29.10, 28.75, 28.72, 28.54, 28.52, 27.35, 27.33, 25.78, 24.00, 23.07, 23.06, 23.04, 22.85, 22.82, 14.13, 14.04, 14.01, 11.21, 10.66, 10.65, 10.59, 10.58.

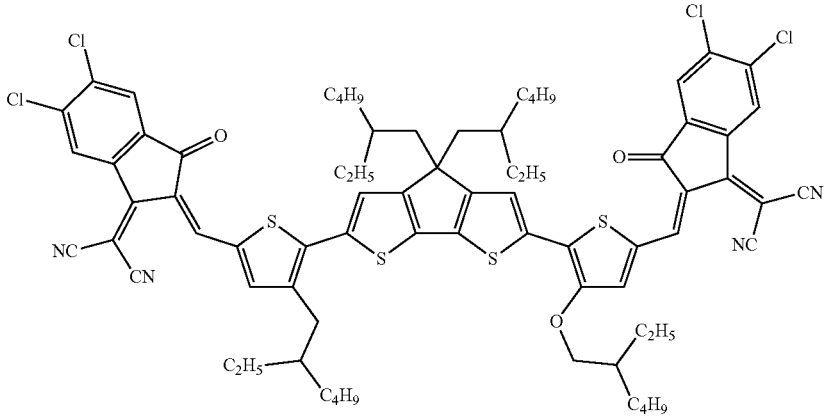

CO1-4Cl

By replacing the electron withdrawing fluorine atoms in CO1-4F with chlorine, a new asymmetric NFA CO1-4Cl with narrower bandgap of ~1.19 eV was achieved. It has been reported that chlorination of NFAs reduce optical bandgap but also lower NFA solubility so as to device performance. However, CO1-4Cl maintained good solubility in common organic solvents such as dichloromethane, chloroform (CF), and chlorobenzene (CB) at room temperature probably due to its more twisted asymmetric structure. PTB7-Th:CO1-4Cl based solar cell devices in an inverted structure (ITO/ZnO/Blend/MoOx/Ag) exhibit a high $J_{SC}$ over 22 mA/cm$^2$ and PCE over 8% (Table 3); a responsivity over 0.45 AW$^{-1}$ in the wavelength range of 750-950 nm wavelength, 0V or −0.1 V applied bias; a dark current as low as 1×10$^{-5}$ mA/cm$^2$ at −1V applied bias; a specific detectivity as high as 3×10$^{13}$ Jones at 940 nm wavelength, 0V applied bias, and 155 Hz measurement frequency; a specific detectivity over 1×10$^{13}$ Jones in the range of 500 nm-1000 nm wavelength, 0V applied bias, and 155 Hz measurement frequency (FIGS. 8 and 10). More detailed information is presented in the second example section below.

TABLE 3

Performance of solar cell devices based on PTB7-Th:NFAs blends.

| NFAs | $E_g^{opt}$ [eV] | Jsc (mA/cm$^2$) | Voc (V) | FF | PCE (%) |
|---|---|---|---|---|---|
| CO1-4Cl (CB annealed) | 1.15 | 22.77 ± 0.57 | 0.619 ± 0.001 | 0.539 ± 0.009 | 7.61 ± 0.29 |
| CO1-4Cl (CB + 2% CN) | 1.15 | 22.86 ± 0.54 | 0.616 ± 0.003 | 0.596 ± 0.014 | 8.39 ± 0.27 |

Second Example: High-Performance Solution-Processed Organic Photodetector for Near Infrared Sensing (References Refer to Listing for Second Example)

a. Introduction

Near-infrared (NIR) light usually corresponds to the region of electromagnetic radiation with wavelength spanning from about 750 nm to 1400 nm.[1] Despite being invisible to human visual perception, NIR sensing finds applications in a variety of technologies, including medical monitoring,[2] quality inspection,[3] machine vision,[4] and bio-imaging.[2] NIR sensing has been conventionally realized with detectors based on single-crystal inorganic semiconductor materials (e.g. Si, Ge, GaInAs), which typically have drawbacks including costly processing, mechanical inflexibility, and sensitivity to temperature.[6-8]

Owing to the low cost, solution processing, material tunability, unique structure-property relationships and good mechanical flexibility, organic semiconductors emerged as an exciting candidate for integrated electronics, lighting, solar cells and photodetection. Particularly, photodetectors based on organic semiconductors have witnessed increasing research endeavor, especially for extending their response from visible (Vis) spectrum into the NIR spectrum, leading to novel organic photodetectors (OPDs) with improved NIR sensitivity and broadband activity within the past decade. A critical prerequisite for fabricating OPDs with spectral response that extends into the NIR region is to incorporate a component with a sufficiently narrow optical bandgap ($E_g^{opt}$<1.55 eV), allowing exciton generation by the low-energy photons. Materials including narrow bandgap conjugated polymers (e.g., CPDT-TQ,[7] PTT,[9] PDDTT,[10] PDPP3T[11]), organic salts,[12] organic dyes,[13] and metallo-organics,[14,15] have been explored for this purpose and found success in achieving spectral response tailing off beyond 1000 nm. Nonetheless, the photodetection performance is generally limited by the low external quantum efficiency (EQE) due to the poor carrier generation and extraction, large noise current and the consequently low detectivity related to the poorly suppressed charge transport in the dark under reverse bias. In the pursuit of photon utilization in the NIR region, narrow bandgap non-fullerene acceptors (NFAs) have recently achieved substantial success in organic bulk-heterojunction (BHJ) systems. For example, Yao et al reported a small molecule, IEICO-4F, with $E_g^{opt}$ 1.24 eV, which demonstrated EQE greater than 60% at wavelengths larger than 800 nm for a BHJ solar cell.[16] Lee et al demonstrated an ultranarrow bandgap ($E_g^{opt}$=1.1 eV) NFA with 50% of EQE at 1000 nm when combined with poly[4,8-bis(5-(2-ethylhexyl)thiophen-2-yl)benzo[1,2-b;4,5-b']dithiophene-2,6-diyl-alt-(4-(2-ethylhexyl)-3-fluorothieno[3,4-b]thiophene-)-2-carboxylate-2-6-diyl)] (PTB7-Th).[17] Although the NFAs are actively explored for organic solar cells, their application in highly NIR-sensitive broadband OPDs, especially with well-balanced photoresponse and electrical characteristics in the dark remains comparatively underexplored.[6,18] In addition to the improvable photoresponse, the large dark/noise current under reverse bias has been a crucial limiting factor to achieving high sensitivity for OPDs. Even with a high NIR EQE achieved at 70%, large noise signals can lead to an undermined detectivity below 10$^{11}$ Jones.[19] While the application of the bulk heterojunction concept has greatly boosted exciton dissociation and overall quantum efficiency of organic photodiodes, the drawback brought by this approach is one of the most challenging to tackle in photodetection. For BHJ organic photodiodes, both the donor and acceptor materials may have direct contact with the anode and cathode. Even with application of charge blocking layers, this scenario raises the possibility of injection of holes from the cathode to the highest occupied molecular orbital (HOMO) of the donor, and electrons from the anode to the lowest unoccupied molecular orbital (LUMO) of the acceptor under reverse bias, leading to a large undesirable dark/noise current depending on different noise mechanisms.[19,20] This can be more severe with narrow bandgap systems due to smaller injection barriers. Pi Therefore, simultaneously achieving high NIR photoresponse and low dark/noise current with narrow bandgap materials is fundamentally challenging.

Herein, we demonstrate solution-processed BHJ OPDs with outstanding Vis-to-NIR sensing capability based on a novel asymmetric NFA. By including the NFA with a narrow optical bandgap of ~1.19 eV, large photoresponse can be extended up to 1100 nm. After optimization, the OPDs can provide a maximum NIR responsivity of approximately 0.5 A W$^{-1}$ in the wavelength region of 920-940 nm, outmatching the majority of OPDs.[6] To tackle the large dark/noise current commonly associated with BHJ OPDs, we have adopted a so-called "thick junction" strategy to suppress the shunt leakage and postpone the onset of space charge limited current.[22] Benefiting from a well-balanced performance under illumination and dark conditions, the presented OPDs give a low dark current density on the order of nanoamperes per centimeter square even at the moderate reverse bias of −2 V, leading to a peak shot noise-limited detectivity over $10^{13}$ Jones. With a more careful evaluation of the noise current, a high detectivity over $10^{12}$ Jones can be confirmed from 580 nm (visible) to 1010 nm (NIR), rendering these devices amongst the best high-performance broadband OPDs for Vis-to-NIR photodetection.

b. Device Structure

The active layer of our OPDs contains a BHJ system that comprises a polymer donor (PTB7-Th) and a novel asymmetric NFA, abbreviated as CO1-4Cl (see FIG. 6a for the chemical structure). The general design of CO1-4Cl can be summarized by an A-D'-D-D"-A asymmetrical configuration that is based on cyclopentadithiophene (CPDT) as the central donor (D) unit flanked with two different thienyl units as the sub-donor (D' and D") fragments, and is terminated by acceptor (A) units consisting of 2-(5,6-dichloro-3-oxo-2,3-dihydro-1H-inden-1-ylidene)malononitrile. CO1-4Cl was synthesized according to the procedure in the first example (e.g., according to [23] with slight modifications) and the synthetic route and materials characterization are shown in Figure S1 to S4 of the Supporting Information in [42] and the materials section f. below.

Strong NIR absorption can be observed from the absorption spectrum of the PTB7-Th:CO1-4Cl blend, peaking around 920 nm, which originates from the ultranarrow bandgap acceptor material, CO1-4Cl (FIG. 6b). The $E_g^{opt}$ of CO1-4Cl is ~1.19 eV according to the onset of absorption. The peak in the range of 700-800 nm corresponds to the absorption of PTB7-Th. The device structure and the corresponding energy diagram are provided in FIG. 6c. FIG. 6c illustrates the device includes a transparent cathode (e.g., indium tin oxide, ITO, or ITO/glass and labeled ITO/glass in the diagram); one or more cathode interface layers (or electron transport layer comprising, e.g., zinc oxide ZnOx); the active region on the cathode interface layer (active region comprising a bulk heterojunction, labeled BHJ, between an electron acceptor as described herein and an electron donor); one or more anode interface layers (or hole transport layer comprising e.g., MoOx) on the absorbing region; and an anode (e.g., Ag) on the anode interface layer.

The staggered bandgap alignment of CO1-4Cl and PTB7-Th demonstrates possibility of efficient charge separation following photogeneration of carriers. An inverted architecture was adopted for the fabrication of the OPDs. The zinc oxide layer, serving as a hole blocking layer, and the BHJ active layer were consecutively solution-processed onto a glass substrate coated with an indium tin oxide (ITO) layer, followed by the thermally evaporated electron blocking layer of molybdenum oxide and silver top electrode. The thickness of the active layer was varied by adjusting the concentration of PTB7-Th:CO1-4Cl blend solutions, producing devices with two typical active layer thickness of ~87 nm (the "thin" device) and ~300 nm (the "thick" device).

c. Device Morphology and Crystallinity

Atomic force microscopy (AFM) images (Figure S5 in Supporting Information of [42] or the priority application U.S. Provisional Patent Application No. 62/866,797) indicate that the BHJ active layers of both thin and thick devices have similar surface morphologies except that the root-mean-square (rms) roughness is slightly larger for the thick device (4.475 nm) than the thin device (3.327 nm). Both rms thickness values are small relative to the total thickness of the active layer, being 1.49% and 3.82% of the total thickness for the thick and thin devices, respectively. This is beneficial for reducing shunt leakage related to local non-uniformity of interfaces.

Grazing-incidence wide-angle X-ray scattering (GI-WAXS) was applied to study the molecular packing and crystalline feature of the neat films of the donor, acceptor and their blend. 2D GIWAXS patterns and the line-cut profiles for out-of-plane and in-plane features are shown in FIG. 7. A detailed summary of peak positions, stacking distance (d) and coherence lengths ($L_c$) are summarized in Table S1 in the Supporting Information of [42] or the priority application U.S. Provisional Patent Application No. 62/866,797. The presence of intense scattering at a large $q_z$ and small $q_{xy}$ in both neat films (FIGS. 7a and 7b) indicates that both the donor and acceptor adopt face-on orientation in their neat films. PTB7-Th and CO1-4Cl exhibit π-π stacking distances of 0.39 nm (1.63 $q_z$) and 0.34 nm (1.85 $q_z$), respectively. CO1-4Cl shows greater crystallinity than PTB7-Th, as evidenced by the narrower peaks (FIGS. 2d and 2e), and better long-range order, as reflected by larger $L_c$ values (Table S1 in the priority application). The features near 0.42 $q_z$ for CO1-4Cl in the neat film may be assigned to the presence of edge-on crystallites. However, these scattering features are much less intense than those from the face-on crystallites, revealing CO1-4Cl predominantly adopts face-on orientation. For the BHJ blend, the π-π stacking of CO1-4Cl near 1.85 $q_z$ is retained while the longer distance π-π stacking of CO1-4Cl and PTB7-Th near 1.64 $q_z$ are not present. Instead, an additional π-π stacking peak is identified near 1.79 $q_z$ which represents a new stacking distance (d=0.35 nm) not seen in either component. This likely represents a new polymorph which cannot be assigned definitively to CO1-4Cl or PTB7-Th, but indicates a tighter π-π stacking of the materials. Noticeably, the weak edge-on scattering feature observed in neat CO1-4Cl film is hardly observable in the blend film, which indicates the further suppression of the minor edge-on character of CO1-4Cl when being co-deposited with PTB7-Th[23]. Overall, the combination of these donor and acceptor materials in BHJ blend leads to preferential face-on orientation and smaller π-π stacking distances, which are favorable for efficient charge transport in vertical photodetectors where photogenerated carriers are extracted in the direction normal to the substrate.

d. J-V and EQE Characteristics

FIG. 8a shows the semi-log plot of the current-voltage (J-V) characteristics of the OPDs. Photodetectors based on vertical junction diodes typically work in the photoconductive mode, i.e., under reverse bias. For detecting weak optical signals or so-called self-powered operation, small reverse bias (e.g. −0.1 V) or photovoltaic mode at short circuit conditions (0 V) have also been employed.[10,15] Whichever type of operation is used, a low dark current is desirable for a potentially lower noise level and high sensitivity toward weak light signals. Hence, magnitude of the dark current under reverse bias is an important parameter for photodetectors. As shown in FIG. 8a, the thin device shows a dark current density of 200 nA $cm^{-2}$ at −2 V. The dark current is more effectively suppressed for the thick device, being as low as 7 nA $cm^{-2}$ at −2 V, which is one to four orders of magnitude lower than many of the previously reported OPDs.[7,9,10,12,18,24-26] Under the illumination of 940 nm monochromatic infrared light of ~54 µW cm$^{-2}$, the current density reaches a magnitude of 10$^{-5}$ A cm$^{-2}$ under reverse bias for both the thin and thick device, promising the high NIR sensitivity of our devices. To evaluate the charge collection efficiency following exciton dissociation, the photocurrent density ($J_{ph}$) versus effective voltage ($V_{eff}$) is plotted in Figure S6a in Supporting Information of [42] or U.S. Provisional Patent Application No. 62/866,797. As the effective voltage increases, the $J_{ph}$ increases as a result of the enhanced charge extraction and decrease of nongeminate losses. The $J_{ph}$ saturates ($J_{ph,sat}$) around 29.3 uA cm$^{-2}$ and 28.2 uA cm$^{-2}$ for the thin and thick devices, respectively, which implies similar rate of free charge carrier generation. Charge collection probabilities ($P_c$), estimated by the ratio of $J_{ph}$ to $J_{ph,sat}$ (Figure S6b in Supporting Information of [42] or U.S. Provisional Patent Application No. 62/866,797), is 0.948 and 0.850 for the thin and thick devices under short circuit condition, respectively. On the one hand, the relatively high values of Pc under short-circuit condition for both types of devices indicate the charge collection efficiency is already quite high without the assistance of an external electric field, a sign of good photon-to-electron conversion for this blend system even with a large thickness. On the other hand, it suggests limited space for further improvement of photoresponse by promoting charge collection with increased reverse bias. In other words, the photodetection limit under the operation condition ($V_{app} \leq 0$ V) may be ultimately determined by mainly the electrical characteristics of the photodetectors in the dark. This point will be illustrated in detail later.

To further quantify their spectral response, the external quantum efficiency (EQE) was measured as a function of incident light wavelength. For comparison, normal structure devices with the same thin active layer processing condition were also explored (Figure S7a in Supporting Information of [42] or U.S. Provisional Patent Application No. 62/866,797). The devices of both structures show similarly shaped EQE profiles. However, the EQE values are overall higher for the inverted one, even compared to the values from the normal structure counterpart under external bias (Figure S7b in Supporting Information of [42] or U.S. Provisional Patent Application No. 62/866,797). In addition, the dark current under reverse bias is larger by several orders of magnitude due to the inferior charge blocking capability from the PEDOT:PSS layer and low work function top barium/aluminum electrode (Figure S7c in Supporting Information of [42] or U.S. Provisional Patent Application No. 62/866, 797), which also predicts larger noise signals. Hence, further analysis focuses on the inverted structure OPDs in this work.

As shown in FIG. 8b, the OPDs show promising EQE values under a small reverse bias of −0.1 V, which vary from 60%-68% in the NIR wavelength from 750 nm to 940 nm, with the thin device moderately higher than the thick device. Devices with a medium active layer thickness (~140 nm) were also tested, which show comparable EQE values (Figure S8 in Supporting Information of [42] or U.S. Provisional Patent Application No. 62/866,797).

e. Responsivity and Detectivity

The responsivity (R) of a photodetector is an important figure-of-merit that characterizes the ratio of electrical output to optical input. Quoted in ampere produced per watt of incident light, R can be calculated as follows:

$$R = \frac{EQE}{100\%} \times \frac{\lambda}{1240 \text{ (nm } WA^{-1})} \quad (1)$$

where $\lambda$ is the wavelength of the incident light in nanometer. The spectral profile of responsivity peaks around 920 nm and 940 nm, reaching 0.50 and 0.45 A W$^{-1}$ for the thin and thick devices, respectively (FIG. 8b). With increased reverse bias, the responsivity of the photodetectors is slightly enhanced (Figure S9 in Supporting Information of [42] or U.S. Provisional Patent Application No. 62/866,797), with the highest responsivity reached under −2 V as 0.53 A W$^{-1}$ at 920 nm for the thin device, and 0.50 A W$^{-1}$ at 960 nm for the thick device. To the best of our knowledge, these results present the highest responsivity in the corresponding NIR wavelength range from OPDs without additional gain mechanisms (Figure S10 in Supporting Information of [42] or U.S. Provisional Patent Application No. 62/866,797). The relatively small increase of photoresponse under increased reverse bias (Figure S9 in Supporting Information of [42] or the priority application U.S. Provisional Patent Application No. 62/866, 797) is also consistent with the high Pc under short-circuit and reverse bias conditions.

In addition to responsivity, the specific detectivity (D*), quoted in cm Hz$^{1/2}$ W$^{-1}$ or Jones, depicts the sensitivity of a photodetector to weak optical signals. It is given by:

$$D^* = \frac{R\sqrt{AB}}{i_n} \quad (2)$$
$$= \frac{R\sqrt{A}}{S_n}$$

where A is the active device area in cm$^2$, B is the bandwidth in Hz, $i_n$ is the noise current in A, and $S_n$ is the noise current spectral density in A Hz$^{-1/2}$. The $S_n$ can be calculated from the current-voltage characteristics in the dark condition with the assumption that the shot noise has a major contribution under reverse bias. Accordingly, the shot noise-limited specific detectivity ($D_{sh}^*$) can be obtained:

$$D_{sh}^* = \frac{R\sqrt{A}}{\sqrt{2qi_d}} \quad (3)$$
$$= \frac{R}{\sqrt{2qJ_d}}$$

where $i_d$, $J_d$ and q stand for the dark current, dark current density and elementary charge, respectively. Contrary to the trend in responsivity, the thick device shows a larger $D_{sh}^*$ compared to the thin device throughout the tested wavelength range due to a smaller dark current (FIG. 8c). While both types of devices show large $D_{sh}^*$ over 10$^{13}$ Jones in the NIR wavelength range from 750 nm to 1000 nm, the thick device also demonstrates $D_{sh}^*$>10$^{13}$ Jones in the visible spectrum as well. It presents one of the highest NIR $D_{sh}^*$ achieved based on organic photodiodes, with a peak $D_{sh}^*$ of 3.31×10$^{13}$ Jones at 940 nm. The $D_{sh}^*$ spectral profiles under different biases are also shown in Figure S11 in Supporting Information of [42] or the priority application U.S. Provisional Patent Application No. 62/866,797. As found, despite having higher responsivity (Figure S9 in Supporting Information of [42]) under reverse bias for the thin device, the $D_{sh}*$ under larger reverse biases of −1 V and −2 V are still higher for the thick device as a result of a lower dark current and shot noise. It is worth noting that $D_{sh}*$ monotonically decreases as the reverse bias increases for both devices (FIG. 8d, Figure S11 in Supporting Information of [42] or the priority application U.S. Provisional Patent Application No. 62/866,797). This again implies that the current characteristics in the dark, rather than the photoresponse performance, poses the limit for the detection, which is similar to the previous work.[7,23] Nevertheless, even at a relatively large reverse bias of −2 V (corresponding to an electric field strength of 67 kV cm$^{-1}$), $D_{sh}*$ maintains over $10^{13}$ Jones from 860 nm to 980 nm for the thick device, confirming its robust NIR sensing capability.

To better understand the charge transport and the difference in the dark current between the thin and thick devices, the corrected current density-voltage ($J_{corr}$–$V_{rev}$) characteristics (FIGS. 8e and 8f) are analyzed. $J_{corr}$ is calculated according to:

$$J_{corr} = J - \frac{V_{rev} - JR_s}{R_{sh}} \quad (4)$$

where J is the absolute value of the apparent current density, $V_{rev}$ is the absolute value of the applied reverse bias, $R_s$ and $R_{sh}$ are the area-normalized series resistance and shunt resistance, respectively, as extracted from the differential resistance.[27] For the thick device, the region (<0.1 V) where $J_{corr} \propto V_{rev}^{0.5}$ corresponds to the charge transport mechanism of generation current.[28,29] Upon further increasing the reverse bias, $J_{corr}$-$V_{rev}$ becomes relatively flat due to the saturated generation current at the fully depleted active layer. Upon further increasing the reverse bias to larger than 1 V, the slope of the logarithmic $J_{corr}$-$V_{rev}$ curves exceeds 2, which is typical of the space charge limited current (SCLC) in the presence of traps.[30] For the thin device, the active layer is already fully depleted even at very small reverse bias, as can be seen from the flat $J_{corr}$-$V_{rev}$ curve under the reverse bias less than 0.2 V. The onset voltage for the SCLC region is about 0.23 V, much smaller than that of the thick device. In addition to the late onset of SCLC as a result of the injected charges, the thick device also has a larger $R_{sh}$ (4.4×10$^8$ Ω cm$^2$) than that of the thin device (6.2×10$^7$ Ω cm$^2$), as shown in Figure S12 in Supporting Information of [42] or the priority application U.S. Provisional Patent Application No. 62/866,797. The suppressed shunt leakage and SCLC (Figure S13a and S13b in Supporting Information of [42] or the priority application U.S. Provisional Patent Application No. 62/866,797) make the total dark current in the thick device much smaller and more favorable for high detectivity applications.

The actual noise level was experimentally obtained to avoid performance overestimation.[31-33] We probed the noise spectral density ($S_n$) of our OPDs (Figure S14 in Supporting Information of [42] or the priority application U.S. Provisional Patent Application No. 62/866,797) with fast Fourier transform of the dark current at −0.1 V and −2 V, respectively. At 100 Hz, the $S_n$ is 8.5×10$^{-14}$ and 5.9×10$^{-14}$ A Hz$^{-1/2}$ for the thin and thick devices at −0.1 V, respectively, whereas the values increase to 1.23×10$^{-12}$ and 1.0× 10$^{-13}$ A Hz$^{-1/2}$ at −2 V. The noise equivalent power (NEP) stands for the power of the light signal that generates a signal-to-noise (S/N) ratio of unity with output bandwidth of 1 Hz, characterizing the detection limit of the detector. It can be calculated by:

$$NEP = \frac{S_n}{R} \quad (5)$$

At a frequency of 100 Hz, the thick device has an NEP of 1.2×10$^{-13}$ W Hz$^{-1/2}$ at −0.1 V, and still holds as low as 2.0×10$^{-13}$ W Hz$^{-1/2}$ at −2 V, being one of the few reported OPDs that allow NIR detection of sub-picowatt signals according to the experimentally measured noise characteristics.[18] It is noticeable that at low bias in the low-frequency region (<100 Hz), the large noise may not be necessarily related to the properties of the OPDs (Figure S15 in Supporting Information of [42] or the priority application U.S. Provisional Patent Application No. 62/866,797).

With the measured noise spectra, the contour plot of specific detectivity (D*) can be derived, as shown in FIG. 9. At a small bias of −0.1 V, even at a low frequency where flicker noise is significant (10$^{-13}$-10$^{-12}$ A Hz$^{-1/2}$, Figure S14a in Supporting Information of [42] or the priority application U.S. Provisional Patent Application No. 62/866, 797), the values for D* in the whole wavelength range (400 to 1100 nm) are over 10$^{10}$ Jones for both devices (FIGS. 9a and 9c). In the frequency-independent region, an overall D* higher than 10$^{12}$ Jones in the NIR range from 750 nm to 980 nm is achieved for both devices due to their high responsivity and relatively low noise (<10$^{-13}$ A HZ$^{-1/2}$). At a larger bias of −2 V, the overall enlarged noise level results in a decrease of D* to below 10$^{12}$ Jones for the thin device. The maximum D* is around 5×10$^{11}$ Jones, achieved at the highest tested frequency around 1 kHz (FIG. 9b) as a result of the widening of the frequency-dependent region of the noise spectrum (Figure S14b in Supporting Information of [42] or the priority application U.S. Provisional Patent Application No. 62/866,797). This widening presents more dominant flicker noise, which is usually believed to originate from trapping and detrapping of carriers.[34] The result aligns well with the dramatically increased dark current due to the shunt leakage and injected SCLC under large bias, where the trapping and detrapping events become more apparent with large number of carriers being transported. Differently, thick device is still able to uphold D* over 10$^{12}$ Jones in the original wavelength range with suppressed charge transport. This detectivity is higher than the previously reported NIR detectivity achieved with photodetectors based on organic, organic-hybrid perovskite and inorganic materials,[7,18,20,35,36] and is close to one of the highest D* for visible spectrum realized with thick junction strategy.[22] The performance also competes well with a Si photodiode (Figure S16 in Supporting Information of [42] or the priority application U.S. Provisional Patent Application No. 62/866, 797). As the bandgap of the photoactive materials becomes narrower, the D* of non-gain photodetectors based on either organic or inorganic semiconductors becomes increasingly sensitive to the noise level due to a larger concentration of thermally excited carriers. Therefore, further improving D* relies on controlling the testing conditions, such as lowering the temperature.

The linear dynamic range (LDR) describes the range within which the detector output scales linearly with the input signals. Typically, the LDR can be calculated by:

$$LDR = 20\log\frac{I_{upper}}{I_{lower}} = 20\log\frac{J_{upper}}{J_{lower}} (dB) \quad (5)$$

where $I_{upper}$ and $I_{lower}$ respectively stand for the maximum and minimum irradiance beyond or below which the device signal-irradiance relation deviates from linearity. $J_{upper}$ and $J_{lower}$ are the corresponding photocurrent measured at $I_{upper}$ and $I_{lower}$, respectively. As shown in FIG. 10a, the photocurrent density ($J_{ph}$) under irradiation of 940 nm infrared light of different intensity is plotted for the thin and thick devices, which give LDR of 148 dB and 126 dB, respectively. The saturation (sub-linearity) of photocurrent at the higher end of light intensity is usually associated with the effect of bimolecular recombination.[33] Noticeably, the responsivity at the lowest light intensity is 6.64 A W$^{-1}$ and 4.92 A W$^{-1}$ for the thick device and the thin device, respectively. These values correspond to EQE of 876% and 649%, larger than the theoretical limit of 100%. Such super-linearity and EQE greater than 100% suggest that certain gain effect may take place. This can be caused by unbalanced extraction of photogenerated holes or electrons.[37] Such a "gain" effect has been explored for constructing photomultiplication-type organic photodetectors based on wider bandgap systems.[38,39] We are currently investigating the possibility of realizing such gain effects under a wider range of light intensity for our narrow bandgap systems.

f. Transient Response

To evaluate the response speed of the photodetector, the transient photoresponse behavior of the device was studied. For enhanced charge extraction and fast operation, the photodetectors are usually reversely biased at a relatively large bias. Therefore, the thick device operating under a reverse bias of −2 V was used for further study due to its better balance between the photoresponse and noise characteristics. FIG. 10b shows the current density as a function of time for the thick device under 940 nm infrared light modulated at 20 kHz (red) and 200 kHz (blue), respectively. In the former case, the output of the photodetector can follow the on-off switching of the optical signal and reach the steady-state photocurrent and dark current. When illumination modulation is at 200 kHz, the photodetector cannot fully reach the original photocurrent or decay to the dark current due to the limited response speed. An important parameter to evaluate the applicable bandwidth of a photodetector is the cutoff frequency ($f_{3dB}$), commonly defined as the frequency at which the output of a detector is attenuated to −3 dB, corresponding to 70.8% of the original amplitude. The temporal photoresponse at various light modulation frequencies was recorded to find the corresponding normalized response. As shown in FIG. 10c, the cutoff frequency is found to be around 240 kHz. In addition, the RC time constant-limited cutoff frequency ($f_{RC}$) can be calculated by:[40]

$$f_{RC} = \frac{1}{2\pi RC} \quad (6)$$

where the R is the sum of the series resistance ($R_{series}$) of the device, measured to be 62 Ohm, and the load resistance of the oscilloscope (50 Ohm), and C is the junction capacitance of the device, found as 0.34 nF. The corresponding $f_{RC}$ is calculated to be 4.18 MHz. This indicates the limiting factor of the response speed is not the RC time constant but possibly the transit time of the charge carriers.[40] The transit time-limited cutoff frequency (fir) can be obtained as:

$$f_{tr} = \frac{3.5}{2\pi\tau_{tr}} = \frac{3.5\mu_{eff}(V + V_{bi})}{2\pi L^2} \quad (7)$$

where $\tau_{tr}$ is the transit time of the charge carriers, $\mu_{eff}$ is the effective carrier mobility, V is the applied bias, $V_{bi}$ is the built-in voltage, and L is the thickness of the active layer. The mobilities of hole and electron were extracted from the $J^{1/2}$-V characteristics of the single-carrier diodes (Figure S17 in Supporting Information of [42] or the priority application U.S. Provisional Patent Application No. 62/866,797). The $\mu_{eff}$ is calculated to be 1.74×10$^{-4}$ cm$^2$ V$^{-1}$ s$^{-1}$, which corresponds to a $\tau_{tr}$ of 1.82 μs and a calculated fir of 306 kHz. This value is fairly close to the experimentally determined value of ~240 kHz. The cutoff frequency is comparable to some other OPDs and is more than enough for applications such as image sensors and medical monitoring.[2,40]

g. Application

As a preliminary assessment of the practical application of the NIR OPDs, we carried out a simple photoplethysmography (PPG) test using our OPDs. One of the functions of PPG, a low-cost non-invasive optical technique, is monitoring the pulse and determining the heart rate (HR). The basic working principle is presented in FIG. 10d. The light emitted from the LEDs is partially absorbed, reflected and/or scattered by human tissues, which can be detected by an optical sensor. As a result of the change in blood volume upon each cardiac cycle, the pulsatile ('AC') signal which is superimposed with various low-frequency signals, can be extracted to evaluate the heart rate.[2,41] FIG. 10e shows the set-ups of the HR measurement, which was conducted in the dark to minimize background signal from the surroundings. The HR of a volunteer was measured at his resting and after-exercise conditions, respectively (FIG. 10f). In both cases, the typical systolic and diastolic peaks in a PPG profile can be identified. By dividing 60 s by the averaged inter-beat interval (IBI) in each case, the HR was determined to be 67 and 106 beats per minute for the volunteer at resting and after-exercise conditions, respectively.

h. Materials Synthesis and Characterizations for the Second Example

All reagents and chemicals were purchased from commercial sources and used without further purification. The donor polymer, PTB7-Th, was purchased from 1-Materials (Lot No. SX-8015A, molecular weight ~120 k). The acceptor material CO1-4Cl was synthesized according to our previous work with a slight modification (Figure S1 in Supporting Information of [42] or the priority application U.S. Provisional Patent Application No. 62/866,797).W Compound 1 and 2 were prepared according to previous works with slight modifications.[1,2] A mixture of compound 1 (200 mg, 0.23 mmol) and 2-(5,6-dichloro-3-oxo-2,3-dihydro-1H-inden-1-ylidene)malononitrile, compound 2, (244 mg, 0.93 mmol), dry chloroform (20 mL), and pyridine (0.5 mL) was added into to a flame-dried and nitrogen-filled one-neck round-bottom flask (50 mL). The flask was purged with $N_2$ for 20 min and the reactants were heated to 60° C. for 5 h. After the mixture cooled to room temperature, the reaction mixture was concentrated in vacuum. The residue was purified by silica gel column chromatography (n-hexane/chloroform, 2/8) to afford the product as a dark green solid (210 mg, 67%).

11-1 nuclear magnetic resonance (NMR) spectrum was recorded on a Varian Unity Inova 500 MHz spectrometer in deuterated chloroform solution ($CDCl_3$) with 0.003% TMS as internal reference. Mass spectrum was collected from a matrix-assisted laser desorption ionization-time of flight (MALDI-TOF) mass spectrometer (Bruker Microflex) with 1,8-Dihydroxy-9(10H)-anthracenone (Dithranol) as a matrix recorded in a (+)-reflector mode.

Cyclic Voltammetry (CV) experiment was conducted on a CHI-730B electrochemistry workstation with the three-electrodes system consisting of glassy carbon disk, Pt wire, and Ag wire electrode which serve as the working electrode, counter electrode, and pseudo reference electrode, respectively. The measurement was performed in 0.1 M tetrabutylammonium hexafluorophosphate (n-$Bu_4NPF_6$)-anhydrous acetonitrile solution at a potential scan rate of 100 mV $s^{-1}$. Thin film of the sample was deposited onto the glassy carbon working electrode from its 5 mg $mL^{-1}$ chloroform solution. The electrochemical onset was determined at the position where the current starts to differ from the baseline. The potential of Ag pseudo reference electrode was internally calibrated relative to Fc/Fc+ couple (−4.88 eV vs. vacuum).

The thin film absorption spectra of the PTB7-Th, CO1-4Cl and the BHJ blend were taken from on a LAMBDA 750 UV/Vis/NIR spectrophotometer (Perkin Elmer). The films were spun from chlorobenzene solution onto UV ozone-treated glass substrates. All topographic surface morphology measurements were obtained from an Asylum MFP-3D operating in closed loop mode mounted atop an Olympus inverted optical microscope under an inert atmosphere, using the as-prepared OPD devices as the samples to probe the morphology of the BHJ layer. Pt/Cr coated silicon AFM tips with a resonant frequency of ~13 kHz and a force constant of ~0.2 N $m^{-1}$ were used (Budget Sensors). First-order image flattening and subsequent image analysis were performed on the morphology images on Asylum Research AFM software version 14, programmed using IGOR Pro.

The GIWAXS measurement was conducted at the Advanced Light Source at Lawrence Berkeley National Lab on the 7.3.3 beamline. The sample was scanned with an incidence angle of 0.12° and a photon energy of 10 keV (λ=1.24 Å), while under a helium environment to minimize beam damage and reduce air scattering. The width of the incident X-ray beam is about 1 mm, and silver behenate was used to calibrate the lengths in the reciprocal space. A 2D detector (PILATUS 2 M from Dectris) with a sample-to-detector distance of 276.9 mm was used to collect the images. The Nika software package for Igor (by Wavemetrics) and the Igor script WAXStools were used to process the image.

Device Fabrication and Characterizations

Pre-patterned indium tin oxide (ITO) substrates were ultrasonicated in deionized water, acetone and 2-propanol for 10 min, respectively. The zinc oxide layer was prepared from a diethyl zinc and tetrahydrofuran solution (1:2, v/v) spun onto the cleaned ITO substrates at 4000 rpm for 15 s and annealed at 110° C. for 15 min. This process was done twice. Subsequently, the donor-acceptor blend solution of PTB7-Th:CO1-4Cl (1:1.5 weight ratio) in chlorobenzene:1-chloronaphthalene (98:2, v/v) with different concentrations of 15 g $L^{-1}$ and 35 g $L^{-1}$ was deposited by spin-coating at 1000 rpm, followed by vacuum deposition (<$10^{-6}$ torr) of 15 nm $MoO_x$ and 100 nm Ag to form the electron blocking layer and the anode electrode. The effective device area was 0.0451 $cm^2$. For normal structure devices, the processing conditions for cleaning substrate and active layer deposition are the same as in the inverted structure devices. Commercial solution of poly(3,4-ethylenedioxythiophene)polystyrene sulfonate (PEDOT:PSS, Ossila Al 4083) was spun on the cleaned ITO substrates at 2500 rpm, followed by annealing at 120° C. for 20 min before deposition of the active layer. Then, layers of 5 nm barium and 100 nm aluminum were consecutively deposited under vacuum onto the active layer by thermal evaporation. For the single carrier diodes, 35 g $L^{-1}$ donor-acceptor solution was used for deposition of the active layer under the same condition as in fabricating the photodetectors. To make the hole-only diodes, the blend solution was spun on the PEDOT:PSS-covered ITO substrates and the top electrode was 7 nm MoOx and 100 nm Ag thermally evaporated onto the active layer. For the electron-only diodes, the deposition of ZnO layer and BHJ layer on the ITO substrates were prepared in the same way as in the photodetector devices. To make the top electrode, aluminum-doped ZnO nanoparticle ink in 2-propanol (Sigma-Aldrich) was spun onto the active layer at 4000 rpm for 15 s, followed by thermal evaporation of 100 nm Al. The current-voltage characteristics were measured with a Keithley 4200 semiconductor characterization system. The EQE measurements were performed with a setup of 75-watt Xeon light source coupled with a monochromator and an optical chopper, calibrated with a reference photodiode (NIST-calibrated Newport 818-UV Si photodiode). The photocurrent was recorded with an SR810 DSP lock-in amplifier (Stanford Research System) at 155 Hz. The noise measurements of the devices were done in the dark employing a battery-powered pre-amplifier (SRS 570) coupled with an oscilloscope (Keysight DSOX3022T) operated with fast Fourier transform analysis. For linear dynamic range measurement, a set of 940 nm LEDs were used as the light source and a series of calibrated filters were used to modulate the incident light intensity. The transient photoresponse measurements were conducted with a 940 nm LED as the light source and a function generator as source of pulse signals. The output of the OPDs were amplified with a pre-amplifier and recorded with an oscilloscope.

Third Example: Bandgap Tailored Nonfullerene Acceptors for Low Energy $E_{loss}$ Near-Infrared Organic Photovoltaics (References Refer to Listing for Third Example)

a. Introduction

Organic semiconductors are characterized by a broad structural diversity that allows fine tuning of optical bandgaps and orbital energy levels, and the ability to be processed into thin, light-weight, and flexible devices.[1-5] Near-infrared (NIR) responsive organic semiconductors have the potential for integration into building windows, greenhouse rooftops, and automobile glass as semitransparent energy generating modules,[6-9] as well as optical sensors for health monitoring, image sensing, and night surveillance.[10-12] Rational design of high performance organic semiconductors with NIR absorption capabilities in bulk heterojunction (BHJ) organic solar cells (OSCs) provides interesting challenges,[13-15] and in particular how to best accommodate the inherent trade-off between the driving force for charge separation and voltage loss in the device.[16-20] Careful consideration must be given to the frontier molecular orbitals and energetic offsets in the components of the BHJ blend to efficiently dissociate photo-generated excitons and achieve the highest possible open-circuit voltage ($V_{OC}$).[21-23]

Nonfullerene acceptors (NFAs) with MR absorption for BHJ blends have attracted recent interest.[24-26] They benefit from the structural diversity offered by multiple combinations of ladder-type central donor (electron rich) and acceptor (electron poor) end groups; this feature has endowed acceptor-donor-acceptor (A-D-A) type NFAs with narrow bandgap properties and provided energetics suitable for NIR solar cell fabrication.[27-30] NFAs with ultra-narrow bandgap (UNBG) properties (defined arbitrarily as $E_g^{opt} \leq 1.3$ eV) have also been successfully designed.[31-36] Of note is that the design of UNBG-NFAs has led to short-circuit current densities ($J_{SC}$) of over 20 mA cm$^{-2}$ due in part to a broad photoresponse in the NIR region. Incorporating π-bridge units (D' or D") to form an A-D'-D-D'(D")-A configuration provides further opportunities to optimize intramolecular charge transfer (ICT) characteristics, energy levels, and BHJ morphology.[32,37-39] It is also encouraging that driving energies for efficient charge separation in NFA solar cells are smaller than empirical 0.3 eV observed in fullerene-based OSCs,[40-44] which is advantageous to minimize energy losses from the difference between optical bandgap ($E_g^{opt}$) and $V_{OC}$ of the solar cell device ($E_{loss} = E_g^{opt} - eV_{OC}$); this enables high photocurrents and high voltage to be achieved simultaneously, particularly in UNBG heterojunctions.[22,34]

b. Structure and Synthesis

In this example, we disclose a series of A-D'-D-D'-A symmetric and A-D'-D-D"-A asymmetric type NFAs with UNBG properties for use in NIR solar cell applications. Our molecular design includes structural variations through side chain engineering for the purpose of tuning molecular symmetry and desirable properties. Consequently, p-IO1, o-IO1, p-IO2, and o-IO2 are constructed based on an indaceno[1,2-b:5,6-b']dithiophene (IDT) central core (D), thienyl π-bridges (π), and 1,1-dicyanomethylene-5,6-difluoro-3-indanone terminal electron poor fragments (A), see FIG. 11. These molecules possess identical conjugated framework skeletons, but differ with respect to the solubilizing side chains, specifically alkyl vs. alkoxy on the π-bridges and octyl vs. 4-hexylphenyl on the D core. One finds that replacing bulky hexylphenyl chains (p-IO2 and p-IO1) with linear octyl chains (o-IO2 and o-IO1) on the D core leads to improved packing ability and decreases the optical bandgap. By changing the number of alkoxy groups on the thienyl π-bridges, one can modulate intramolecular charge transfer (ICT) characteristics. Devices fabricated using the non-symmetric o-IO1, which bears linear octyl chains on the IDT central core and alkyl and alkoxy chains on the thienyl π-bridges, in combination with the donor conjugated polymer PTB7-Th are able to achieve a power conversion efficiency PCE of 13.1% with a short circuit current ($J_{SC}$) of 26.3 mA cm$^{-2}$ and $E_{loss}$=0.54 eV.

Synthetic routes for the preparations of p-IO1, o-IO1, p-IO2, and o-IO2 are provided in Scheme 2 below. The key intermediates (4a, 4ab, 5a, and 5b) were synthesized by Stille coupling of bis(stannyl) IDT (1a or 1b) and monobromo thienyl π-bridges with alkyl and alkoxy side chains (2 and 3). Knoevenagel condensation of dialdehyde precursors (4a, 4b, 5a, and 5b) with 1,1-dicyanomethylene-5,6-difluoro-3-indanone afforded the target NFAs: p-IO1, o-IO1, p-IO2, and o-IO2 in yields of >80%. All new compounds and intermediates were characterized by conventional methods, see further synthesis details in section d.

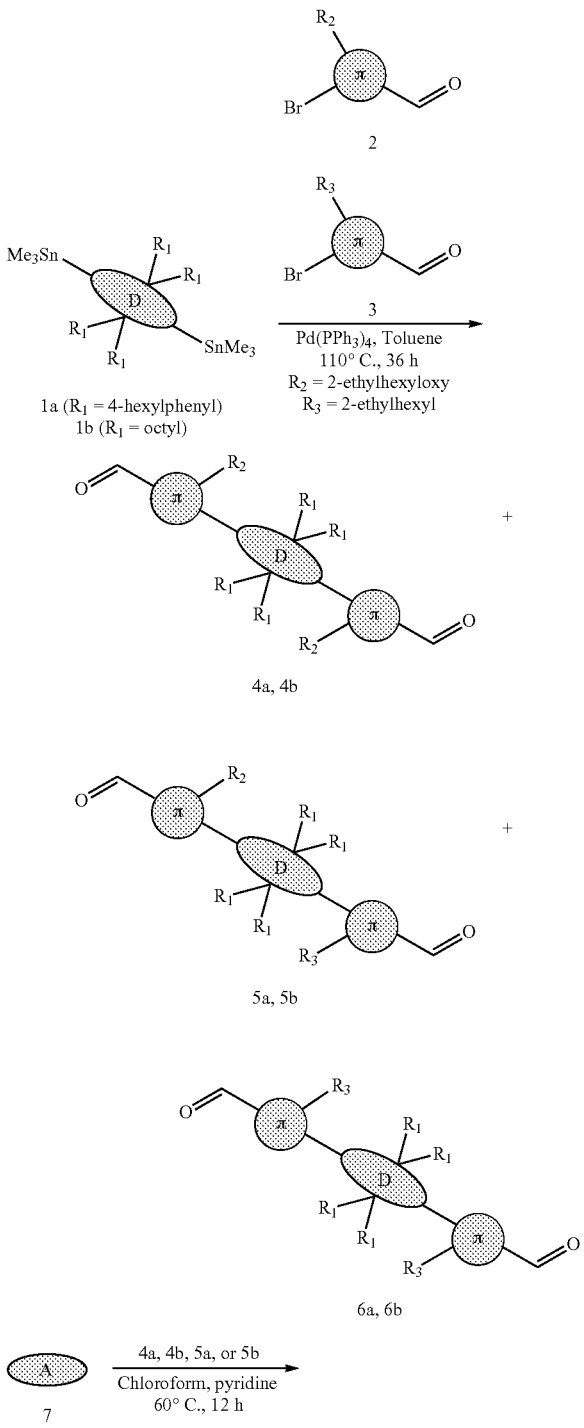

Scheme 2 Synthetic procedure for the preparations of p-IO2, o-IO2, p-IO1, and o-IO1.

-continued

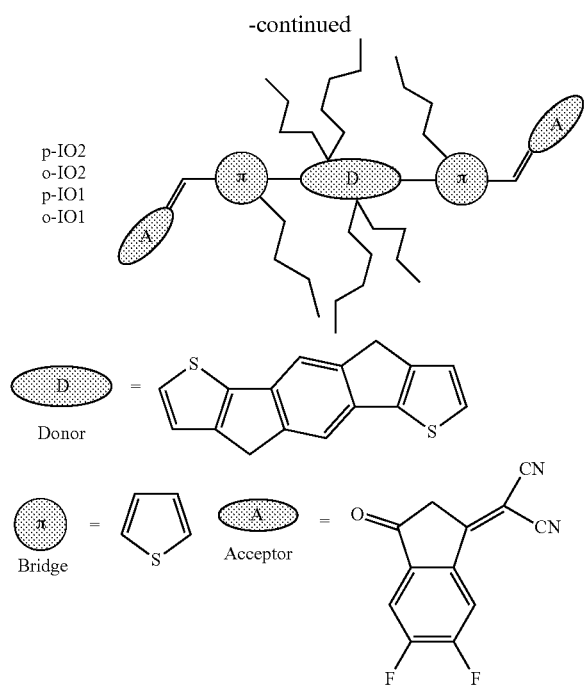

p-IO2
o-IO2
p-IO1
o-IO1

Donor

Bridge

Acceptor c. Experimental Data

The optical absorption spectra of p-IO2, p-IO1, o-IO2, and o-IO1 in dilute chloroform solutions are provided in FIG. 11b. One observes that the absorption maximum (Amax) red-shifts gradually from 766 nm (p-IO1) to 790 nm (o-IO1) to 808 nm (p-IO2), and then to 835 nm (o-IO2); the $\lambda_{max}$ red-shifts approximately ~25 nm by replacing bulky phenylhexyl with linear octyl chains on D and ~45 nm by replacing alkyl with alkoxy chains on 7C, respectively. The molar extinction coefficient ($\varepsilon_{max}$) of o-IO1 was calculated to be $1.32 \times 10^5$ $M^{-1}$ $cm^{-1}$, which is slightly larger than that of p-IO1 ($1.20 \times 10^5$ $M^{-1}$ $cm^{-1}$). A similar trend was observed with their analogues: o-IO2 vs. p-IO2 ($1.70 \times 10^5$ $M^{-1}$ $cm^{-1}$ vs. $1.59 \times 10^5$ $M^{-1}$ $cm^{-1}$). From the UV-vis-NIR absorption spectra of NFAs as thin films shown in FIG. 11c one observes absorption capabilities in the range of 600-1050 nm, with the maxima located at 815, 850, 880, and 920 nm for p-IO1, o-IO1, p-IO2, and o-IO2, respectively. The red-shifted wavelengths from solution to thin films are approximately 49 nm, 60 nm, 72 nm, and 85 nm for p-IO1, o-IO1, p-IO2, and o-IO2, respectively, leading to optical bandgaps of 1.34 eV (p-IO1), 1.28 eV (o-IO1), 1.24 eV (p-IO2), and 1.20 eV (o-IO2) as determined from the onset of film absorption according to the relationship $E_g^{opt*} = 1240/\lambda_{edge}$. We conclude from these comparative studies that incorporating linear octyl instead of bulky phenylhexyl side chains leads to a red-shifted $\lambda_{max}$. For instance, compare the $\lambda_{max}$ of o-IO2 (920 nm) vs. p-IO2 (880 nm). Replacing alkoxy side chains with alkyl side chains at the thienyl π-bridges leads to a blue-shifted Amax (o-IO2 (920 nm) vs. o-IO1 (850 nm)), most likely due to a reduction in the electron density in the interior of the molecular skeleton and concomitant weakening of the intramolecular charge transfer (ICT). From a practical perspective, it is worth noting the complementary absorption spectra and orbital energy levels between the NFAs and PTB7-Th for achieving broad absorption of sunlight (Table 4). Highest occupied molecular orbital (HOMO) and lowest unoccupied molecular orbital (LUMO) levels were estimated by using cyclic voltammetry (Table 4), and their cyclic voltammograms are shown in FIG. 12e. Altogether, the optical absorption and molecular orbital level results provide the framework to appreciate the degree to which permuting the side chains can be used to modulate the optoelectronic properties built within this specific conjugated ICT core.

Solar cells with the inverted device structure comprising ITO/ZnO/PTB7-Th:NFA/MoO$_3$/Ag were fabricated to investigate photovoltaic performances. Multiple factors were taken into consideration when optimizing performance, including concentration and composition of photoactive layer materials, spin-casting rate, and the use of a processing additive. Best performances were achieved by using a weight ratio of 1:1.5 for PTB7-Th:NFA (total 18 mg $mL^{-1}$) with chlorobenzene (CB) as the main processing solvent and 1-chloronaphthalene (CN) as a solvent additive. The photovoltaic data of the best devices are listed in Table 5; optimization details are described in section d, see FIG. 12g-k and Table 6.

TABLE 4

Optical properties and estimates of frontier energy levels of PTB7-Th, p-IOl, o-IOl, p-IO2, and o-IO2.

| Compound | $\lambda_{fmax}$ (nm)[a] | $\lambda_{fmax}$ (nm)[b] | $E_g^{opt}$ (eV)[c] | HOMO (eV)[d] | LUMO (eV)[e] |
|---|---|---|---|---|---|
| PTB7-Th |  | 705 | 1.58 | -5.20 | -3.46 |
| p-IO1 | 766 | 815 | 1.34 | -5.46 | -4.13 |
| o-IO1 | 790 | 850 | 1.28 | -5.44 | -4.15 |
| P-IO2 | 808 | 880 | 1.24 | -5.44 | 4.19 |
| o-IO2 | 835 | 920 | 1.20 | -5.41 | -4.21 |

[a]Absorption maximum in solution.
[b]Absorption maximum in thin film.
[c]Optical bandgap calculated from the absorption edge of the thin film.
[d]HOMO energy level estimated from the oxidation onset potential.
[e]LUMO energy level estimated from the potential of the reduction

TABLE 5

Photovoltaic performances of OSCs based on PTB7-Th and four NFAs measured under simulated 100 mW $cm^{-2}$ AM 1.5 G illumination.

| NFA[a] | $V_{OC}$ (V) | $J_{SC}$ (mA $cm^{-2}$) | Cal. $J_{SC}$ (mA $cm^{-2}$)[b] | FF | $PCE_{max\ (ave)}$ (%)[c] | $E_{loss}$ (eV) |
|---|---|---|---|---|---|---|
| p-IO1 | 0.78 | 22.3 | 21.9 | 0.62 | 10.8 (10.34 ± 0.35) | 0.56 |
| o-IO1 | 0.74 | 26.3 | 24.7 | 0.67 | 13.1 (12.57 ± 0.44) | 0.54 |
| p-IO2 | 0.70 | 23.0 | 22.6 | 0.67 | 10.8 (10.24 ± 10.38) | 0.54 |
| o-IO2 | 0.68 | 21.8 | 20.0 | 0.63 | 9.3 (9.14 ± 0.17) | 0.52 |

[a]PTB7-Th:acceptor blend ratios are 1:1.5 (w/w). 2-3 vol % CN was used as a processing solvent additive.
[b]Calculated by integrating the EQE spectra.
[c]The average PCE values were obtained from over 12 devices.

FIG. 12a presents current density-voltage (J-V) characteristics of the optimized solar cells prepared with CB:CN (2 vol % for p-IO2, o-IO1, o-IO2 and 3 vol % for p-IO1, respectively). Optimized devices with p-IO1, o-IO1, p-IO2, and o-IO2 showed maximum PCEs ($PCE_{max}$) of 10.8%, 13.1%, 10.8%, and 9.3% with $J_{SC}$ values of 22.3 mA·$cm^{-2}$, 26.3 mA·$cm^{-2}$, 23.0 mA·$cm^{-2}$, and 21.8 mA·$cm^{-2}$, respectively. Devices with p-IO1, o-IO1, p-IO2, and o-IO2 show $V_{OC}$ values of 0.78 V, 0.74 V, 0.70 V, and 0.68 V, respectively, which follow expectations anticipated by examination of the energy differences between the LUMO of NFAs and the HOMO of PTB7-Th in FIG. 12e-f.

From the external quantum efficiencies (EQEs) of solar cells provided in FIG. 12b we observe that the devices exhibit broad photo responses ranging from 300 nm to 1000 nm, but reach EQE values of ~80% in the NIR region, in accordance with the absorption profiles of the active layer components. The $J_{SC}$ integrated from EQE curves agrees with the values obtained from the J-V curves. Being aware of the challenge to achieve high EQEs and high $V_{OC}$ simultaneously in NIR OSCs, we provide in FIG. 12c a plot of $EQE_{max}$ vs. $E_{loss}$ using values reported in the literature.

State-of-the-art nonfullerene solar cells have achieved $E_{loss}$ in the range of 0.5-0.6 eV with high EQEs (>70%), whereas most devices with $PC_{71}BM$ exhibit $E_{loss}$ values larger than ~0.7 eV (FIG. 12c).[45-48] We demonstrated that low energy loss of 0.49 eV and high $EQE_{max}$ of 78% can be achieved simultaneously in a previous study.[22] In this work, the as of the optimized devices is ranging from 0.52 eV to 0.56 eV. It should be noted that the PTB7-Th:o-IO1 device exhibits an $E_{loss}$ as low as 0.54 eV and $EQE_{max}$ of 85% with EQE responses over 80% from 700 nm to 840 nm. This indicates that an excellent compromise between exciton dissociation/charge transfer and voltage loss was attained in the PTB7-Th:o-IO1 device, thus leading to a PCE of 13.1% with a $J_{SC}$ of 26.3 mA·cm$^{-2}$ and a $V_{OC}$ of 0.74 V. FIG. 2d summarizes the correlation of $eV_{OC}$ with $E_g^{opt}$ using literature values. The majority of the devices exhibit as of over 0.6 eV and only a few cases with UNBG properties ($E_g^{opt}$<1.3 eV) have been demonstrated. We have thus successfully developed UNBG-NFAs, enabling low as NIR organic solar cells.

To obtain insight into the self-assembly of the BHJ components, grazing incidence wide-angle X-ray scattering (GIWAXS) was employed on films of the pure components and blends. Single component, p-IO1, o-IO1, p-IO2, and o-IO2, thin films processed with CB were first measured. From the 2D GIWAXS patterns (see FIG. 13 g-j), one observes that the octyl-substituted o-IO1 and o-IO2 crystallites exhibit a preferential edge-on orientation relative to the substrate, whereas the hexylphenyl-substituted p-IO2 orients face-on. There is a larger number of diffraction peaks with o-IO2 compared to o-IO1. This is probably because o-IO2 with its symmetrical configuration has a higher tendency to crystallize in highly ordered domains, at least relative to the asymmetrical o-IO1.[32,49,50] A similar tendency in crystallization for the symmetric vs. asymmetric structures can be observed for p-IO2 and p-IO1. The p-IO1 film exhibits the weakest crystallization tendency among the four components in this study, probably as a result of the combination of the bulky alkylphenyl side chains and the asymmetrical configuration. Processing with CN additive encourages the four NFA molecules to be organized with face-on orientations. Clear diffraction peaks along the out-of-plane direction were observed for p-IO1, o-IO1, p-IO2, and o-IO2 with π-π stacking distances of 3.44 Å, 3.42 Å, 3.41 Å, and 3.40 Å, respectively. The slight contraction of packing distance is in accordance with the general crystallization features mentioned above.

The 2D GIWAXS images of the PTB7-Th:NFA blends processed with CN are shown in FIG. 13 a-f. The crystallization propensity and molecular orientation of the blends with four NFAs follow the trends observed in the neat NFA films processed with CB:CN. The intensities of peaks around $q_{xy}$=0.325 Å$^{-1}$ and $q_z$=1.83 Å$^{-1}$ assigned to the NFA lamella (d-spacing: 19.3 Å) and π-π stacking (d-spacing: 3.43 Å) respectively, became weaker from o-IO2 to p-IO2 to o-IO1 to p-IO1 (FIGS. 13e and 13f). Consequently, the PTB7-Th:o-IO2 blends are dominated by the diffraction features of o-IO2 crystallites, whereas p-IO1 in the blends are relatively featureless.

We also examined the CB:CN-processed PTB7-Th:NFA blend films by using transmission electron microscopy (TEM). From FIG. 14, we observe that phase separation and domain size become larger as the crystallization propensity of the molecules increases according to the order p-IO1<o-IO1<p-IO2<o-IO2. Smallest apparent phase separation was observed in the PTB7-Th:p-IO1 blend. PTB7-Th:o-IO1 retains well-mixed phases with a slight increase in domain size. This indicates that non-symmetrical molecules tend to favor intermixing with PTB7-Th, thereby facilitating exciton dissociation. Highest degree of phase separation is observed in the PTB7-Th:o-IO2 films (FIG. 14d). It is possible to assign the dark grain-shape aggregates to the o-IO2-rich phases by electron energy loss spectroscopy (EELS) because only NFA molecules contain nitrogen atoms (see FIG. 14 e-g). The higher crystallization propensity of the o-IO2 molecules induced by symmetrical configuration[49] and linear octyl side chains[51,52] leads to larger aggregates growth. Despite a broader absorption spectrum, the EQE responses of PTB7-Th:o-IO2-based device in the NIR region were lower than those of the devices based on the other NFAs (FIG. 12b). This we attribute the decreased interfacial area in the PTB7-Th:o-IO2 blend, a less favorable situation for charge generation.

As illustrated herein, we successfully synthesized a series of A-D'-D-D'-A and A-D'-D-D"-A type UNBG-NFAs, featuring efficient NIR photovoltaic properties with low $E_{loss}$. Modulating ICT effect by side chain modification of UNBG-NFAs enables tailoring of bandgaps and energetics, so as to optimize the energy diagram with respect to polymer PTB7-Th and thus to achieve highest possible $V_{OC}$ values. Combination of linear octyl-substitution and non-symmetrical configuration in o-IO1 yields ordered crystallites and formation of suitable BHJ morphology with PTB7-Th, leading to the large photocurrent generation of the devices. Notably, the efficiency over 13% is one of the highest PCEs for the devices featuring UNBG properties ($E_g^{opt}$≤1.3 eV). The molecular design strategy described here has the potential to be applied in the design of other electron acceptor materials.

d. Supplemental Information for the Third Example

Materials All reagents and chemicals were purchased from commercial sources and used without further purification. All anhydrous organic solvents for the synthesis, characterization, and device fabrication steps were purchased from Sigma-Aldrich and TCI. Compound 1a, 1b, 2, 3, and 7 were prepared via a modified synthetic condition from literature.[1-4]

Characterizations of compounds $^1$H and $^{13}$C NMR spectra of intermediate monomers were recorded on a Varian Unity Inova 500 MHz spectrometer in deuterated chloroform solution (CDCl$_3$) with 0.003% TMS as internal reference. Ultraviolet-Visible-Near-infrared (UV-Vis-NIR) absorption spectra were recorded on a Perkin Elmer Lambda 750 spectrophotometer. For the measurements of thin films, materials were spun coated onto precleaned glass substrates from chloroform solutions (10 mg mL$^{-1}$). Optical band gap was determined from the absorption onset of thin film sample.

Film microstructure characterization Transmission electron microscopy (TEM) images were obtained using JEOL JEM-2200FS (with Image Cs-corrector).

Electrochemical characterization The electrochemical cyclic voltammetry (CV) was conducted on a CHI-730B electrochemistry workstation with glassy carbon disk, Pt wire, and Ag/Ag+ electrode as the working electrode, counter electrode, and reference electrode, respectively in a 0.1 M tetrabutylammonium hexafluorophosphate (n-Bu$_4$NPF$_6$) anhydrous acetonitrile solution at a potential scan rate of 40 mV s$^{-1}$. Thin films of samples were deposited onto the glassy carbon working electrode from a 3 mg mL$^{-1}$ chloroform solution. The electrochemical onsets were determined at the position where the current starts to differ from the baseline. The potential of Ag/AgCl reference electrode was internally calibrated by using the ferrocene/ferrocenium redox couple (Fc/Fc$^+$).

Grazing incidence wide angle X-ray scattering (GIWAXS) analysis 2D GIWAXS measurements were performed using Beamline 9A at the Pohang Accelerator Laboratory (PAL). The photon energy is 11.055 keV ($\lambda$=1.1214 Å). The angle between the film surface and the incident beam was fixed at 0.12° for all of the samples. The measurements were obtained at scanning intervals of 2θ between 3° and 25°. The 2D GIWAXS images from the films were analyzed according to the relationship between the scattering vector q and the d spacing, q=2π/d. The GIWAXS images shown are normalized with respect to exposure time.

Fabrication and characterization of solar cell The solar cell devices were fabricated followed by these procedures. First, the ITO-coated glass substrates were cleaned with detergents, then sonicated in acetone and isopropyl alcohol and dried in an oven at 130° C. The zinc oxide (ZnO) solution was prepared using mixture of diethyl zinc and tetrahydrofuran (THF) (1:2, v/v %) and the ZnO film (35 nm) was prepared from spin-casting at 4000 rpm for 15 s and annealing at 110° C. for 15 min.[5,6] For deposition of the active layer, blend solutions of PTB7-Th (1 wt %):NFA (1.5 wt %) (total 18 mg/mL) dissolved in CB (with 2 vol % 1-chloronaphthalene) were spin-coated on top of the ZnO layer in a nitrogen-filled glove box. The device was pumped down in vacuum (<10-6 torr; 1 torr~133 Pa), and a 7 nm thick MoO$_3$/100 nm thick Ag electrode for our device architecture were deposited on top of the active layer by thermal evaporation. Photovoltaic characteristics measurements were carried out inside the glove box using a high quality optical fiber to guide the light from the solar simulator equipped with a Keithley 2635A source measurement unit. J-V curves were measured under AM 1.5G illumination at 100 mW cm$^{-2}$ using an aperture (9.4 mm$^2$) to define the illuminated area. EQE measurements were conducted in nitrogen-filled glove box using an EQE system. The monochromatic light intensity was calibrated using a Si photodiode and chopped at 100 Hz.

Material Synthesis The general procedure for the synthesis of bisaldehyde intermediates (compound 4a, 4b, 5a, and 5b) is described as follows. A mixture of compound 1a (or 1b), 5-bromo-4-(2-ethylhexyloxy)thiophene-2-carbaldehyde (compound 2), 5-bromo-4-(2-ethylhexyl)thiophene-2-carbaldehyde (compound 3), Pd(PPh$_3$)$_4$ (5 mol %), and dry toluene:DMF (20:5 mL) were added into a flame-dried and nitrogen-filled one-neck round-bottom flask. The flask was purged with N$_2$ for 10 min and the reactant was heated to 120° C. for 36 h. After the mixture cooled to room temperature, DI water was added, and the mixture was extracted with dichloromethane. The organic layer was dried over MgSO$_4$ and concentrated in vacuum. The residue was purified by silica gel column chromatography.

Compound 4a and 5a: Compound 1a (1 g, 0.81 mmol), compound 2 (310 mg, 0.97 mmol), compound 3 (295 mg, 0.97 mmol), and Pd(PPh$_3$)$_4$ (47 mg) were used for the reaction. The crude product was purified by silica gel column chromatography (n-hexane:ethyl acetate, 9:1) to afford 4a as a deep orange solid (292 mg, 26%), 5a as an orange solid (355 mg, 32%), and 6a as a sticky yellow solid (252 mg, 23%), respectively.

$^1$H NMR for compound 4a (500 MHz, CDCl$_3$, ppm): δ 9.73 (s, 2H), 7.44 (s, 2H), 7.42 (s, 2H), 7.37 (s, 2H), 7.16-7.18 (d, 8H), 7.06-7.08 (d, 8H), 4.05-4.06 (d, 4H), 2.56 (t, 8H), 1.80 (m, 2H), 1.39-1.62 (m, 12H), 1.24-1.38 (m, 36H), 0.94 (t, 6H), 0.84-0.90 (m, 18H).

$^1$H NMR for compound 5a (500 MHz, CDCl$_3$, ppm): δ 9.82 (s, 1H), 9.75 (s, 1H), 7.54 (s, 1H), 7.48 (s, 1H), 7.46 (d, 2H), 7.41 (s, 1H), 7.17-7.24 (m, 8H), 7.08-7.14 (m, 8H), 4.08 (d, 2H), 2.75 (d, 2H), 2.55-2.64 (m, 8H), 1.78-1.86 (m, 1H), 1.66-1.74 (m, 1H), 1.42-1.66 (m, 12H), 1.21-1.41 (m, 36H), 0.96 (t, 3H), 0.81-0.91 (m, 21H).

Compound 4b and 5b: Compound 1b (800 mg, 0.77 mmol), compound 2 (295 mg, 0.92 mmol), compound 3 (279 mg, 0.92 mmol), and Pd(PPh$_3$)$_4$ (44 mg) were used for the reaction. The crude product was purified by silica gel column chromatography (n-hexane:ethyl acetate, 9:1) to afford 4b as a deep orange solid (257 mg, 28%), 5b as an orange solid (307 mg, 34%), and 6b as a sticky yellow solid (231 mg, 26%), respectively.

$^1$H NMR for compound 4b (500 MHz, CDCl$_3$, ppm): δ 9.76 (s, 2H), 7.49 (s, 2H), 7.38 (s, 2H), 7.26 (s, 2H), 4.11 (q, 4H), 1.95-2.04 (m, 4H), 1.83-1.91 (m, 6H), 1.58-1.69 (m, 6H), 1.49-1.55 (m, 2H), 1.36-1.44 (m, 8H), 1.06-1.23 (m, 36H), 1.01 (t, 6H), 0.96 (t, 6H), 0.90 (br, 4H), 0.80 (t, 18H).

111 NMR for compound 5b (500 MHz, CDCl$_3$, ppm): δ 9.84 (s, 1H), 9.76 (s, 1H), 7.57 (s, 1H), 7.49 (s, 1H), 7.38 (s, 1H), 7.27 (d, 2H), 7.17 (s, 1H), 4.11 (q, 2H), 2.80 (d, 2H), 1.95-2.05 (m, 4H), 1.83-1.93 (m, 5H), 1.73 (m, 1H), 1.56-1.68 (m, 3H), 1.47-1.55 (m, 1H), 1.23-1.45 (m, 12H), 1.05-1.25 (m, 40H), 1.01 (t, 6H), 0.96 (t, 6H), 0.77-0.93 (m, 24H). $^{13}$C NMR (125 MHz, CDCl$_3$): 182.43, 181.51, 155.73, 155.71, 153.66, 153.40, 152.97, 143.98, 143.47, 143.08, 139.76, 139.66, 138.98, 136.21, 136.11, 135.78, 135.55, 135.30, 127.89, 123.52, 122.19, 120.04, 113.41, 113.29, 74.27, 54.22, 54.00, 39.84, 39.73, 39.09, 39.04, 33.71, 32.52, 31.76, 30.57, 29.96, 29.92, 29.30, 29.26, 29.20, 29.17, 29.10, 29.03, 28.67, 25.66, 24.25, 24.17, 23.94, 23.05, 23.03, 22.56, 14.12, 14.06, 14.02, 11.19, 10.60.

The general procedure for the synthesis of final products (p-IO1, o-IO1, p-IO2, and o-IO2) is described as follows. A mixture of bisaldehyde intermediate 4a (4b, 5a, or 5b), 2-(5,6-difluoro-3-oxo-2,3-dihydro-1H-inden-1-ylidene)malononitrile (compound 7), dry chloroform (20 mL), and pyridine (0.5 mL) was added into to a flame-dried and nitrogen-filled one-neck round-bottom flask (50 mL). The flask was purged with N$_2$ for 20 min and the reactant was heated to 60° C. for 12 h. After the mixture cooled to room temperature, the reaction mixture was concentrated in vacuum. The residue was purified by silica gel column chromatography (n-hexane/chloroform, 2/8).

p-IO1: Compound 5a (270 mg, 0.20 mmol) and compound 7 (227 mg, 0.99 mmol) were used for the reaction. The crude product was purified by using silica gel column chromatography (n-hexane:chloroform, 2:8) to afford p-IO1 (301 mg, 85%).

$^1$H NMR (500 MHz, CDCl$_3$, ppm): δ 8.75 (s, 1H), 8.68 (s, 1H), 8.48-8.55 (m, 2H), 7.61-7.67 (m, 4H), 7.50 (d, 2H), 7.47 (s, 2H), 7.18-7.22 (m, 8H), 7.10-7.14 (m, 8H), 4.11 (d, 2H), 2.79 (d, 2H), 2.55-2.63 (m, 8H), 1.83-1.90 (m, 1H), 1.75 (br, 1H), 1.45-1.65 (m, 18H), 1.20-1.40 (m, 42H), 0.80-1.00 (m, 32H).

$^{13}$C NMR (125 MHz, CDCl$_3$): 186.13, 186.07, 158.25, 158.09, 157.79, 157.68, 154.78, 154.74, 154.40, 153.33, 151.26, 149.60, 147.01, 145.62, 142.03, 141.95, 141.07, 140.97, 140.24, 137.93, 137.77, 137.44, 137.00, 136.64, 136.33, 135.92, 135.70, 134.33, 133.92, 131.50, 128.59, 128.56, 127.87, 127.85, 124.63, 123.69, 121.20, 120.70, 118.11, 118.05, 115.04, 114.96, 114.58, 114.29, 114.19, 112.49, 74.68, 69.65, 68.51, 63.18, 62.92, 39.60, 39.33, 35.59, 33.80, 32.43, 31.73, 31.35, 30.51, 29.14, 29.11, 29.04, 28.57, 25.67, 23.88, 23.03, 22.99, 22.59, 14.12, 14.10, 11.13, 10.56.

o-IO1: Compound 5b (300 mg, 0.26 mmol) and compound 7 (235 mg, 1.02 mmol) were used for the reaction. The crude product was purified by using silica gel column chromatography (n-hexane:chloroform, 2:8) to afford o-IO1 (351 mg, 86%).

$^1$H NMR (500 MHz, CDCl$_3$, ppm): δ 8.80 (s, 1H), 8.72 (s, 1H), 8.51-8.57 (m, 2H), 7.65-7.71 (m, 4H), 7.51 (br, 1H), 7.49 (s, 1H), 7.35 (s, 1H), 7.34 (s, 1H), 4.17 (q, 2H), 2.87 (d, 2H), 2.00-2.11 (m, 4H), 1.89-1.98 (m, 5H), 1.81 (m, 1H), 1.64-1.72 (m, 3H), 1.27-1.47 (m, 12H), 1.08-1.24 (m, 42H), 1.04 (t, 3H), 0.99 (t, 3H), 0.88-0.94 (m, 6H), 0.80 (t, 12H).

$^{13}$C NMR (125 MHz, CDCl$_3$): 186.05, 157.99, 157.71, 157.21, 157.06, 155.43, 155.32, 155.22, 155.11, 154.77, 154.66, 154.33, 153.36, 153.32, 153.25, 153.21, 153.16, 153.12, 153.05, 153.01, 152.10, 149.82, 148.62, 146.85, 139.96, 138.74, 137.11, 137.07, 136.66, 136.64, 136.57, 136.48, 136.09, 135.78, 134.38, 134.38, 134.34, 134.24, 134.20, 133.69, 131.22, 129.70, 123.45, 122.63, 120.77, 120.16, 114.92, 114.76, 114.67, 114.58, 114.31, 114.25, 114.05, 113.95, 112.51, 112.36, 112.30, 112.16, 74.74, 69.39, 68.12, 54.46, 54.18, 39.70, 39.29, 39.19, 33.85, 32.53, 31.77, 30.55, 29.98, 29.96, 29.32, 29.30, 29.24, 29.22, 29.11, 28.64, 25.75, 24.28, 23.92, 23.05, 22.57, 14.16, 14.10, 14.03, 11.19, 10.61.

p-IO2: Compound 4a (240 mg, 0.17 mmol) and compound 7 (160 mg, 0.69 mmol) were used for the reaction. The crude product was purified by using silica gel column chromatography (n-hexane:chloroform, 1:9) to afford p-IO2 (IEICO-4F) (254 mg, 81%).

$^1$H NMR (500 MHz, CDCl$_3$, ppm): δ 8.69 (s, 2H), 8.48-8.54 (m, 2H), 7.63 (t, 2H), 7.60 (s, 2H), 7.49 (s, 2H), 7.47 (br, 2H), 7.17 (d, 8H), 7.10 (d, 8H), 4.10 (d, 4H), 2.58 (t, 8H), 1.86 (m, 2H), 1.43-1.65 (m, 16H), 1.24-1.41 (m, 36H), 0.97 (t, 6H), 0.81-0.93 (m, 18H).

o-IO2: Compound 4b (120 mg, 0.10 mmol) and compound 7 (93 mg, 0.40 mmol) were used for the reaction. The crude product was purified by using silica gel column chromatography (chloroform) to afford o-IO2 (130 mg, 80%).

$^1$H NMR (500 MHz, CDCl$_3$, ppm): δ 8.72 (s, 2H), 8.50-8.53 (m, 2H), 7.65-7.67 (m, 4H), 7.51 (br, 2H), 7.33 (s, 2H), 4.17 (s, 4H), 1.99-2.09 (m, 4H), 1.89-1.97 (m, 6H), 1.63-1.72 (m, 6H), 1.44 (m, 5H), 0.95-1.24 (m, 30H), 0.74-0.93 (m, 12H).

153.18, 148.51, 138.69, 136.69, 136.10, 134.35, 122.54, 120.34, 114.94, 114.75, 114.66, 114.01, 112.38, 112.23, 74.71, 68.13, 54.18, 39.73, 39.21, 31.79, 30.61, 29.99, 29.32, 29.25, 29.15, 24.30, 23.98, 23.08, 22.60, 14.18, 14.06, 11.22.

TABLE 6

The detailed photovoltaic performances of the solar cells based on PTB7-Th:NFA with different D:A ratio and additive vol %.

| | D:A Ratio | Solvent System | $V_{OC}$ [V] | $J_{SC}$ [mA cm$^{-2}$] | FF [%] | PCE$_{max}$ [%] |
|---|---|---|---|---|---|---|
| PTB7-TH:p-IO1 | 1:1 | CB | 0.78 | 20.6 | 0.44 | 7.0 |
| | 1:1.5 | CB | 0.77 | 24.4 | 0.55 | 10.3 |
| | | CB:1% CN | 0.77 | 25.6 | 0.51 | 10.0 |
| | | CB:2% CN | 0.77 | 23.4 | 0.56 | 10.5 |
| | | CB:3% CN | 0.78 | 22.3 | 0.62 | 10.8 |
| | | CB:5% CN | 0.78 | 20.6 | 0.67 | 10.7 |
| | 1:2 | CB | 0.78 | 22.9 | 0.53 | 9.5 |
| PTB7-Th:o-IO1 | 1:1 | CB | 0.76 | 21.4 | 0.54 | 8.8 |
| | 1:1.5 | CB | 0.76 | 22.7 | 0.66 | 11.4 |
| | | CB:1% CN | 0.74 | 24.3 | 0.66 | 11.9 |
| | | CB:2% CN | 0.75 | 26.3 | 0.67 | 13.1 |
| | | CB:3% CN | 0.74 | 25.8 | 0.68 | 13.0 |
| | | CB:5% CN | 0.75 | 20.5 | 0.69 | 10.6 |
| | | CB:1% DIO | 0.74 | 19.8 | 0.63 | 9.2 |
| | 1:2 | CB | 0.75 | 21.6 | 0.65 | 10.5 |
| PTB7-Th:p-IO2 | 1:1.5 | CB | 0.74 | 22.0 | 0.59 | 9.5 |
| | | CB:1% CN | 0.70 | 21.6 | 0.67 | 10.0 |
| | | CB:2% CN | 0.70 | 23.0 | 0.67 | 10.8 |
| | | CB:3% CN | 0.70 | 21.3 | 0.69 | 10.2 |
| | | CB:5% CN | 0.70 | 20.7 | 0.65 | 9.4 |
| PTB7-Th:o-IO2 | 1:1 | CB | 0.70 | 10.0 | 0.60 | 4.2 |
| | 1:1.5 | CB | 0.71 | 12.7 | 0.56 | 5.0 |
| | | CB:2% CN | 0.68 | 21.8 | 0.63 | 9.3 |
| | | CB:5% CN | 0.65 | 13.5 | 0.65 | 5.7 |
| | | CB:1% DIO | 0.67 | 4.7 | 0.48 | 1.5 |
| | 1:2 | CB | 0.70 | 8.5 | 0.62 | 3.7 |

Process Steps

FIG. 18 illustrates a method of fabricating a composition of matter. The method comprises the following steps.

Block 1800 represents combining (e.g., performing a Stille coupling reaction between) a first donor compound/moiety D comprising a dithiophene and a second donor compound/moiety (e.g., comprising an alkylthienyl) different from the first donor compound/moiety so as to form a molecule of the structure D-D'.

Block 1802 represents combining (e.g., performing an arylation between) the molecule of structure D-D' and a third donor compound/moiety D" (e.g., comprising alkoxythienyl) different from the second donor compound/moiety D' and the first donor compound/moiety D, so as to form a molecule having the structure D'-D-D".

Block 1804 represents combining (e.g., performing an end capping reaction of) the D'-D-D" molecule with an acceptor compound A (A', or A") so as to form an organic molecule of the structure A-D'-D-D"-A. In one or more examples, A comprises (3-oxo-2,3-dihydro-1H-inden-1-ylidene)malononitrile (IC), fluorinated or chlorinated (3-oxo-2,3-dihydro-1H-inden-1-ylidene)malononitrile, or an acceptor moiety as described herein. In one or more examples, the dithiophene has side chains soluble in a solvent used to solution process the device comprising the organic molecule.

In one or more embodiments, the asymmetric semiconductors comprise but not limited to the structures of A'-D'-D-D"-A" (or A1-D1-D-D2-A2), A-D-A', A-D'-D-D"-A, A'-D'-D-D"-A', A-D'-D-D'-A', A-D'-D-D"-A', A-D'-D-A'-A, A-A'-D-D'-A, A-D'-D-A'-A", A-A'-D-A"-A, A-A'-D-A'-A", A'-D-A-D'-A', A'-D'-A-D'-A", A'-D'-A-D"-A", D'-A-D", D'-A-D-A-D", D'-A-D-A'-D", D'-D'-A-D"-D', D'-D'-A-A'-A', D'-A'-A-A'-D". While D is any electron donor unit; D', D", D1 and D2 is any electron donor unit or bridge unit or nothing; A is any electron acceptor unit, A', A", A1 and A2 is any electron acceptor unit or bridge unit or nothing. Either D' and D" (D1 and D2) or A' and A" are different to make the semiconductor molecules asymmetric.

In one or more embodiments, D can be but not limited to the following strong electron donors:

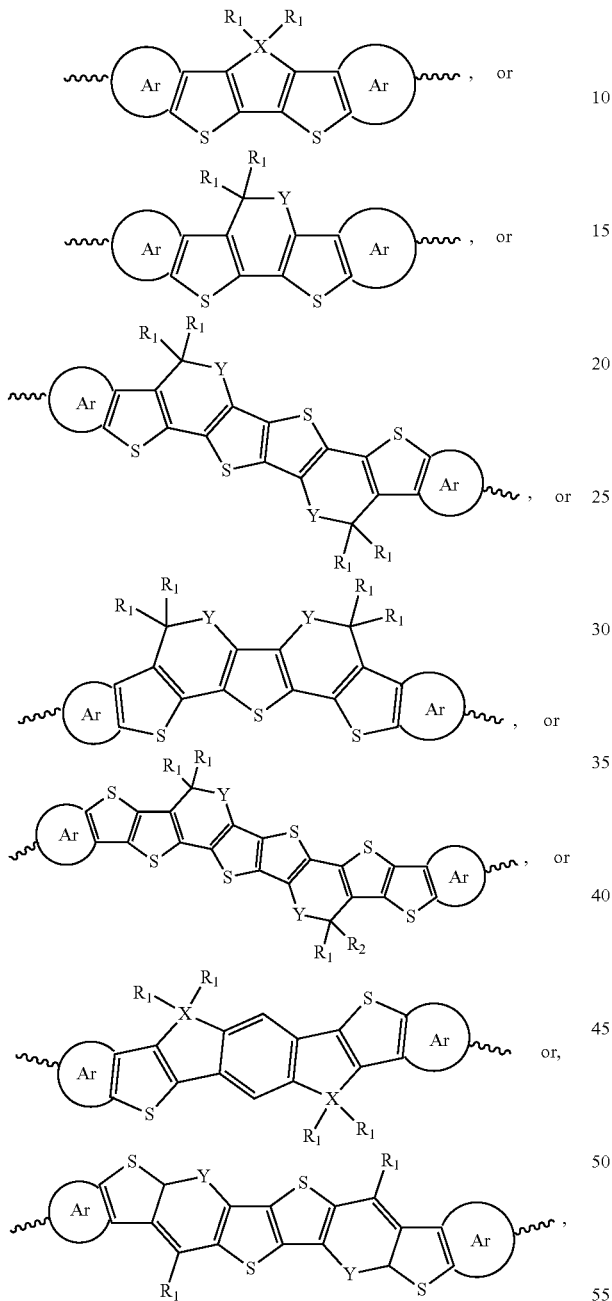

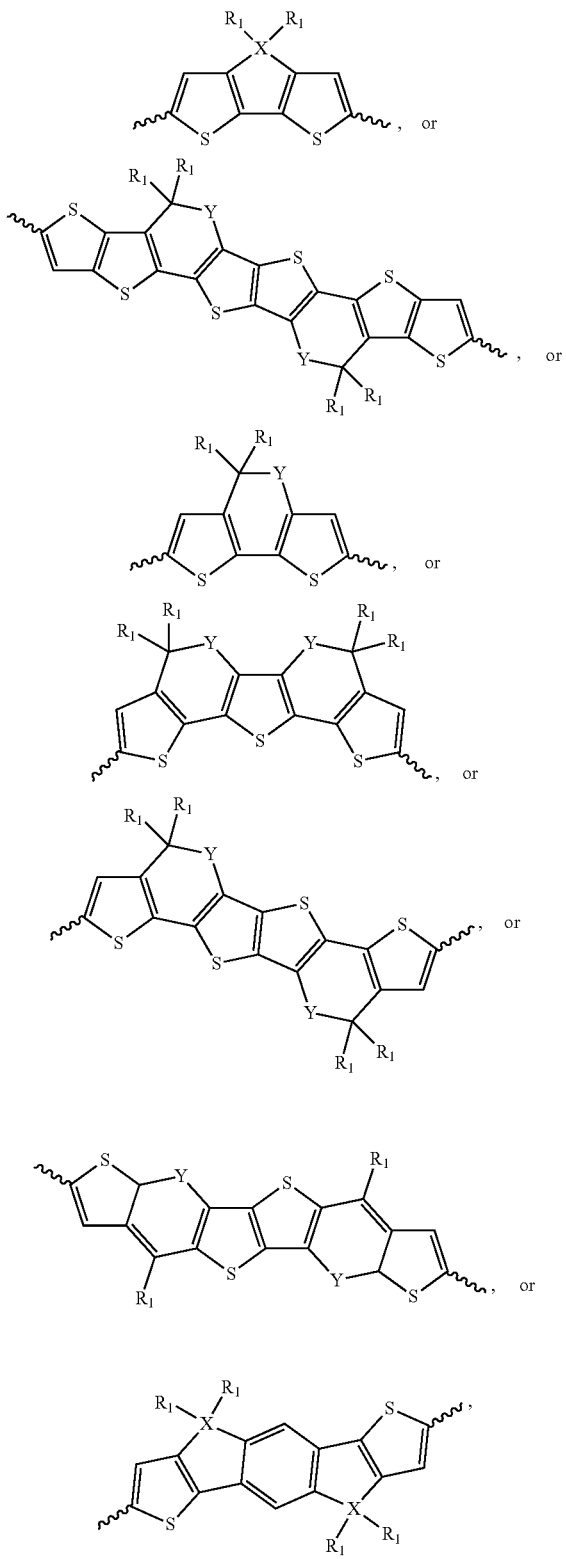

where each $R_1$, $R_3$ is independently hydrogen or a substituted or non-substituted alkyl, aryl or alkoxy chain; X is C, Si, Ge, N or P; Y is O, S, Se or N—$R_3$; each Ar is independently a substituted or non-substituted aromatic functional group, or each Ar is independently nothing and the valence of its respective thiophene ring is completed with hydrogen, each Ar may comprise one, two, three or more 5-membered or 6-membered aromatic rings.

In one or more embodiments, D can be but not limited to the following strong electron donors:

where each $R_1$, $R_3$ is independently hydrogen or a substituted or non-substituted alkyl, aryl or alkoxy chain; X is C, Si, Ge, N or P; Y is O, S, Se or N—$R_3$.

In one or more embodiments, D can be but not limited to the following strong electron donors:

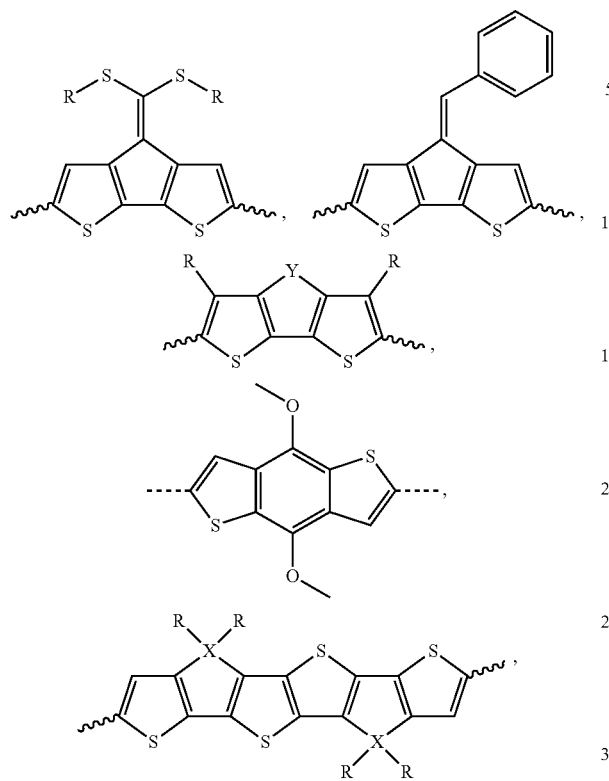

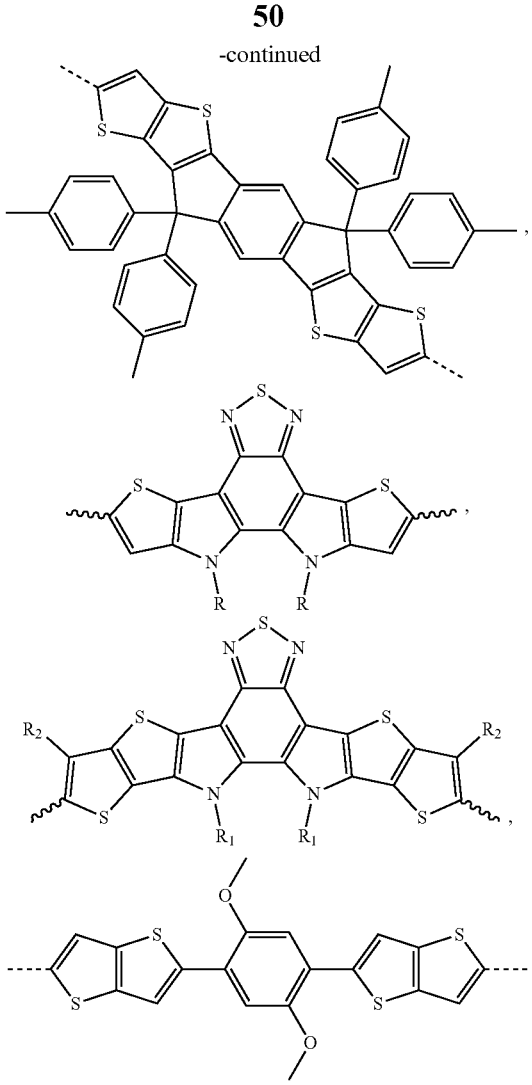

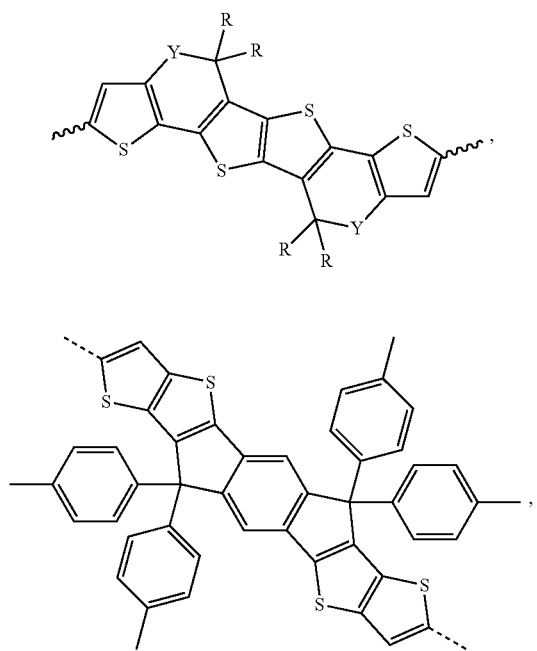

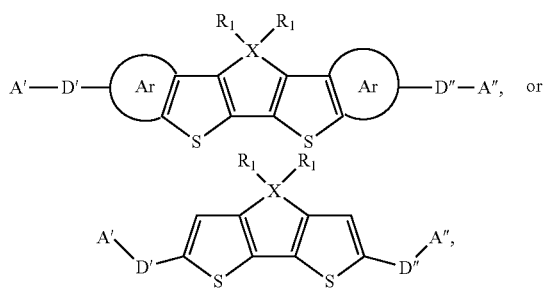

Where each R, $R_1$, $R_2$, $R_3$ is independently hydrogen or a substituted or non-substituted alkyl, aryl or alkoxy chain; X is C, Si, Ge, N or P; Y is O, S, Se or N—$R_3$.

In one or more embodiments, the A'-D'-D-D"-A" semiconductor comprises the general structure:

where each $R_1$ is independently hydrogen or a substituted or non-substituted alkyl, aryl or alkoxy chain; X is C, Si, Ge, N or P; each Ar is independently a substituted or non-substituted aromatic functional group, or each Ar is independently nothing and the valence of its respective thiophene ring is completed with hydrogen, each Ar may comprise one, two, three or more 5-membered or 6-membered aromatic rings; D' and D" can be any bridging electron donor units, groups or moieties; A' and A" can be any end electron acceptor units, groups or moieties. A' and A" can be the same or different. A and A" can be but not limited to those listed in FIGS. 19A-H. Either D' and D" or A' and A" are different to make the molecule asymmetric.

In one or more embodiments, the A'-D'-D-D"-A" semiconductor comprises the general structure:

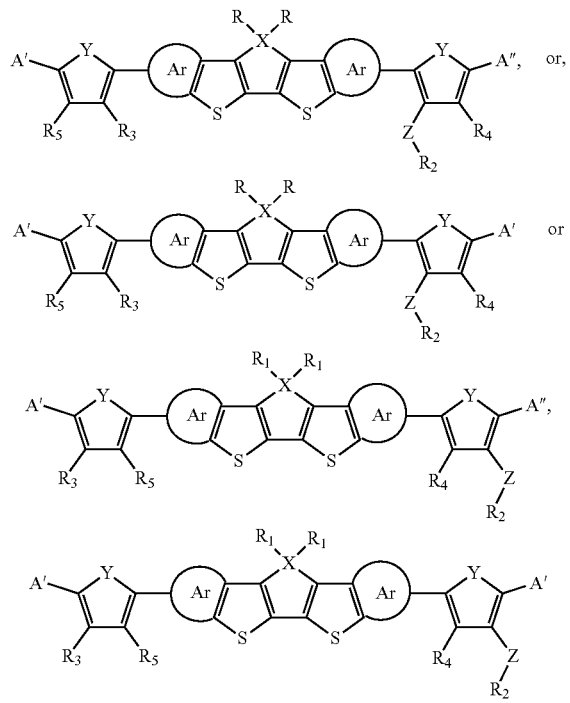

where each R, $R_1$, $R_2$, $R_3$, $R_4$, $R_5$, $R_6$ is independently hydrogen or a substituted or non-substituted alkyl, aryl or alkoxy chain but $R_3$ is different from $Z-R_2$, in some embodiments, $R_4$ is either a hydrogen or the same as $Z-R_2$; In some embodiments, $R_5$ is either a hydrogen or the same as $R_3$; X is C, Si, Ge, N or P; Y is O, S, Se, or $N-R_6$, Z is O, S, Se, or $N-R_6$; each Ar is independently a substituted or non-substituted aromatic functional group, or each Ar is independently nothing and the valence of its respective thiophene ring is completed with hydrogen, each Ar may comprise one, two, three or more 5-membered or 6-membered aromatic rings; A' and A" can be any end electron acceptor units, groups or moieties (e.g., acceptor moiety). A' and A" can be the same or different. A' and A" can be but not limited to those listed in FIG. 19A-H.

In one or more embodiments, A' and A" can be an electron acceptor group, moiety or unit of the following structure:

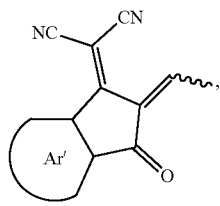

where

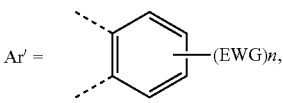

EWG=any electron withdrawing group, can be but not limited to F, Cl. Br, I, CN, $CF_3$, $NO_2$, sulfonate, ketone, ester, n=1, 2, 3 or 4. Examples of Ar' can be but not limited to the following:

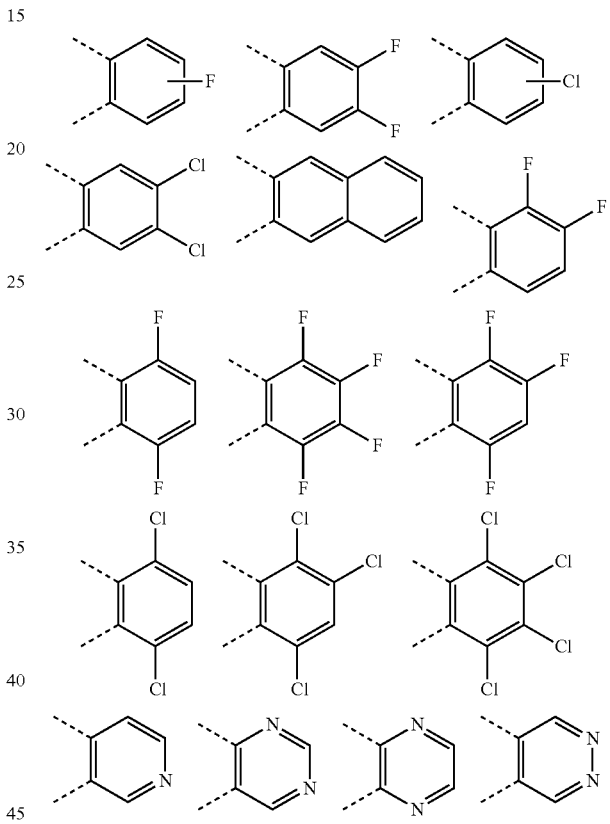

In one or more embodiments, bridge unit, group or moiety (also called π-bridges) D', D", D1 and D2 can be but not limited to the following electron donors:

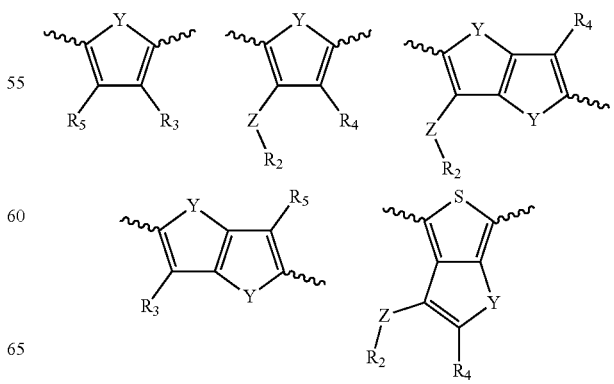

-continued

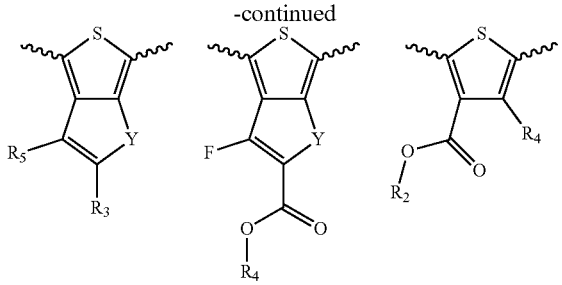

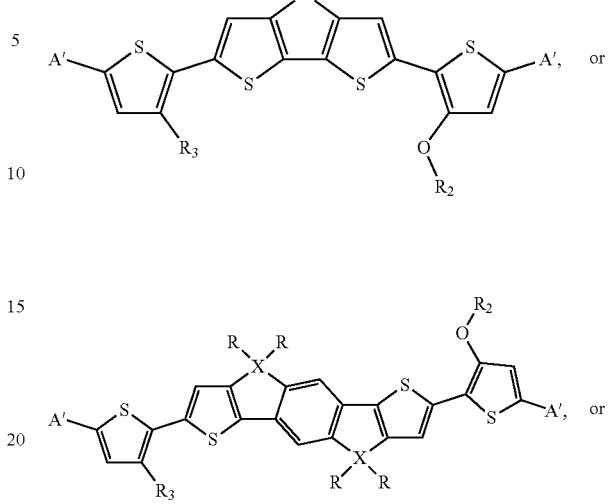

where each $R_2$, $R_3$, $R_4$, $R_5$, $R_6$ is independently hydrogen or a substituted or non-substituted alkyl, aryl or alkoxy chain; in some embodiments, $R_4$ is either a hydrogen or the same as $Z-R_2$; $R_5$ is either a hydrogen or the same as $R_3$; Y is O, S, Se, or N—$R_6$, D' and D" or D1 and D2 are different.

In one or more embodiments, the A'-D'-D-D"-A" semiconductor comprises the general structure:

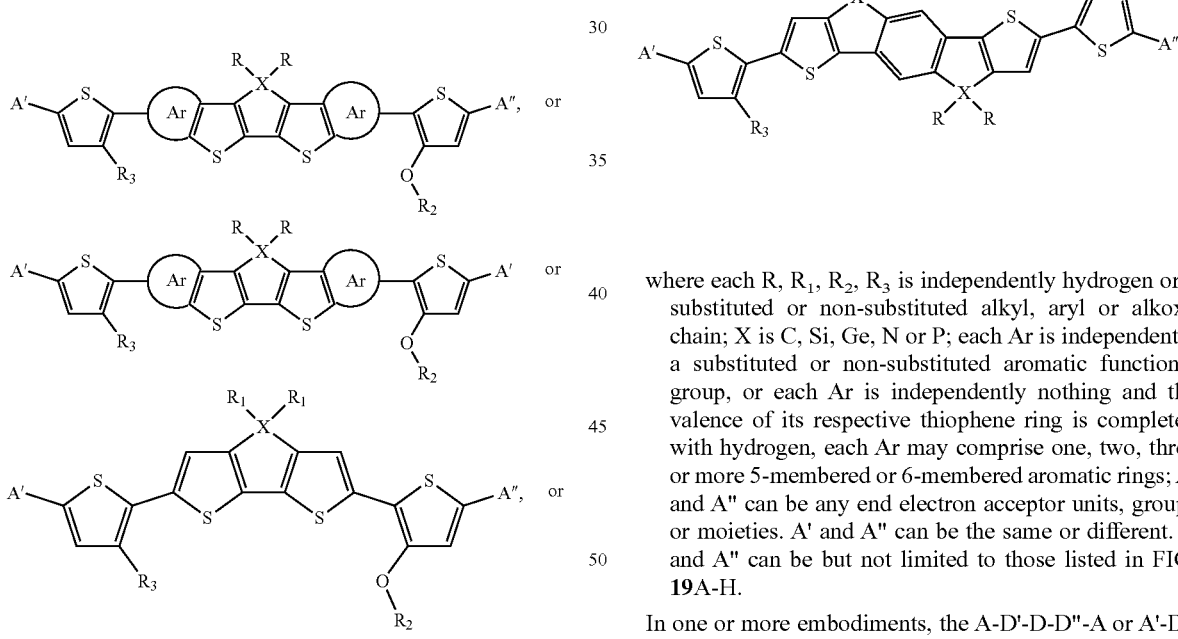

where each R, $R_1$, $R_2$, $R_3$ is independently hydrogen or a substituted or non-substituted alkyl, aryl or alkoxy chain; X is C, Si, Ge, N or P; each Ar is independently a substituted or non-substituted aromatic functional group, or each Ar is independently nothing and the valence of its respective thiophene ring is completed with hydrogen, each Ar may comprise one, two, three or more 5-membered or 6-membered aromatic rings; A' and A" can be any end electron acceptor units, groups or moieties. A' and A" can be the same or different. A and A" can be but not limited to those listed in FIG. 19A-H.

In one or more embodiments, the A-D'-D-D"-A or A'-D'-D-D"-A' semiconductor comprises the general structure:

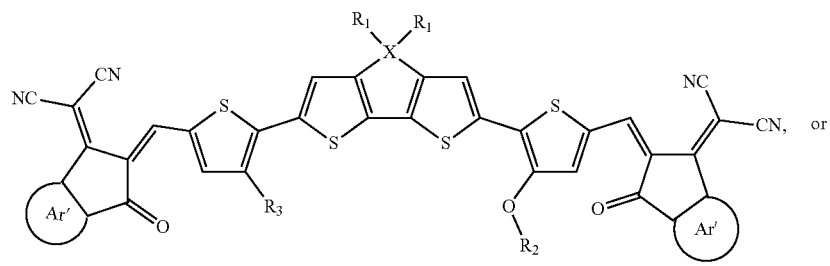

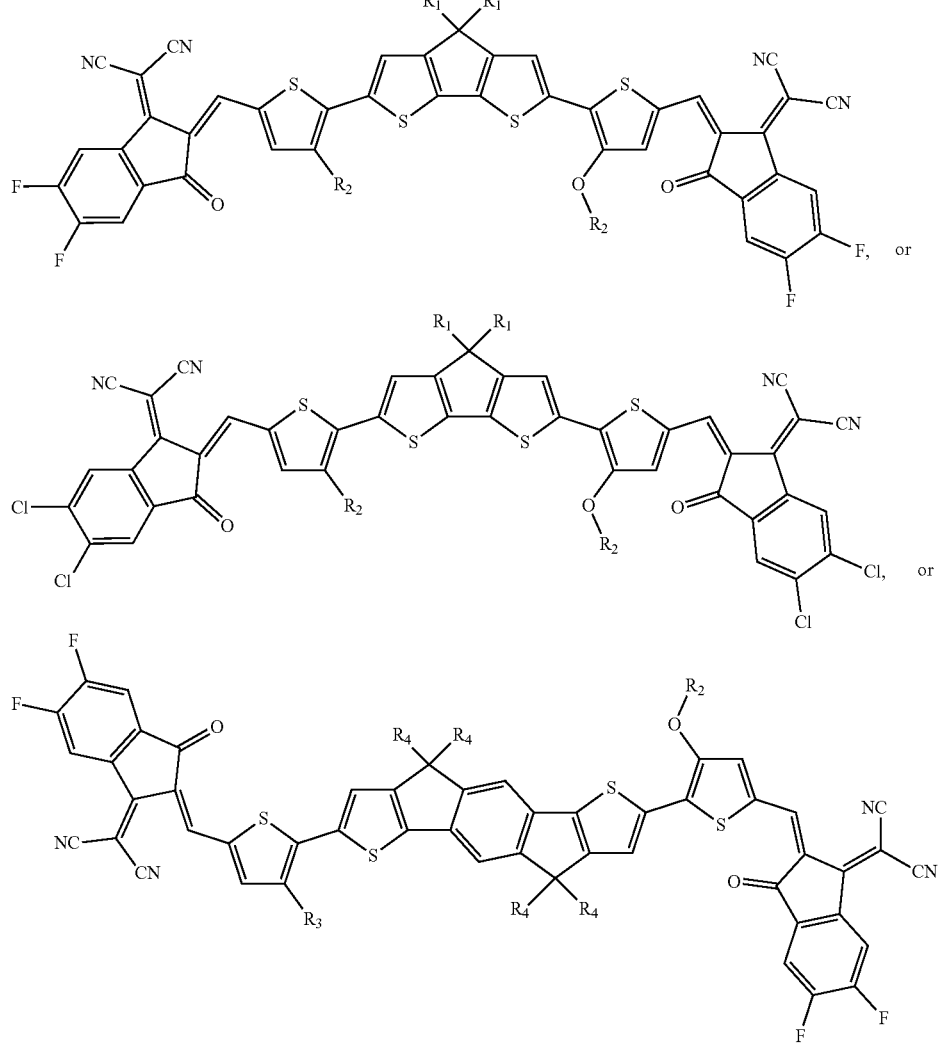

where each $R_1$, $R_2$, $R_3$, $R_4$ is independently hydrogen or a substituted or non-substituted alkyl, aryl or alkoxy chain; In some embodiments, $R_1$, $R_2$, $R_3$ are 2-ethylhexyl; In some embodiments, $R_4$ is n-octyl or 4-hexylphenyl; X is C, Si, Ge, N or P; In some embodiments,

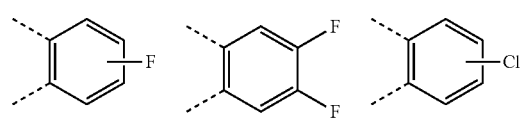

EWG=any electron withdrawing group, can be but not limited to F, Cl. Br, I, CN, $CF_3$, $NO_2$, sulfonate, ketone, ester, n=1, 2, 3 or 4. Examples of Ar' can be but not limited to the following:

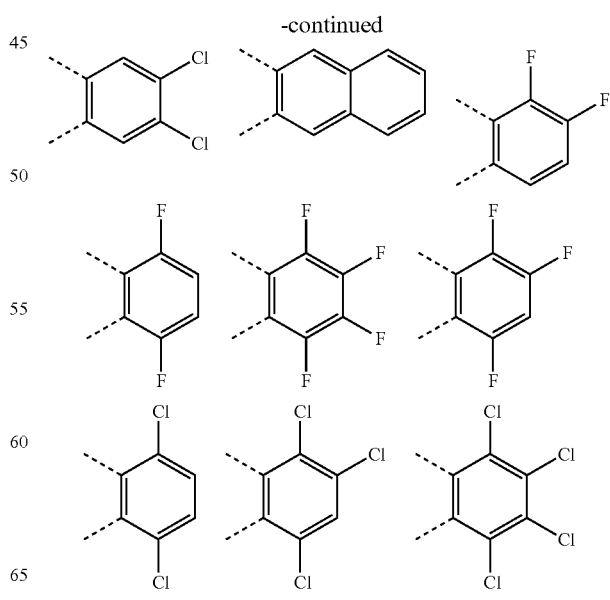

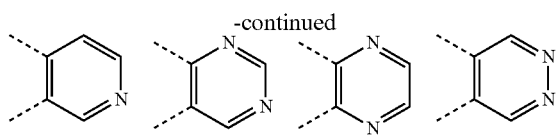

In one or more embodiments, the A-A'-D-D'-A semiconductor comprises the general structure:

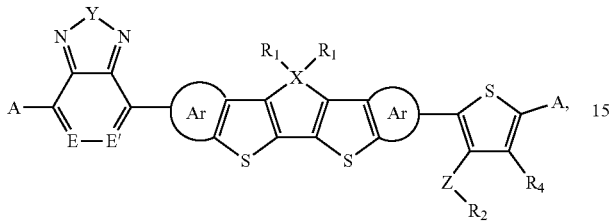

where each R, $R_1$, $R_2$, $R_3$, $R_4$, $R_5$ is independently hydrogen or a substituted or non-substituted alkyl, aryl or alkoxy chain; in some embodiments, $R_4$ is either a hydrogen or the same as Z—$R_2$; X is C, Si, Ge, N or P; Y and Z are independently O, S, Se, or N—$R_3$; E and E' are independently CH, CF, N, C—CN, or C—$OR_5$; each Ar is independently a substituted or non-substituted aromatic functional group, or each Ar is independently nothing and the valence of its respective thiophene ring is completed with hydrogen, each Ar may comprise one, two, three or more 5-membered or 6-membered aromatic rings; A can be any end electron acceptor units, groups or moieties. A can be but not limited to those listed in FIG. 19A-H. In one or more embodiments, A can be an electron acceptor structure of the following structure:

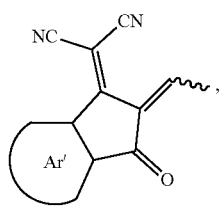

where

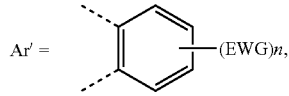

EWG=any electron withdrawing group, can be but not limited to F, Cl. Br, I, CN, $CF_3$, $NO_2$, sulfonate, ketone, ester, n=1, 2, 3 or 4. Examples of Ar' can be but not limited to the following:

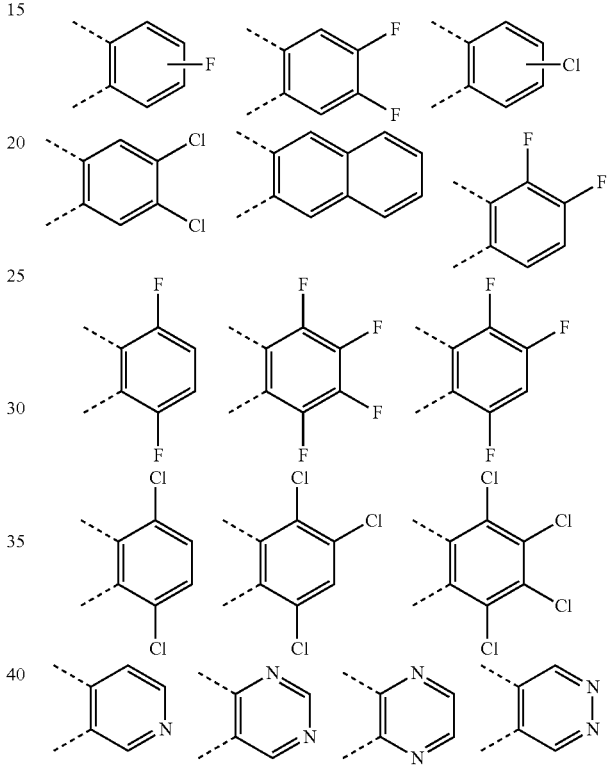

In one or more embodiments, the A-A'-D-D'-A semiconductor comprises the structure:

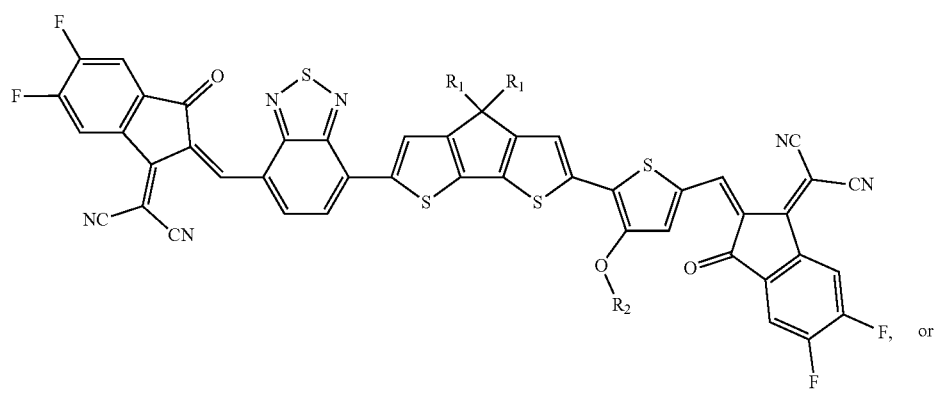

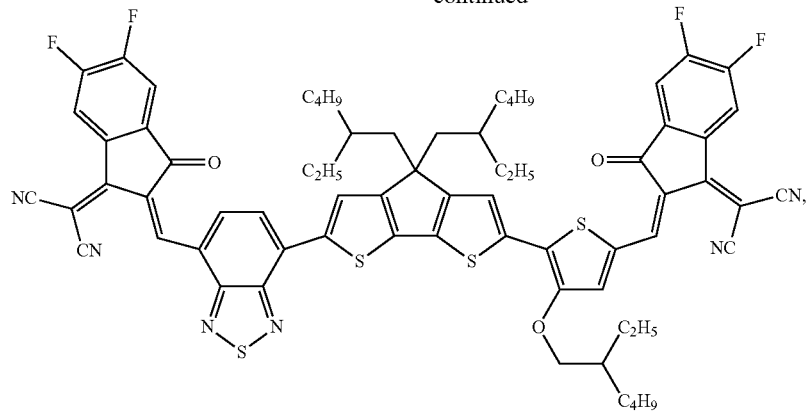

where each $R_1$ and $R_2$ is independently hydrogen or a substituted or non-substituted alkyl, aryl or alkoxy chain.

In one or more embodiments, the A-D'-D-D"-A semiconductor comprises the general structure:

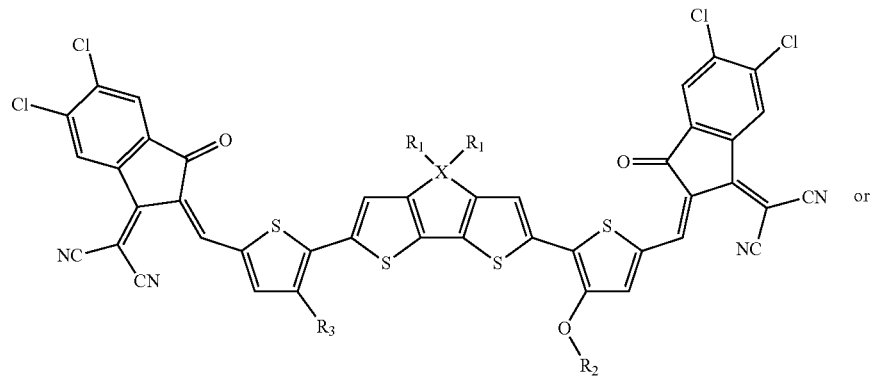

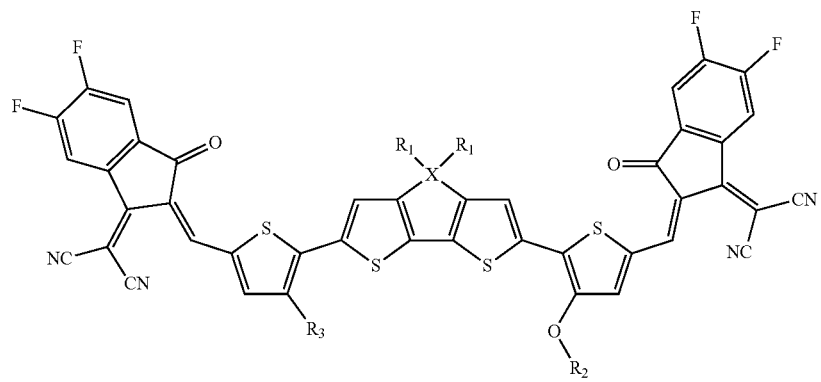

and isomers thereof, where X is C, Si, Ge, N or P; Each $R_1$, $R_2$ and $R_3$ is independently hydrogen or a substituted or non-substituted alkyl, aryl or alkoxy chain, and $R_3$ is different with $OR_2$. In some embodiments, $R_1$, $R_2$ and $R_3$ can be 2-ethylhexyl.

In one or more embodiments, the A-D'-D-D"-A semiconductor comprises the general structure:

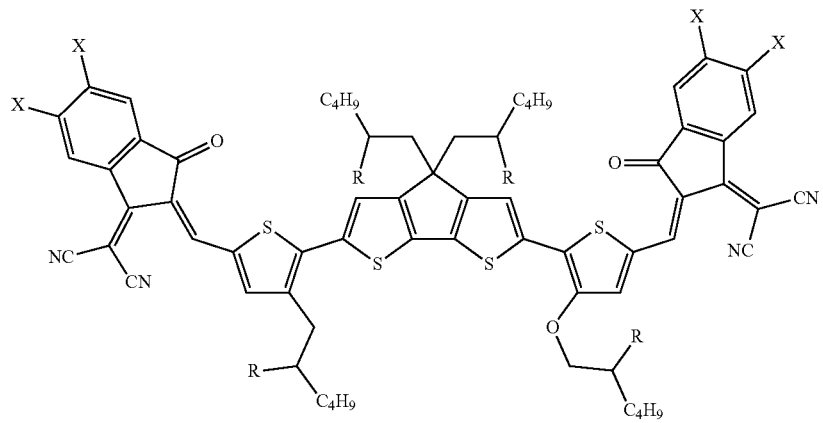

and isomers thereof, where X is F, or Cl; each R is independently hydrogen or a substituted or non-substituted alkyl, aryl or alkoxy chain.

In one or more embodiments, the A-D'-D-D"-A semiconductor comprises the general structure:

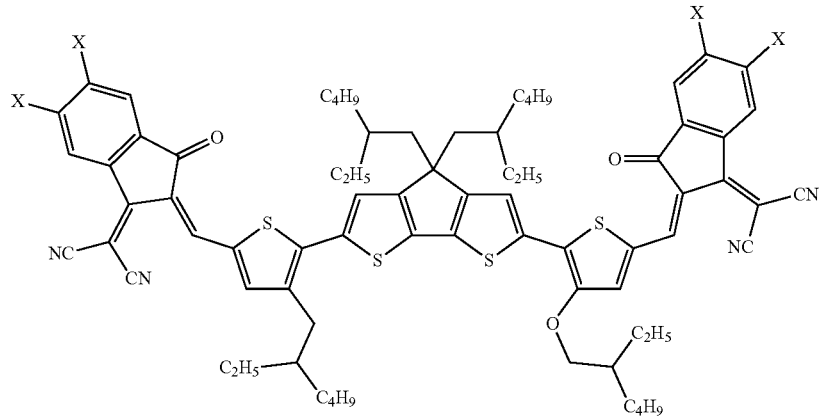

and isomers thereof, where X is F, or Cl.

In one or more examples, the A-D'-D-D"-A semiconductor comprises the general structure (and isomers thereof):

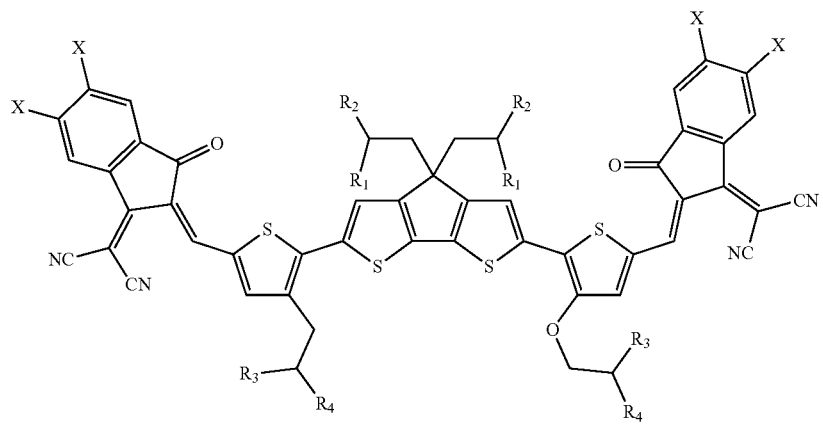

where X is F or Cl; $R_1$, $R_2$, $R_3$, $R_4$ are independently hydrogen or a substituted or non-substituted alkyl, aryl or alkoxy chain. In one or more embodiments, $R_1$, and $R_3$ are ethyl, $R_2$ and $R_a$ are n-butyl.

In some embodiments, the R, $R_1$, $R_2$, $R_3$, $R_4$, $R_5$ and $R_6$ groups can be the same. The R, $R_1$, $R_2$, $R_3$, $R_4$, $R_5$ and $R_6$ comprising the substituted or non-substituted alkyl, aryl or alkoxy chain can be a $C_6$-$C_{50}$ substituted or non-substituted alkyl or alkoxy chain, —$(CH_2CH_2O)_n$ (n=2~30), $C_6H_5$, —$C_nF_{(2n+1)}$ (n=2~50), —$(CH_2)_nN(CH_3)_3Br$ (n=2~50), 2-ethylhexyl, $PhC_mH_{2m+1}$ (m=1-50), —$(CH_2)_nN(C_2H_5)_2$ (n=2~50), —$(CH_2)_nSi(C_mH_{2m+1})_3$ (m, n=1 to 50), or —$(CH_2)_nSi(OSi(C_mH_{2m+1})_3)_x(C_pH_{2p+1})_y$ (m, n, p=1 to 50, x+y=3). The R, $R_1$, $R_2$, $R_3$, $R_4$, $R_5$ and $R_6$ groups can be a branched side-chain comprising a $C_3$-$C_{50}$, $C_5$-$C_{50}$, $C_8$-$C_{50}$, or $C_9$-$C_{50}$ substituted or non-substituted alkyl chain. Examples of branched alkyl chains include isopropyl, sec-butyl, t-butyl, 1,2-dimethylpropyl, 1,1-dimethyl-propyl, 4-methylpentyl, 1-methylpentyl, 2-methylpentyl, 3-methylpentyl, 1,1-dimethylbutyl, 2,2-dimethylbutyl, 3,3-dimethylbutyl, 1, 2-dimethylbutyl, 1,3-dimethylbutyl, 1,2,2-trimethylpropyl, 1,1,2-trimethylpropyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, 6-methylheptyl, 1-methylheptyl, 1,1,3,3-tetramethylbutyl, 1-, 2-, 3-, 4-, 5-, 6- or 7-methyloctyl, 1-, 2-, 3-, 4- or 5-ethylheptyl, 1-, 2- or 3-propylhexyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, dimethyldecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propyloctyl, 1-, 2- or 3-butylheptyl, 1-pentylhexyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-, 2-pentylheptyl, branched butyl, pentyl, hexyl, heptyl, octyl, nonyl, decyl, undecyl, dodecyl, tridecyl, tetradecyl, pentadecyl, hexadecyl, heptadecyl, octadecyl, nonoadecyl, eicosyl with one or more branch points at any carbon of the alkyl chain, such as 2 (or 1, or 3, or 4)-ethylhexyl, 2 (or 1, or 3, or 4)-hexyldecyl, 2 (or 1, or 3, or 4)-octyldodecyl, 2 (or 1 or 3, or 4)-butyloctyl, 4 (or 1, or 2, or 3, or 5, or 6)-butyldecyl, 5 (or 1, or 2, or 3, or 4, or 6, or 7)-butylundecyl, 6 (or 1, or 2, or 3, or 4, or 5, or 7, or 8)-butyldodecyl, 12 (or 1, or 2, or 3, or 4, or 5, or 6, or 7, or 8, or 9, or 10, or 11, or 13, or 14)-butyloctadecyl, and the like.

Examples of dithiophene units include those illustrated in Table B (FIG. 30B) in U.S. Utility patent application Ser. No. 14/426,467, filed on Mar. 6, 2015, by Hsing-Rong Tseng, Lei Ying, Ben B. Y. Hsu, Christopher J. Takacs, and Guillermo C. Bazan, entitled "FIELD-EFFECT TRANSISTORS BASED ON MACROSCOPICALLY ORIENTED POLYMERS,". Further examples of dithiophene units are illustrated in Table 3 of U.S. Utility patent application Ser. No. 15/406,382, filed on Jan. 1, 2017, by Hsing-Rong Tseng, Lei Ying, Ben B. Y. Hsu, Christopher J. Takacs, and Guillermo C. Bazan, entitled "FIELD-EFFECT TRANSISTORS BASED ON MACROSCOPICALLY ORIENTED POLYMERS,"

A, A', A", A1 and A2 is an acceptor moiety, examples are listed in FIGS. 19A-19H.

Block 1806 represents optionally combining the organic semiconducting molecule, comprising an acceptor molecule, with a donor molecule in a solution. Examples of donor molecules include PTB7-Th, DPP polymers, PIPCP, PBPCP, or donor molecules illustrated in FIGS. 20A-20F (wherein the $C_2H_9$, $C_2H_5$, $C_4H_9$, $C_{12}H_{25}$, and other side chains in other examples can be replaced with any side chain comprising the substituted or non-substituted alkyl, aryl or alkoxy chain can be a $C_6$-$C_{50}$ substituted or non-substituted alkyl or alkoxy chain). The donor molecule can be a small molecule, an oligomer or a polymer.

FIG. 21 illustrates a synthesis pathway for one or more intermediates used in the processes described herein.

Block 1808 represents optionally solution processing the solution so as to form an active region in an organic device such as, but not limited to, a solar cell or a photodetector, e.g., so that the active region comprises the organic semiconducting molecule.

Block 1810 represents the end result, a composition of matter or a device comprising the composition of matter.

In one or more examples, wherein each of the organic semiconducting molecules are each an electron acceptor. In one or more examples, the active region comprises each of the electron acceptors forming a heterojunction with an electron donor comprising a second organic semiconducting molecule. In one or more examples, the active region has a thickness of at least 300 nanometers or in a range of 200 nm to 1 micrometer.

In one or more examples, the device is an organic solar cell outputting current in response to sunlight absorbed in the active region.

In one or more embodiments, the active region is the sensing element in an infrared photodetector, e.g., outputting current in response to infrared electromagnetic radiation absorbed in the active region.

In one or more examples, the active region comprises an organic semiconducting acceptor moiety coupled to a donor moiety so as to form an organic semiconducting molecule having an A-D'-D-D"-A structure as described herein, wherein the active region outputs electrical current in response to absorbing electromagnetic radiation.

In one or more examples, the device or composition of matter comprises a plurality of the electron donors and a plurality of the organic semiconducting molecules that are phase separated, wherein the organic semiconducting molecules are disposed in a hierarchical network and the electron donors comprising the second organic semiconducting molecules occupy spaces in the hierarchical network. In one example, the hierarchical network comprises larger mid rib shaped regions connected by smaller or thinner regions. In one example, the composition of matter is solution processed with an additive that promotes formation of the hierarchical network.

In one or more embodiments, the organic semiconducting molecule has a HOMO in a range of −5.0 eV to −5.5 eV, a LUMO in a range of −3.8 eV to −4.3 eV, and a bandgap in a range of 1.0 eV to 1.4 eV.

In one or more embodiments, the organic semiconducting molecule has a bandgap narrower than 1.3 eV.

In one or more examples, the organic semiconducting molecule has a bandgap narrower than 1.2 eV or narrower than 1.1 eV.

In one or more embodiments, the organic semiconducting molecule has a main absorption band between 850 and 1000 nm.

In one or more embodiments, the organic semiconducting molecule has a maximum extinction coefficient in solution of at least $1 \times 10^5 M^{-1} cm^{-1}$.

In one or more embodiments, the organic semiconducting molecule is an electron acceptor.

In one or more embodiments, the device further comprises an organic semiconducting donor molecule (e.g., PTB7-Th).

In one or more embodiments, the device:
has an energetic offset between the donor and acceptor HOMO levels ($HOMO_D$-$HOMO_A$, $\Delta E_{HOMO}$) of no more than 0.2 eV;

has an energetic offset between the donor and acceptor HOMO levels (HOMO$_D$-HOMO$_A$, $\Delta E_{HOMO}$) of no more than 0.1 eV;

has an external quantum efficiency (EQE) over 50%, over 55%, or over 60% in the wavelength range of 600-950 nm;

has an external quantum efficiency (EQE) over 45%, over 55%, or over 60%, in the wavelength range of 850-1000 nm; a short circuit current $J_{SC}$ over 24 mA cm$^{-2}$;

has a responsivity of 0.5 AW$^{-1}$ at 920 nm wavelength, −0.1V applied bias.

has a responsivity of 0.45 AW$^{-1}$ at 940 nm wavelength, −0.1 V applied bias.

has a responsivity of 0.53 AW$^{-1}$ at 920 nm wavelength, −2V applied bias.

has a responsivity of 0.5 AW$^{-1}$ at 960 nm wavelength, −2V applied bias.

has a responsivity over 0.45 AW$^{-1}$ in the wavelength range of 750-950 nm wavelength, −0.1V applied bias.

has a shot noise-limited specific detectivity over $1\times10^{13}$ Jones in the wavelength range of 750-1000 nm wavelength, −0.1 V applied bias.

has a shot noise-limited specific detectivity over $1\times10^{13}$ Jones in the wavelength range of 400-1000 nm wavelength, −0.1 V applied bias.

has a shot noise-limited specific detectivity of $3.31\times10^{13}$ Jones at 940 nm wavelength, −0.1 V applied bias.

has a shot noise-limited specific detectivity over $1\times10^{13}$ Jones in the wavelength range of 860-980 nm wavelength, −2 V applied bias (an electric field strength of 67 kV cm$^{-1}$).

has a shot noise-limited specific detectivity over $3\times10^{12}$ Jones in the wavelength range of 400-1000 nm wavelength, −2 V applied bias.

has a dark current as low as $1\times10^{-10}$ A/cm$^2$ at 0V applied bias.

has a dark current as low as $7\times10^{-9}$ A/cm$^2$ at −2V applied bias.

has a dark current as low as $8\times10^{-8}$ A/cm$^2$ at −3V applied bias.

has a photo current at least $1\times10^{-5}$ A/cm$^2$ at reversed applied bias, under the illumination of 940 nm monochromatic infrared light of ~54 µW cm$^{-2}$.

has a noise equivalent power (NEP) of $1.2\times10^{-13}$ W Hz$^{-1/2}$ at −0.1 V applied bias, of $2.0\times10^{-13}$ W Hz$^{-1/2}$ at −2 V applied bias, At a frequency of 100 Hz.

has a linear dynamic range (LDR) of 126-148 dB under irradiation of 940 nm infrared light.

has a cutoff frequency of 240 kHz at a reverse bias of −2 V under 940 nm infrared light.

In one or more embodiments, the active region (e.g., in the solar cell or the photodetector) is sensitive to infrared wavelengths (i.e., the bandgap of the acceptor molecule and/or donor molecule are sufficiently low to absorb infrared radiation).

The photovoltaic device may have a standard or inverted structure. It may comprise a substrate, a first electrode deposited on the substrate, a second electrode, an electron conducting/hole blocking layer deposited either between the first electrode and the active layer, or between the active layer and the second electrode, and an optional hole conducting/electron blocking layer deposited either in between the first electrode and the active layer, or between the active layer and the second electrode.

In one or more examples, the device 600, as illustrated in FIG. 6c, comprises a cathode 602; an anode 604; and the active region 606 having a thickness 608 between the cathode and the anode; and wherein:

holes and electrons are generated in the active region in response to electromagnetic radiation incident on the active region,
the electrons are collected in the electron acceptor and are transmitted through to the cathode, and
the holes are collected in the electron donor and transmitted through to the anode.

Also illustrated is a hole blocking layer 610 between the cathode and the active region, and an electron blocking layer 612 between the anode and the active region.

During operation, either or both the electron donor and the electron acceptor absorb photons to create electron-hole pairs, the electron acceptor (interfacing with the electron donor) receives or collects the electron in the electron hole pair and transports the electron to the cathode interface layer/hole blocking layer and the cathode. The hole is transported by the electron donor to the anode interface layer/electron blocking layer and then the anode.

Examples of a substrate include, but are not limited to, a flexible substrate, a plastic substrate, a polymer substrate, a metal substrate, a silicon substrate, or a glass substrate. In one or more embodiments, the flexible substrate is at least one film or foil selected from a polyimide film, a polyether ether ketone (PEEK) film, a polyethylene terephthalate (PET) film, a polyethylene naphthalate (PEN) film, a polytetrafluoroethylene (PTFE) film, a polyester film, a metal foil, a flexible glass film, and a hybrid glass film. Examples of cathode interface layer include, but are not limited to ZnO and/or ITO. The ZnO can include multiple layers (e.g., two layers) and have a surface roughness of less than 5 nm over an area of 0.2 cm$^2$.

Examples of anode interface layer include, but are not limited to MoOx having a thickness in a range of 5-150 nm. Further examples include, but are not limited to, the hole transporting/conducting layer material selected from, but not limited to, the group comprising or consisting of poly(3,4-ethylenedioxythiophene): polystyrene sulfonate (PEDOT:PSS), p-type organic small molecule semiconductors such as Spiro-MeOTAD, pentacene, biscarbazolylbenzene, oligomer semiconductors, polymer semiconductors such as PTAA, poly(3-hexylthiophene-2,5-diyl) (P3HT), donor-acceptor copolymer semiconductors such as PCPDTBT, PCDTBT, metal oxides such as CuI, CuBr, CuSCN, Cu$_2$O, CuO or CIS. VO$_x$, NbO$_x$, MoO$_x$, WO$_x$, NiO$_x$, where x is 3 or less than 3, or other main group or transition metal oxides and a compound as shown in FIG. 1 of U.S. Ser. No. 14/954,131.

Examples of cathode material include, but are not limited to, ITO. In further examples, the electron transporting/conducting layer material is selected from, but not limited to, the group comprising or consisting of TiO$_2$, ZnO, SnO, SnO$_2$, SiO$_2$, CeO$_2$, ZrO$_2$, CdSe, WO$_3$, ZnSnO$_4$, PbI$_2$, SrTiO$_3$, fullerene based electron acceptors (C$_{60}$, C$_{70}$, PC$_{61}$BM, PC$_{71}$BM, ICBA), borane based electron acceptors (3TPYMB), Bathocuproine (BCP), bathophenanthroline (Bphen), ITIC type of non-fullerene acceptors, NDI and PDI based non-fullerene acceptors, and the combination of above (double layer). The electron transporting layer may have a thickness of 2 nm to 500 nm, preferably a thickness of 20 nm to 200 nm, more preferably a thickness of 50 nm to 100 nm.

Examples of cathode and anode materials include, but are not limited to, a metal or at least one material selected from gold, aluminum, copper, silver, silver paste, palladium, platinum, nickel, a combination/bilayer of metal and molybdenum oxide or molybdenum (wherein the MoOx is an interlayer), a liquid metal (e.g., mercury alloy, eutectic gallium indium), a transparent conductive layer, carbon nanotubes, graphene, carbon paste, PEDOT:PSS, and a conjugated polyelectrolyte.

The active layer, electron transporting/hole blocking layers, hole transporting/electron blocking layers of the electronic device may be deposited by solution casting or vapor deposition. Illustrative thin film deposition methods include a spin coating method, a casting method, a microgravure coating method, a gravure coating method, a bar coating method, a roll coating method, a blade coating method, a wire bar coating method, a dip coating method, a spray coating method, a free span coating method, a dye coating method, a screen printing method, a flexo printing method, an offset printing method, an inkjet printing method, a dispenser printing method, a nozzle coating method and a capillary coating method, for forming a film from a solution.

In one or more examples, the active layer has a thickness in a range of 50-600 nm. In some embodiments, the active layer has a thickness in a range of 87-300 nm. In some embodiments, the active layer has a thickness of at least 300 nanometers or in a range of 200 nm to 1 micrometer.

Advantages and Improvements

The above results demonstrate successful synthesis of an asymmetrical ultra-NBG non-fullerene acceptor CO1-4F and incorporation as an electron acceptor in OSCs and OPDs. The NIR photodiodes based on PTB7-Th:CO1-4F blend achieved a PCE of 10.24% with a high $J_{SC}$ as high as −25 mA/cm$^2$ for OSCs and a high responsivity of 0.52 A W$^{-1}$ in the NIR (920 nm) for OPDs, respectively. The EQE spectrum indicates a combination of strong light harvesting across the broad solar spectrum, efficient hole/electron transfer between PTB7-Th and CO1-4F, and efficient charge transport enabled by the interconnected NFA-rich domains with a hierarchical network. Our results demonstrate that designing the asymmetrical A-D'-D-D"-A configuration by introducing two different π-bridges can be a straightforward strategy to delicately modulate the energy band structure and to improve the optoelectronic responses of OSC and OPD devices.

Current photodetector technology is predominantly based on inorganic semiconductors, which are expensive and are difficult to bandgap tune. The present disclosure reports on a new class of asymmetric non-fullerene acceptor materials, which led to highly efficient near-infrared organic photodetectors that can compete directly with silicon photodiodes. Cheap, solution-processable, light-weight, flexible, and large-area devices can operate at much lower voltages than their inorganic counterparts. Using organic semiconductors also provides opportunities to access a broad and tunable absorption spectrum.

REFERENCES

The following references are incorporated by reference herein.

References for First Example

[1] M. A. Green, *Nat. Energy* 2016, 1, 15015.
[2] A. C. Arias, J. D. MacKenzie, I. McCulloch, J. Rivnay, A. Salleo, *Chem. Rev.* 2010, 110, 3.
[3] H. Dong, H. Zhu, Q. Meng, X. Gong, W. Hu, *Chem. Soc. Rev.* 2012, 41, 1754.
[4] L. Ying, F. Huang, G. C. Bazan, *Nat. Commun.* 2017, 8, 14047.
[5] Y.-J. Cheng, S.-H. Yang, C.-S. Hsu, *Chem. Rev.* 2009, 109, 5868.
[6] L. Dou, Y. Liu, Z. Hong, G. Li, Y. Yang, *Chem. Rev.* 2015, 115, 12633.
[7] Q. Cui, G. C. Bazan, *Acc. Chem. Res.* 2018, 51, 202.
[8] C. J. Traverse, R. Pandey, M. C. Barr, R. R. Lunt, *Nat. Energy* 2017, 2, 849.
[9] Q. Tai, F. Yan, *Adv. Mater.* 2017, 29, 1700192.
[10] C. J. M. Emmott, J. A. Röhr, M. Campoy-Quiles, T. Kirchartz, A. Urbina, N. J. Ekins-Daukes, J. Nelson, *Energy Environ. Sci.* 2015, 8, 1317.
[11] F. P. Garcia de Arquer, A. Armin, P. Meredith, E. H. Sargent, *Nat. Rev. Mater.* 2017, 2, 16100.
[12] Z. Wu, Y. Zhai, H. Kim, J. D. Azoulay, T. N. Ng, *Acc. Chem. Res.* 2018, 51, 3144.
[13] X. Liu, Y. Lin, Y. Liao, J. Wu, Y. Zheng, *J. Mater. Chem. C* 2018, 6, 3499.
[14] G. Yu, J. Gao, J. C. Hummelen, F. Wudl, A. J. Heeger, *Science* 1995, 270, 1789.
[15] H. Lee, C. Park, D. H. Sin, J. H. Park, K. Cho, *Adv. Mater.* 2018, 30, 1800453.
[16] Y. Huang, E. J. Kramer, A. J. Heeger, G. C. Bazan, *Chem. Rev.* 2014, 114, 7006.
[17] G. Zhang, J. Zhao, P. C. Y. Chow, K. Jiang, J. Zhang, Z. Zhu, J. Zhang, F. Huang, H. Yan, *Chem. Rev.* 2018, 118, 3447.
[18] C. B. Nielsen, S. Holliday, H.-Y. Chen, S. J. Cryer, I. McCulloch, *Acc. Chem. Res.* 2015, 48, 2803.
[19] J. Hou, O. Inganas, R. H. Friend, F. Gao, *Nat. Mater.* 2018, 17, 119.
[20] J. Lee, S.-J. Ko, M. Seifrid, H. Lee, C. McDowell, B. R. Luginbuhl, A. Karki, K. Cho, T.-Q. Nguyen, G. C. Bazan, *Adv. Energy Mater.* 2018, 8, 1801209.
[21] Z. Yao, X. Liao, K. Gao, F. Lin, X. Xu, X. Shi, L. Zuo, F. Liu, Y. Chen, A. K.-Y. Jen, *J. Am. Chem. Soc.* 2018, 140, 2054.
[22] H. Yao, Y. Cui, R. Yu, B. Gao, H. Zhang, J. Hou, *Angew. Chem. Int. Ed.* 2017, 56, 3045.
[23] W. Wang, C. Yan, T.-K. Lau, J. Wang, K. Liu, Y. Fan, X. Lu, X. Zhan, *Adv. Mater.* 2017, 29, 1701308.
[24] Z. Xiao, X. Jia, D. Li, S. Wang, X. Geng, F. Liu, J. Chen, S. Yang, T. P. Russell, L. Ding, *Sci. Bull.* 2017, 62, 1494.
[25] J. Lee, S.-J. Ko, M. Seifrid, H. Lee, B. R. Luginbuhl, A. Karki, M. Ford, K. Rosenthal, K. Cho, T.-Q. Nguyen, G. C. Bazan, *Adv. Energy Mater.* 2018, 8, 1801212.
[26] W. Gao, M. Zhang, T. Liu, R. Ming, Q. An, K. Wu, D. Xie, Z. Luo, C. Zhong, F. Liu, F. Zhang, H. Yan, C. Yang, *Adv. Mater.* 2018, 30, 1800052.
[27] C. Li, T. Xia, J. Song, H. Fu, H. S. Ryu, K. Weng, L. Ye, H. Y. Woo, Y. Sun, *J. Mater. Chem. A* 2018, DOI 10.1039/C8TA11197A.
[28] W. Gao, T. Liu, C. Zhong, G. Zhang, Y. Zhang, R. Ming, L. Zhang, J. Xin, K. Wu, Y. Guo, W. Ma, H. Yan, Y. Liu, C. Yang, *ACS Energy Lett.* 2018, 3, 1760.
[29] H. Yao, Y. Chen, Y. Qin, R. Yu, Y. Cui, B. Yang, S. Li, K. Zhang, J. Hou, *Adv. Mater.* 2016, 28, 8283.
[30] L. J. A. Koster, V. D. Mihailetchi, H. Xie, P. W. M. Blom, *Appl. Phys. Lett.* 2005, 87, 203502.
[31] P. Schilinsky, C. Waldauf, C. J. Brabec, *Appl. Phys. Lett.* 2002, 81, 3885.
[32] C. M. Proctor, C. Kim, D. Neher, T.-Q. Nguyen, *Adv. Funct. Mater.* 2013, 23, 3584.
[33] D. Credgington, F. C. Jamieson, B. Walker, T.-Q. Nguyen, J. R. Durrant, *Adv. Mater.* 2012, 24, 2135.

[34] A. K. K. Kyaw, D. H. Wang, C. Luo, Y. Cao, T.-Q. Nguyen, G. C. Bazan, A. J. Heeger, *Adv. Energy Mater.* 2014, 4, 1301469.

[35] R. D. J. Vuuren, A. Armin, A. K. Pandey, P. L. Burn, P. Meredith, *Adv. Mater.* 2016, 28, 4766.

[36] X. Xu, X. Zhou, K. Zhou, Y. Xia, W. Ma, O. Inganas, *Adv. Funct. Mater.* 2018, 28, 1805570.

[37] X. Song, N. Gasparini, M. M. Nahid, H. Chen, S. M. Macphee, W. Zhang, V. Norman, C. Zhu, D. Bryant, H. Ade, I. McCulloch, D. Baran, *Adv. Funct. Mater.* 2018, 28, 1802895.

[38] X. Shi, L. Zuo, S. B. Jo, K. Gao, F. Lin, F. Liu, A. K.-Y. Jen, *Chem. Mater.* 2017, 29, 8369.

[39] S. Chen, Y. Liu, L. Zhang, P. C. Y. Chow, Z. Wang, G. Zhang, W. Ma, H. Yan, *J. Am. Chem. Soc.* 2017, 139, 6298.

[40] L. G. Kaake, J. J. Jasieniak, R. C. Bakus, G. C. Welch, D. Moses, G. C. Bazan, A. J. Heeger, *J. Am. Chem. Soc.* 2012, 134, 19828.

[41] G. Wang, N. D. Eastham, T. J. Aldrich, B. Ma, E. F. Manley, Z. Chen, L. X. Chen, M. O. de la Cruz, R. P. H. Chang, F. S. Melkonyan, A. Facchetti, T. J. Marks, *Adv. Energy Mater.* 2018, 8, 1702173.

[42] Z. Zhou, S. Xu, J. Song, Y. Jin, Q. Yue, Y. Qian, F. Liu, F. Zhang, X. Zhu, *Nat. Energy* 2018, 3, 952.

[43] S.-S. Wan, C. Chang, J.-L. Wang, G.-Z. Yuan, Q. Wu, M. Zhang, Y. Li, *Sol. RRL* 2019, 3, DOI 10.1002/solr.201800250.

[44] Y. Wu, H. Yang, Y. Zou, Y. Dong, J. Yuan, C. Cui, Y. Li, *Energy Environ. Sci.* 2018, DOI 10.1039/C8EE03608J.

[45] A. Zaban, M. Greenshtein, J. Bisquert, *ChemPhysChem* 2003, 4, 859.

[46] Design of Nonfullerene Acceptors with Near-Infrared Light Absorption Capab ilities. Advanced Energy Materials 2018, online. DOI: 10.1002/aenm.201.801_209

[47] Bandgap Narrowing in Mon-Fullerene Acceptors: Single; Atom Supstltution Leads to High Optoelectronic.ResponseBeyond 1000 nm. Adyancad Energy Materials 2018, online. DOI: 10.1002/aenm.201601212

[48] Asymmetrical Small Molecule Acceptor Enabling Non-fullerene Polymer Solar Cell with Fill Factor Approaching 79%. ACS Energy Lett. 2016, 3, 1760-1768

[49] Side-Chain Engineering of Nonfullerene Acceptors for Near-Infrared Organic Photodetectors and Photovoltaics, Jaewon Lee, Seo-Jin Ko, Hansol Lee, Jianfei Huang, Ziyue Zhu, Martin Seifrid, Joachim Vollbrecht, Viktor V. Brus. Akchheta Karki, Hengbin Wang, Kilwon Cho*, Thuc-Quyen Nguyen*, Guillermo C. Bazan* and Guillermo C. Bazan, *CS Energy Lett.* 2019, 4, 6, 1401-1409 https://doi.org/10.1021/acsenergylett.9b00721, including supporting information.

References for Second Example

[1] J. Byrnes, *Unexploded Ordnance Detection and Mitigation*, Springer Science & Business Media, 2008.

[2] H. Xu, J. Liu, J. Zhang, G. Zhou, N. Luo, N. Zhao, *Adv. Mater.* 2017, 29, 1700975.

[3] M. S. Milián, J. Escofet, *Opt. Lett.* 2004, 29, 1440.

[4] P. Jonsson, J. Casselgren, B. Thörnberg, *IEEE Sens. J.* 2015, 15, 1641.

[5] R. Weissleder, *Nat. Biotechnol.* 2001, 19, 316.

[6] X. Liu, Y. Lin, Y. Liao, J. Wu, Y. Zheng, *J. Mater. Chem. C* 2018, 6, 3499.

[7] Z. Wu, W. Yao, A. E. London, J. D. Azoulay, T. N. Ng, *Adv. Funct. Mater.* 2018, 28, 1800391.

[8] Q. Lin, A. Armin, P. L. Burn, P. Meredith, *Laser Photonics Rev.* 2016, 10, 1047.

[9] Y. Yao, Y. Liang, V. Shrotriya, S. Xiao, L. Yu, Y. Yang, *Adv. Mater.* 2007, 19, 3979.

[10] X. Gong, M. Tong, Y. Xia, W. Cai, J. S. Moon, Y. Cao, G. Yu, C.-L. Shieh, B. Nilsson, A. J. Heeger, *Science* 2009, 325, 1665.

[11] X. Zhou, D. Yang, D. Ma, *Adv. Opt. Mater.* 2015, 3, 1570.

[12] H. Zhang, S. Jenatsch, J. De Jonghe, F. Nüesch, R. Steim, A. C. Véron, R. Hany, *Sci. Rep.* 2015, 5, 9439.

[13] M. Young, J. Suddard-Bangsund, T. J. Patrick, N. Pajares, C. J. Traverse, M. C. Barr, S. Y. Lunt, R. R. Lunt, *Adv. Opt. Mater.* 2016, 4, 1028.

[14] M.-S. Choi, S. Chae, H. J. Kim, J.-J. Kim, *ACS Appl. Mater. Interfaces* 2018, 10, 25614.

[15] L. Xiao, S. Chen, X. Chen, X. Peng, Y. Cao, X. Zhu, *J. Mater. Chem. C* 2018, 6, 3341.

[16] H. Yao, Y. Cui, R. Yu, B. Gao, H. Zhang, J. Hou, *Angew. Chem. Int. Ed.* 2017, 56, 3045.

[17] J. Lee, S.-J. Ko, M. Seifrid, H. Lee, B. R. Luginbuhl, A. Karki, M. Ford, K. Rosenthal, K. Cho, T.-Q. Nguyen, G. C. Bazan, *Adv. Energy Mater.* 2018, 8, 1801212.

[18] W. Li, Y. Xu, X. Meng, Z. Xiao, R. Li, L. Jiang, L. Cui, M. Zheng, C. Liu, L. Ding, Q. Lin, *Adv. Funct. Mater.* 2019, 29, 1808948.

[19] G. Wu, R. Fu, J. Chen, W. Yang, J. Ren, X. Guo, Z. Ni, X. Pi, C.-Z. Li, H. Li, H. Chen, *Small* 2018, 14, 1802349.

[20] H. Wang, S. Xing, Y. Zheng, J. Kong, J. Yu, A. D. Taylor, *ACS Appl. Mater. Interfaces* 2018, 10, 3856.

[21] K.-J. Baeg, M. Binda, D. Natali, M. Caironi, Y.-Y. Noh, *Adv. Mater.* 2013, 25, 4267.

[22] A. Armin, M. Hambsch, I. K. Kim, P. L. Burn, P. Meredith, E. B. Namdas, *Laser Photonics Rev.* 2014, 8, 924.

[23] J. Lee, S.-J. Ko, H. Lee, J. Huang, Z. Zhu, M. Seifrid, J. Vollbrecht, V. V. Brus, A. Karki, H. Wang, K. Cho, T.-Q. Nguyen, G. C. Bazan, *ACS Energy Lett.* 2019, DOI 10.1021/acsenergylett.9b00721.

[24] S. Xiong, J. Tong, L. Mao, Z. Li, F. Qin, F. Jiang, W. Meng, T. Liu, W. Li, Y. Zhou, *J. Mater. Chem. C* 2016, 4, 1414.

[25] X. Hu, Y. Dong, F. Huang, X. Gong, Y. Cao, *J. Phys. Chem. C* 2013, 117, 6537.

[26] J. Qi, L. Ni, D. Yang, X. Zhou, W. Qiao, M. Li, D. Ma, Z. Yuan Wang, *J. Mater. Chem. C* 2014, 2, 2431.

[27] C. M. Proctor, T.-Q. Nguyen, *Appl. Phys. Lett.* 2015, 106, 083301.

[28] S. M. Sze, K. K. Ng, *Physics of Semiconductor Devices*, John Wiley & Sons, 2006.

[29] V. V. Brus, O. L. Maslyanchuk, M. M. Solovan, P. D. Maryanchuk, I. Fodchuk, V. A. Gnatyuk, N. D. Vakhnyak, S. V. Melnychuk, T. Aoki, *Sci. Rep.* 2019, 9, 1065.

[30] M. A. Lampert, P. Mark, *Current Injection in Solids*, Academic Press, 1970.

[31] Z. Wu, Y. Zhai, H. Kim, J. D. Azoulay, T. N. Ng, *Acc. Chem. Res.* 2018, 51, 3144.

[32] I. K. Kim, J. H. Jo, J. (Brian) Lee, Y. J. Choi, *Org. Electron.* 2018, 57, 89.

[33] Y. Fang, A. Armin, P. Meredith, J. Huang, *Nat. Photonics* 2019, 13, 1.

[34] Y. Fang, J. Huang, *Adv. Mater.* 2015, 27, 2804.

[35] S. Manna, S. Das, S. P. Mondal, R. Singha, S. K. Ray, *J. Phys. Chem. C* 2012, 116, 7126.

[36] J.-Q. Liu, Y. Gao, G.-A. Wu, X.-W. Tong, C. Xie, L.-B. Luo, L. Liang, Y.-C. Wu, *ACS Appl. Mater. Interfaces* 2018, 10, 27850.

[37] J. Miao, F. Zhang, *Laser Photonics Rev.* 2019, 13, 1800204.
[38] J. Miao, F. Zhang, M. Du, W. Wang, Y. Fang, *Adv. Opt. Mater.* 2018, 6, 1800001.
[39] L. Li, F. Zhang, W. Wang, Q. An, J. Wang, Q. Sun, M. Zhang, *ACS Appl. Mater. Interfaces* 2015, 7, 5890.
[40] M. Biele, C. M. Benavides, J. Hürdler, S. F. Tedde, C. J. Brabec, O. Schmidt, *Adv. Mater. Technol.* 2019, 4, 1800158.
[41] J. Allen, *Physiol. Meas.* 2007, 28, R1.
[42] A High-Performance Solution-Processed Organic Photodetector for Near-Infrared Sensing, Jianfei Huang, Jaewon Lee, Joachim Vollbrecht, Viktor V. Brus, Alana L. Dixon, David Xi Cao, Ziyue Zhu, Zhifang Du, Hengbin Wang, Kilwon Cho, Guillermo C. Bazan and Thuc-Quyen Nguyen, Volume 32, Issue 1 Jan. 9, 2020, 1906027, https://doi.org/10.1002/adma.201906027, including supporting information.

References for Example 3

(1) Dong, H.; Zhu, H.; Meng, Q.; Gong, X.; Hu, W. Organic Photoresponse Materials and Devices. *Chem. Soc. Rev.* 2012, 41, 1754-1808.
(2) Ying, L.; Huang, F.; Bazan, G. C. Regioregular Narrow-Bandgap-Conjugated Polymers for Plastic Electronics. *Nat. Commun.* 2017, 8, 14047.
(3) Cheng, Y.-J.; Yang, S.-H.; Hsu, C.-S. Synthesis of Conjugated Polymers for Organic Solar Cell Applications. *Chem. Rev.* 2009, 109, 5868-5923.
(4) Arias, A. C.; MacKenzie, J. D.; McCulloch, I.; Rivnay, J.; Salleo, A. Materials and Applications for Large Area Electronics: Solution-Based Approaches. *Chem. Rev.* 2010, 110, 3-24.
(5) Dou, L.; Liu, Y.; Hong, Z.; Li, G.; Yang, Y. Low-Bandgap Near-IR Conjugated Polymers/Molecules for Organic Electronics. *Chem. Rev.* 2015, 115, 12633-12665.
(6) Brus, V. V.; Lee, J.; Luginbuhl, B. R.; Ko, S.-J.; Bazan, G. C.; Nguyen, T.-Q. Solution-Processed Semitransparent Organic Photovoltaics: From Molecular Design to Device Performance. *Adv. Mater.* 2019, 31, 1900904.
(7) Tai, Q.; Yan, F. Emerging Semitransparent Solar Cells: Materials and Device Design. *Adv. Mater.* 2017, 29, 1700192.
(8) Traverse, C. J.; Pandey, R.; Barr, M. C.; Lunt, R. R. Emergence of Highly Transparent Photovoltaics for Distributed Applications. *Nat. Energy* 2017, 2, 849-860.
(9) Emmott, C. J. M.; Rohr, J. A.; Campoy-Quiles, M.; Kirchartz, T.; Urbina, A.; Ekins-Daukes, N. J.; Nelson, J. Organic Photovoltaic Greenhouses: A Unique Application for Semi-Transparent PV?. *Energy Environ. Sci.* 2015, 8, 1317-1328.
(10) García de Arquer, F. P.; Armin, A.; Meredith, P.; Sargent, E. H. Solution-Processed Semiconductors for next-Generation Photodetectors. *Nat. Rev. Mater.* 2017, 2, 16100.
(11) Liu, X.; Lin, Y.; Liao, Y.; Wu, J.; Zheng, Y. Recent Advances in Organic Near-Infrared Photodiodes. *J. Mater. Chem. C* 2018, 6, 3499-3513.
(12) Wu, Z.; Zhai, Y.; Kim, H.; Azoulay, J. D.; Ng, T. N. Emerging Design and Characterization Guidelines for Polymer-Based Infrared Photodetectors. *Acc. Chem. Res.* 2018, 51, 3144-3153.
(13) Huang, Y.; Kramer, E. J.; Heeger, A. J.; Bazan, G. C. Bulk Heterojunction Solar Cells: Morphology and Performance Relationships. *Chem. Rev.* 2014, 114, 7006-7043.
(14) Yu, G.; Gao, J.; Hummelen, J. C.; Wudl, F.; Heeger, A. J. Polymer Photovoltaic Cells: Enhanced Efficiencies via a Network of Internal Donor-Acceptor Heterojunctions. *Science* 1995, 270, 1789-1791.
(15) Lee, H.; Park, C.; Sin, D. H.; Park, J. H.; Cho, K. Recent Advances in Morphology Optimization for Organic Photovoltaics. *Adv. Mater.* 2018, 30, 1800453.
(16) Nuzzo, D. D.; Wetzelaer, G.-J. A. H.; Bouwer, R. K. M.; Gevaerts, V. S.; Meskers, S. C. J.; Hummelen, J. C.; Blom, P. W. M.; Janssen, R. A. J. Simultaneous Open-Circuit Voltage Enhancement and Short-Circuit Current $E_{loss}$ in Polymer: Fullerene Solar Cells Correlated by Reduced Quantum Efficiency for Photoinduced Electron Transfer. *Adv. Energy Mater.* 2013, 3, 85-94.
(17) Mishra, A.; Keshtov, M. L.; Looser, A.; Singhal, R.; Stolte, M.; Würthner, F.; Bauerle, P.; Sharma, G. D. Unprecedented Low Energy Losses in Organic Solar Cells with High External Quantum Efficiencies by Employing Non-Fullerene Electron Acceptors. *J. Mater. Chem. A* 2017, 5, 14887-14897.
(18) Li, Y.; Zhong, L.; Gautam, B.; Bin, H.-J.; Lin, J.-D.; Wu, F.-P.; Zhang, Z.; Jiang, Z.-Q.; Zhang, Z.-G.; Gundogdu, K.; et al. A Near-Infrared Non-Fullerene Electron Acceptor for High Performance Polymer Solar Cells. *Energy Environ. Sci.* 2017, 10, 1610-1620.
(19) Bakulin, A. A.; Rao, A.; Pavelyev, V. G.; van Loosdrecht, P. H. M.; Pshenichnikov, M. S.; Niedzialek, D.; Cornil, J.; Beijonne, D.; Friend, R. H. The Role of Driving Energy and Delocalized States for Charge Separation in Organic Semiconductors. *Science* 2012, 335, 1340-1344.
(20) Sini, G.; Schubert, M.; Risko, C.; Roland, S.; Lee, O. P.; Chen, Z.; Richter, T. V.; Dolfen, D.; Coropceanu, V.; Ludwigs, S.; Scherf, U.; Facchetti, A.; Frechet, J. M.; Neher, D. On the Molecular Origin of Charge Separation at the Donor-Acceptor Interface. *Adv. Energy Mater.* 2018, 8, 1702232.
(21) Baran, D.; Kirchartz, T.; Wheeler, S.; Dimitrov, S.; Abdelsamie, M.; Gorman, J.; S. Ashraf, R.; Holliday, S.; Wadsworth, A.; Gasparini, N.; et al. Reduced Voltage Losses Yield 10% Efficient Fullerene Free Organic Solar Cells with >1 V Open Circuit Voltages. *Energy Environ. Sci.* 2016, 9, 3783-3793.
(22) Lee, J.; Ko, S.-J.; Seifrid, M.; Lee, H.; McDowell, C.; Luginbuhl, B. R.; Karki, A.; Cho, K.; Nguyen, T.-Q.; Bazan, G. C. Design of Nonfullerene Acceptors with Near-Infrared Light Absorption Capabilities. *Adv. Energy Mater.* 2018, 8, 1801209.
(23) Gelinas, S.; Rao, A.; Kumar, A.; Smith, S. L.; Chin, A. W.; Clark, J.; van der Poll, T. S.; Bazan, G. C.; Friend, R. H. Ultrafast Long-Range Charge Separation in Organic Semiconductor Photovoltaic Diodes. *Science* 2014, 343, 512-516.
(24) Wang, W.; Yan, C.; Lau, T.-K.; Wang, J.; Liu, K.; Fan, Y.; Lu, X.; Zhan, X. Fused Hexacyclic Nonfullerene Acceptor with Strong Near-Infrared Absorption for Semitransparent Organic Solar Cells with 9.77% Efficiency. *Adv. Mater.* 2017, 29, 1701308.
(25) Gao, W.; Liu, T.; Ming, R.; Luo, Z.; Wu, K.; Zhang, L.; Xin, J.; Xie, D.; Zhang, G.; Ma, W.; Yan, H.; Yang, C. Near-Infrared Small Molecule Acceptor Enabled High-Performance Nonfullerene Polymer Solar Cells with Over 13% Efficiency. *Adv. Funct. Mater.* 2018, 28, 1803128.
(26) Dai, S.; Li, T.; Wang, W.; Xiao, Y.; Lau, T.-K.; Li, Z.; Liu, K.; Lu, X.; Zhan, X. Enhancing the Performance of Polymer Solar Cells via Core Engineering of NIR-Absorbing Electron Acceptors. *Adv. Mater.* 2018, 30, 1706571.

(27) Hou, J.; Inganäs, O.; Friend, R. H.; Gao, F. Organic Solar Cells Based on Non-Fullerene Acceptors. *Nat. Mater.* 2018, 17, 119-128.

(28) Cheng, P.; Li, G.; Zhan, X.; Yang, Y. Next-Generation Organic Photovoltaics Based on Non-Fullerene Acceptors. *Nat. Photonics* 2018, 12, 131.

(29) Lin, Y.; Zhan, X. Oligomer Molecules for Efficient Organic Photovoltaics. *Acc. Chem. Res.* 2016, 49, 175-183.

(30) Nielsen, C. B.; Holliday, S.; Chen, H.-Y.; Cryer, S. J.; McCulloch, I. Non-Fullerene Electron Acceptors for Use in Organic Solar Cells. *Acc. Chem. Res.* 2015, 48, 2803-2812.

(31) Lee, J.; Ko, S.-J.; Seifrid, M.; Lee, H.; Luginbuhl, B. R.; Karki, A.; Ford, M.; Rosenthal, K.; Cho, K.; Nguyen, T.-Q.; et al. Bandgap Narrowing in Non-Fullerene Acceptors: Single Atom Substitution Leads to High Optoelectronic Response Beyond 1000 Nm. *Adv. Energy Mater.* 2018, 8, 1801212.

(32) Lee, J.; Ko, S.-J.; Lee, H.; Huang, J.; Zhu, Z.; Seifrid, M.; Vollbrecht, J.; Brus, V. V.; Karki, A.; Wang, H.; et al. Side-Chain Engineering of Nonfullerene Acceptors for Near-Infrared Organic Photodetectors and Photovoltaics. *ACS Energy Lett.* 2019, 4, 1401-1409.

(33) Yao, H.; Cui, Y.; Yu, R.; Gao, B.; Zhang, H.; Hou, J. Design, Synthesis, and Photovoltaic Characterization of a Small Molecular Acceptor with an Ultra-Narrow Band Gap. *Angew. Chem. Int. Ed.* 2017, 56, 3045-3049.

(34) Yao, Z.; Liao, X.; Gao, K.; Lin, F.; Xu, X.; Shi, X.; Zuo, L.; Liu, F.; Chen, Y.; Jen, A. K.-Y. Dithienopicenocarbazole-Based Acceptors for Efficient Organic Solar Cells with Optoelectronic Response Over 1000 Nm and an Extremely Low Energy Loss. *J. Am. Chem. Soc.* 2018, 140, 2054-2057.

(35) Xiao, Z.; Jia, X.; Li, D.; Wang, S.; Geng, X.; Liu, F.; Chen, J.; Yang, S.; Russell, T. P.; Ding, L. 26 mA cm-2Jsc from Organic Solar Cells with a Low-Bandgap Nonfullerene Acceptor. *Sci. Bull.* 2017, 62, 1494-1496.

(36) Li, Y.; Lin, J.-D.; Che, X.; Qu, Y.; Liu, F.; Liao, L.-S.; Forrest, S. R. High Efficiency Near-Infrared and Semitransparent Non-Fullerene Acceptor Organic Photovoltaic Cells. *J. Am. Chem. Soc.* 2017, 139, 17114-17119.

(37) Yao, H.; Chen, Y.; Qin, Y.; Yu, R.; Cui, Y.; Yang, B.; Li, S.; Zhang, K.; Hou, J. Design and Synthesis of a Low Bandgap Small Molecule Acceptor for Efficient Polymer Solar Cells. *Adv. Mater.* 2016, 28, 8283-8287.

(38) Liu, Y.; Li, M.; Yang, J.; Xue, W.; Feng, S.; Song, J.; Tang, Z.; Ma, W.; Bo, Z. High-Efficiency As-Cast Organic Solar Cells Based on Acceptors with Steric Hindrance Induced Planar Terminal Group. *Adv. Energy Mater.* 2019, 9, 1901280.

(39) Wang, W.; Zhao, B.; Cong, Z.; Xie, Y.; Wu, H.; Liang, Q.; Liu, S.; Liu, F.; Gao, C.; Wu, H.; et al. Nonfullerene Polymer Solar Cells Based on a Main-Chain Twisted Low-Bandgap Acceptor with Power Conversion Efficiency of 13.2%. *ACS Energy Lett.* 2018, 3, 1499-1507.

(40) Bin, H.; Yang, Y.; Peng, Z.; Ye, L.; Yao, J.; Zhong, L.; Sun, C.; Gao, L.; Huang, H.; Li, X.; Qiu, B.; Xue, L.; Zhang, Z.-G.; Ade, H.; Li, Y. Effect of Alkylsilyl Side-Chain Structure on Photovoltaic Properties of Conjugated Polymer Donors. *Adv. Energy Mater.* 2018, 8, 1702324.

(41) Privado, M.; Seco, C. R.; Singhal, R.; Cruz, P. d. l.; Langa, F.; Sharma, G. D.; Palomares. E. Reduced Energy Offsets and Low Energy Losses Lead to Efficient (~10% at 1 sun) Ternary Organic Solar Cells. *ACS Energy Letters* 2018, 3, 2418-2424.

(42) Bin, H.; Zhang, Z.-G.; Gao, L.; Chen, S.; Zhong, L.; Xue, L.; Yang, C.; Li, Y. Non-Fullerene Polymer Solar Cells Based on Alkylthio and Fluorine Substituted 2D-Conjugated Polymers Reach 9.5% Efficiency. *J. Am. Chem. Soc.* 2016, 138, 4657-4664.

(43) Yao, H.; Cui, Y.; Qian, D.; Ponseca, Jr. C. S.; Honarfar, A.; Xu, Y.; Xin, J.; Chen, Z.; Hong, L.; Gao, B.; Yu, R.; Zu, Y.; Ma, W.; Chabera, P.; Pullerits, T.; Yartsev, A.; Gao, F.; Hou, J. 14.7% Efficiency Organic Photovoltaic Cells Enabled by Active Materials with a Large Electrostatic Potential Difference. *J. Am. Chem. Soc.* 2019, 141, 7743-7750.

(44) Liu, J.; Chen, S.; Qian, D.; Gautam, B.; Yang, G.; Zhao, J.; Bergqvist, J.; Zhang, F.; Ma, W.; Ade, H.; Inganas, O.; Gundogdu, K.; Gao, F.; Yan, H. Fast Charge Separation in a Non-Fullerene Organic Solar Cell with a Small Driving Force. *Nat. Energy* 2016, 1, 16089.

(45) Bin, H.; Gao, L.; Zhang, Z.-G.; Yang, Y.; Zhang, Y.; Zhang, C.; Chen, S.; Xue, L.; Yang, C.; Xiao, M.; Li, Y. 11.4% Efficiency Non-Fullerene Polymer Solar Cells with Trialkylsilyl Substituted 2D-Conjugated Polymer as Donor. *Nat. Commun.* 2016, 7, 13651.

(46) Chen, S.; Wang, Y.; Zhang, L.; Zhao, J.; Chen, Y.; Zhu, D.; Yao, H.; Zhang, G.; Ma, W.; Friend, R. H.; Chow, P. C. Y.; Gao, F.; Yan, H. Efficient Nonfullerene Organic Solar Cells with Small Driving Forces for Both Hole and Electron Transfer. *Adv. Mater.* 2018, 30, 1804215.

(47) Wang, Y.; Qian, D.; Cui, Y.; Zhang, H.; Hou, J.; Vandewal, K.; Kirchartz, T.; Gao, F. Optical Gaps of Organic Solar Cells as a Reference for Comparing Voltage Losses. *Adv. Energy Mater.* 2018, 8, 1801352.

(48) Li, S.; Zhan, L.; Sun, C.; Zhu, H.; Zhou, G.; Yang, W.; Shi, M.; Li, C.-Z.; Hou, J.; Li, Y.; Chen, H. Highly Efficient Fullerene-Free Organic Solar Cells Operate at Near Zero Highest Occupied Molecular Orbital Offsets. *J. Am. Chem. Soc.* 2019, 141, 3073-3082.

(49) Li, C.; Fu, H.; Xia, T.; Sun, Y. Asymmetric Nonfullerene Small Molecule Acceptors for Organic Solar Cells. *Adv. Energy Mater.* 2019, 9, 1900999.

(50) Gao, W.; Zhang, M.; Liu, T.; Ming, R.; An, Q.; Wu, K.; Xie, D.; Luo, Z.; Zhong, C.; Liu, F.; et al. Asymmetrical Ladder-Type Donor-Induced Polar Small Molecule Acceptor to Promote Fill Factors Approaching 77% for High-Performance Nonfullerene Polymer Solar Cells. *Adv. Mater.* 2018, 30, 1800052.

(51) Fei, Z.; Eisner, F. D.; Jiao, X.; Azzouzi, M.; Rohr, J. A.; Han, Y.; Shahid, M.; Chesman, A. S. R.; Easton, C. D.; McNeill, C. R.; et al. An Alkylated Indacenodithieno[3, 2-b]Thiophene-Based Nonfullerene Acceptor with High Crystallinity Exhibiting Single Junction Solar Cell Efficiencies Greater than 13% with Low Voltage Losses. *Adv. Mater.* 2018, 30, 1705209.

(52) Song, X.; Gasparini, N.; Nahid, M. M.; Chen, H.; Macphee, S. M.; Zhang, W.;

Norman, V.; Zhu, C.; Bryant, D.; Ade, H.; McCulloch, I.; Baran, D. A Highly Crystalline Fused-Ring n-Type Small Molecule for Non-Fullerene Acceptor Based Organic Solar Cells and Field-Effect Transistors. *Adv. Funct. Mater.* 2018, 28, 1802895.

(50) Further information on one or more embodiments of the present invention can be found in this unpublished manuscript entitled Bandgap Tailored Nonfullerene Acceptors for Low Energy $E_{loss}$ Near-Infrared Organic Photovoltaics by Jaewon Lee, Seyeong Song, Jianfei Huang, Zhifang Du, Hansol Lee, Ziyue Zhu, Seo-Jin Ko, Thuc-Quyen Nguyen, Jin Young Kim, Kilwon Cho,*‡ Guillermo C. Bazan*'submitted herewith.

CONCLUSION

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A composition of matter, comprising:
one or more organic semiconducting molecules having the structure (and isomers thereof):

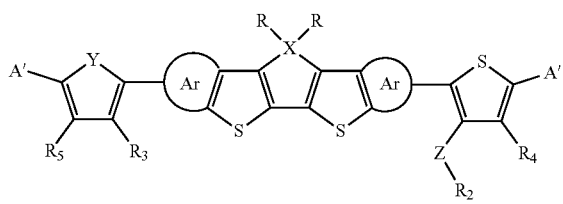

wherein:
each Ar is independently a substituted or non-substituted aromatic functional group, or each Ar is independently nothing and the valence of its respective thiophene ring is completed with hydrogen;
X is C, Si, Ge, N or P; Y is O, S, Se or N—$R_6$;
Z is O, S, Se, or N—$R_6$;
each R, $R_2$, $R_3$, $R_4$, $R_5$ and $R_6$ is independently hydrogen or a substituted or non-substituted alkyl, aryl or alkoxy chain but $R_3$ is different from Z—$R_2$;
$R_4$ is either a hydrogen or the same as Z—$R_2$;
$R_5$ is either a hydrogen or the same as $R_3$; and
A' is an acceptor moiety.

2. The composition of matter of claim 1, wherein A' has the structure (and isomers thereof):

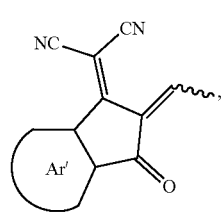

where

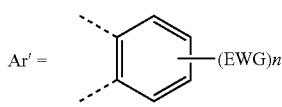

wherein EWG is any electron withdrawing group.

3. The composition of matter of claim 2, wherein Ar' is one of the following:

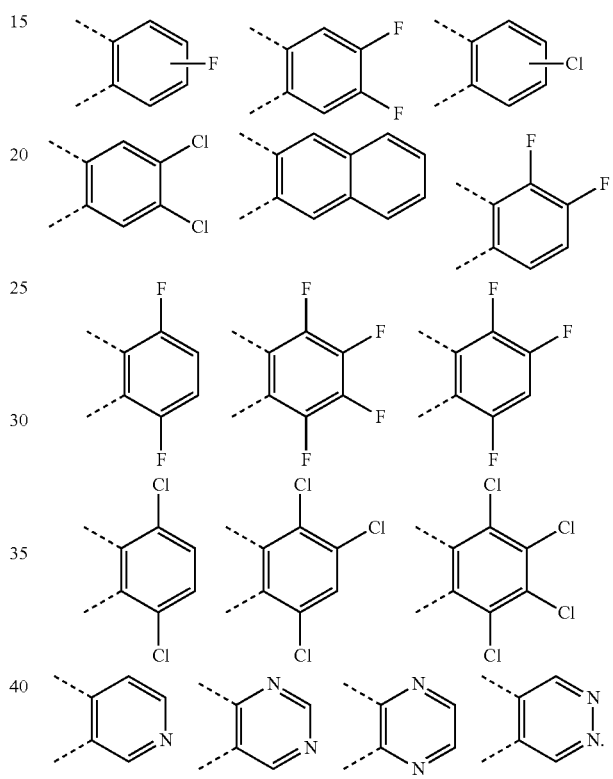

4. The composition of matter of claim 1, wherein each of the one or more organic semiconducting molecules have the structure (and isomers thereof):

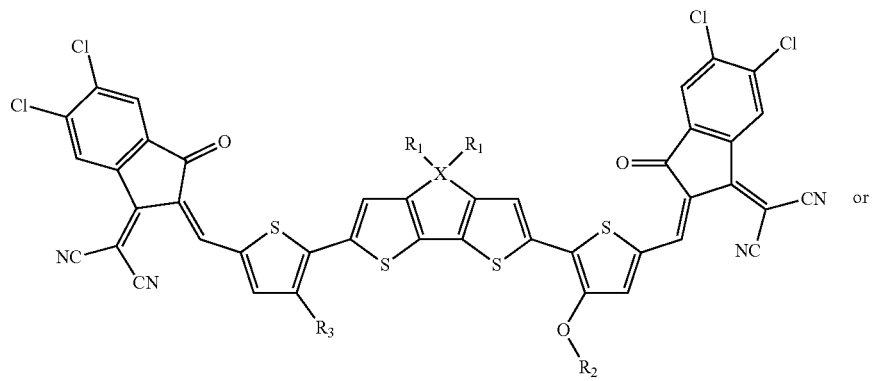

or

-continued

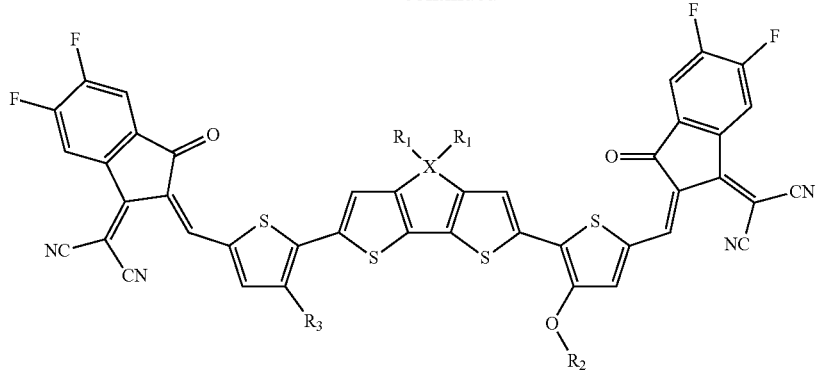

wherein X is C, Si, Ge, N or P; Z is O, Y is S, $R_4$ is hydrogen, $R_5$ is hydrogen, each $R_1$, $R_2$ and $R_3$ is independently hydrogen or a substituted or non-substituted alkyl, aryl or alkoxy chain, and $R_3$ is different from $OR_2$.

5. The composition of matter of claim 4, wherein each of the one or more organic semiconducting molecules have the structure (and isomers thereof):

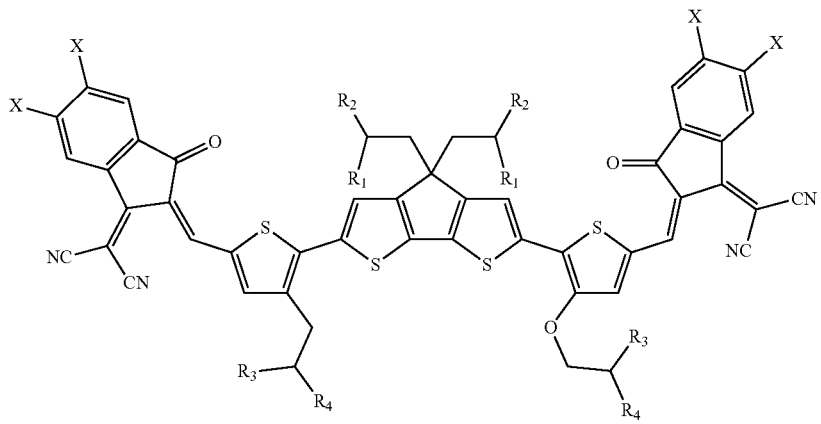

where:
X is F or Cl, and
$R_1$, $R_2$, $R_3$, $R_4$ are independently hydrogen or a substituted or non-substituted alkyl, aryl or alkoxy chain.

6. The composition of matter of claim 1, wherein the dithiophene has the side chains $R_1$ soluble in a solvent used to solution process a device comprising the composition of matter.

7. A device comprising an active region including the composition of matter of claim 1, wherein each of the organic semiconducting molecules are an electron acceptor.

8. The device of claim 7, wherein:
the active region comprises each of the electron acceptors forming a heterojunction with an electron donor comprising a second organic semiconducting molecule, and
the active region has a thickness of at least 300 nanometers or in a range of 200 nm to 1 micrometer.

9. The device of claim 8, further comprising:
a cathode;
an anode; and
the active region between the cathode and the anode; and wherein:

holes and electrons are generated in the active region in response to electromagnetic radiation incident on the active region,
the electrons are collected in the electron acceptor and are transmitted through to the cathode, and
the holes are collected in the electron donor and transmitted through to the anode.

10. The device of claim 9, further comprising:
a hole blocking layer between the cathode and the active region, and
an electron blocking layer between the anode and the active region.

11. The device of claim 8, wherein the device is an organic solar cell outputting current in response to sunlight absorbed in the active region.

12. The device of claim 8, wherein the device is a photodetector outputting current in response to infrared electromagnetic radiation absorbed in the active region.

13. The device of claim 8, wherein the device is a solar cell or photodetector having an external quantum efficiency (EQE) above 60% in the wavelength range of 600-950 nm.

14. The device of claim 7, wherein the composition of matter further comprises electron donors comprising at least one compound selected from PTB7-Th, another BDT based polymer, a CPDT based polymer, a DPP based polymer, or a DTP based polymer.

15. The composition of matter of claim 1, further comprising a plurality of electron donors and a plurality of the organic semiconducting molecules that are phase separated, wherein the organic semiconducting molecules are disposed in a hierarchical network and the electron donors comprising the second organic semiconducting molecules occupy spaces in the hierarchical network.

16. The composition of matter of claim 15, wherein the hierarchical network comprises larger mid rib shaped regions connected by smaller or thinner regions.

17. The composition of matter of claim 15, wherein the composition of matter is solution processed with an additive that promotes formation of the hierarchical network.

18. A method of making a device, comprising:
  solution processing a composition of matter including electron donor molecules and electron acceptor molecules of the structure (and isomers thereof):

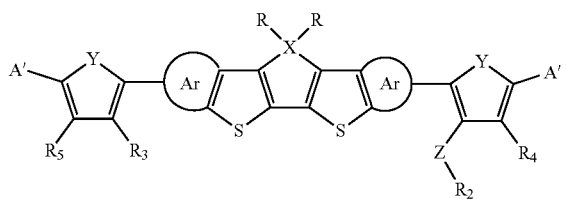

wherein:
each Ar is independently a substituted or non-substituted aromatic functional group, or each Ar is independently nothing and the valence of its respective thiophene ring is completed with hydrogen;
X is C, Si, Ge, N or P; Y is O, S, Se or N—$R_6$;
Z is O, S, Se, or N—$R_6$;
each R, $R_2$, $R_3$, $R_4$, $R_5$ and $R_6$ is independently hydrogen or a substituted or non-substituted alkyl, aryl or alkoxy chain but $R_3$ is different from Z—$R_2$;
$R_4$ is either a hydrogen or the same as Z—$R_2$;
$R_5$ is either a hydrogen or the same as $R_3$; and
A' is an acceptor moiety, wherein the electron acceptor is solution process in an active region of a solar cell, photodetector, or transistor; and
combining the composition of matter with an additive so that:
  the plurality of the electron donor molecules and the plurality of electron acceptor molecules are phase separated,
  the electron acceptor molecules are disposed in a hierarchical network and
  the electron donor molecules occupy spaces in the hierarchical network.

* * * * *